(12) United States Patent
Badik et al.

(10) Patent No.: US 11,633,539 B1
(45) Date of Patent: Apr. 25, 2023

(54) INFUSION AND MONITORING SYSTEM

(71) Applicant: KURE, LLC, Newark, DE (US)

(72) Inventors: Yale Badik, Madison, CT (US);
Deanna Felker, West Hills, CA (US)

(73) Assignee: KURE, LLC

( * ) Notice: Subject to any disclaimer, the term of this patent is extended or adjusted under 35 U.S.C. 154(b) by 0 days.

(21) Appl. No.: 17/739,673

(22) Filed: May 9, 2022

(51) Int. Cl.
  *A61M 5/172*  (2006.01)
  *G16H 20/17*  (2018.01)
  *G16H 40/67*  (2018.01)
  *A61B 5/00*  (2006.01)

(52) U.S. Cl.
  CPC .......... *A61M 5/1723* (2013.01); *G16H 20/17* (2018.01); *G16H 40/67* (2018.01); *A61B 5/4839* (2013.01); *A61M 2205/18* (2013.01); *A61M 2205/3303* (2013.01); *A61M 2205/3331* (2013.01); *A61M 2205/587* (2013.01); *A61M 2230/10* (2013.01); *A61M 2230/63* (2013.01)

(58) Field of Classification Search
  CPC ............ A61M 5/1723; A61M 2205/18; A61M 2205/3303; A61M 2205/3331; A61M 2205/587; A61M 2230/10; A61M 2230/63; G16H 20/17; G16H 40/67
  See application file for complete search history.

(56) References Cited

U.S. PATENT DOCUMENTS

| | | | |
|---|---|---|---|
| 6,689,091 B2 | 2/2004 | Bui et al. | |
| 8,082,452 B2 | 12/2011 | Jajodia | |
| 8,285,328 B2 | 10/2012 | Caffey et al. | |
| 8,566,269 B2 | 10/2013 | Jajodia et al. | |
| 8,882,703 B2 | 11/2014 | Hickle | |
| 9,031,793 B2 | 5/2015 | Lynn et al. | |
| 9,067,016 B2 | 6/2015 | Li | |
| 9,203,861 B2 | 12/2015 | Albanese et al. | |
| 9,436,822 B2 | 9/2016 | Ghosh et al. | |
| 9,649,439 B2 | 5/2017 | John | |
| 9,814,426 B2 | 11/2017 | Connor | |
| 9,846,588 B2 | 12/2017 | Ghosh et al. | |
| 10,783,989 B2 | 9/2020 | Bangera et al. | |
| 10,956,184 B2 | 3/2021 | Ghosh et al. | |
| 2008/0058773 A1* | 3/2008 | John | A61N 1/37235 604/891.1 |
| 2008/0154177 A1 | 6/2008 | Moubayed et al. | |
| 2010/0054481 A1 | 3/2010 | Jajodia et al. | |

(Continued)

*Primary Examiner* — Nathan R Price
*Assistant Examiner* — Anh Bui
(74) *Attorney, Agent, or Firm* — Dave Law Group LLC; Raj S. Dave

(57) ABSTRACT

Embodiments relate to a system, comprising a timer module comprising a timer configured to set a time for a session, an infusion module comprising an infusing device configured for administering a drug to a patient, a patient monitoring module comprising a first sensor configured for monitoring a physiological condition of the patient, a drug monitoring and control module comprising a second sensor configured for monitoring a drug delivery to the patient, an alarm generating module comprising signal generator that generates an indication signal when a value of the physiological condition is outside a predefined threshold, and wherein the time for the session is dynamically adjusted during the session, and wherein the drug delivery is dynamically adjusted during the session.

20 Claims, 19 Drawing Sheets

(56) References Cited

U.S. PATENT DOCUMENTS

| | | | |
|---|---|---|---|
| 2010/0058456 A1 | 3/2010 | Jajodia et al. | |
| 2011/0066036 A1* | 3/2011 | Zilca | A61B 5/165 |
| | | | 600/300 |
| 2013/0167052 A1* | 6/2013 | Niesslein | G16H 20/17 |
| | | | 715/764 |
| 2017/0185745 A1* | 6/2017 | Wartski | G16H 20/13 |
| 2018/0137247 A1* | 5/2018 | Bore | G16H 80/00 |
| 2018/0158555 A1 | 6/2018 | Cashman et al. | |
| 2021/0174778 A1 | 6/2021 | Goldstein | |
| 2022/0111212 A1* | 4/2022 | Howard | A61B 5/4836 |

* cited by examiner

INFUSION AND MONITORING SYSTEM

FIELD OF THE INVENTION

This invention relates to the systems and methods for infusion of a drug to a patient and monitoring the patient and drug delivery. The invention is more particularly concerned with systems and processes involving adjusting drug infusion and session time based on real-time monitoring and analysis of physiological conditions of the patient. It further involves generating alarm signals for the irregularities found in the infusion or irregularities found in patient physiological conditions.

RELATED APPLICATIONS

The present invention is related to U.S. patent application Ser. No. 17/739,463; filed May 9, 2022) entitled TREATMENT CHAIR; application Ser. No. 17/739,588; filed May 9, 2022) entitled SMART EYE MASK; application Ser. No. 17/739,756, filed May 9, 2022) entitled SMART STORAGE SYSTEM application Ser. No. 17/739,835, filed May 9, 2022) entitled SMART DISPENSING SYSTEM which are being concurrently filed. All U.S. Patent Applications referred above are incorporated, for the purposes of written description, herein by reference in their entirety.

BACKGROUND

"According to another aspect of the present invention, the medical treatment device has a supply of medication and a means for delivering the medication to the patient using a control algorithm and a sensing device. The control algorithm is coupled to the medical device. The sensing device is coupled to the control algorithm and the sensing device sends a signal to the control algorithm. The control algorithm processes the signal received from the sensing device and develops a feedback control based on a result of processing the signal to determine whether medication should be delivered from the medical treatment device to the patient. The feedback control is provided to the medical treatment device to control the delivery of the medical treatment to the patient. The remote controller for the device is disposed at a second location remote from the first location. The remote controller has an input device to control operation of the control algorithm." (U.S. Pat. No. 6,689,091 titled "Medical apparatus with remote control.")

"The present invention provides systems and methods for remote control and/or wireless (re-)programming of drug pump devices. In various embodiments, a smartphone or other wireless handheld device is used to send control commands and/or drug-delivery protocols to a wireless receiver of the drug pump device, e.g., via a Wi-Fi, Bluetooth, or near-field communication link. The smartphone may be equipped with a dongle to provide security and/or flexibility in the choice of the data-transfer protocol. Further, the smartphone may store a special software application that enables interaction with the user, and which may have security features that prevent unauthorized operation. In some embodiments, communication between the drug pump device and smartphone is bi-directional; for example, the drug pump device may transmit information about the device status to the smartphone, which may adjust device operation based thereon. Advantageously, remote control of the drug pump device eliminates the need to physically access the device to control its operation. In addition, the use of a smartphone enables a clinician to reprogram and adjust pump operation remotely, e.g., by sending a new drug delivery protocol via the smartphone to the pump device." (U.S. Pat. No. 8,285,328 titled "Remote-controlled drug pump devices.")

"It is the purpose of the present invention to provide a diagnostic system, which can convert conventional hospital-based central telemetry and bard wired monitoring systems and portable home systems to provide processor based recognition of airway instability through the recognition of patterns of closely spaced reciprocations and/or events induced by apneas and/or hypopneas both in real time and in overnight interpretive format and which can automatically lock-out narcotic infusion upon recognition of patterns of instability." (U.S. Pat. No. 9,031,793 titled "Centralized hospital monitoring system for automatically detecting upper airway instability and for preventing and aborting adverse drug reactions.")

"In an embodiment of the current invention, a method of adjusting a treatment protocol includes determining that an adjustment should occur, alerting a patient to a proposed adjustment in the treatment protocol by providing an alert signal, and performing the proposed operation only if the patient approves the adjustment or a time limit is reached." (U.S. Pat. No. 9,649,439 titled, "Systems and methods for facilitating patient-based adjustment of drug infusion.")

"A care system in accordance with the invention includes at least one patient health monitor which monitors a patient's physiological condition integrated with a drug delivery controller supplying an analgesic or other drug to the patient. A programmable, microprocessor-based electronic controller compares the electronic feedback signals generated from the patient health monitor and representing the patient's actual physiological condition with a stored safety data set reflecting safe and undesirable parameters of at least one patient physiological condition and manages the application or delivery of the drug to the patient in accord with that comparison. In a preferred embodiment, the management of drug delivery is affected by the electronic controller via conservative, decision-making software accessing the stored safety data set." (U.S. Pat. No. 8,882,703 titled "Drug delivery in association with medical or surgical procedures.")

"A system and method for remote monitoring and/or management of infusion therapies. A user can monitor and manage server-connected pumps at a remote location, such as a computer or PDA. Pumps located at an institution, such as a hospital or patients' home, are connected, for example, via the Internet to a server that includes a database of information. A user can operate the pump, from a remote location, by using an interface displayed at the remote location. The operator can manage pump operations by use of the interface. In this context, the user can turn the pump on and off, select infusion rates, dose amounts, etc. all from the convenience of the remote location." (US Publication Number 20080154177A1 titled "System and method for remote monitoring and/or management of infusion therapies")

Therefore, there is a need for systems and methods for infusion of a drug and monitoring a patient's physiological condition and drug infusion system parameters to adjust session time dynamically based on the physiological condition of the patient.

SUMMARY

An embodiment relates to a system, comprising, a timer module comprising a timer configured to set a time for a session, an infusion module comprising an infusing device configured for administering a drug to a patient, a patient monitoring module comprising a first sensor configured for monitoring a physiological condition of the patient, a drug monitoring and control module comprising a second sensor configured for monitoring a drug delivery to the patient, an alarm generating module comprising signal generator that generates an indication signal when a value of the physiological condition is outside a predefined threshold, and wherein the time for the session is dynamically adjusted during the session; and wherein the drug delivery is dynamically adjusted during the session.

In an embodiment, the system further comprises a remote monitoring system for remotely monitoring the system.

According to an embodiment, the timer module is configured to monitor the time for the session continuously.

According to an embodiment, the time for the session comprises stages of therapy, wherein the stages of therapy are monitored, and a stage time and a stage drug delivery rate are configured to be adjusted based on the physiological condition of the patient.

According to an embodiment, the time for the session is a predetermined value based on a health condition of the patient.

According to an embodiment, the session comprises at least one of a psychotherapy session, a massage session, a chemotherapy session, and a surgery.

According to an embodiment, the infusing device is configured to receive at least a vial comprising the drug, wherein the vial has a unique identifier.

According to an embodiment, the infusing device is configured to receive a plurality of vials comprising the drug and a second drug, wherein each of the plurality of vials has a unique identifier.

According to an embodiment, the drug is a curing drug, and a second drug to counter a side effect of the drug.

According to an embodiment, the drug is a psychotherapy drug or psychedelic drug comprising ketamine.

According to an embodiment, the infusing device is configured to administer the plurality of drugs as per a dosage rule and in a specific sequence.

According to an embodiment, the specific sequence is predetermined or determined dynamically during the session.

According to an embodiment, administering the drug is continuous and automated.

According to an embodiment, the patient monitoring module comprises a monitoring system to monitor at least a parameter related to the patient, wherein the parameter comprises at least one selected from a brain activity, a responsiveness, a seizure, a vomiting, a breathing rate, a heart rate, a heart activity, a body temperature, a blood pressure, a pupil color, a pupil dilation, a pupil constriction, a sound made by the patient, a lip color, a fingertip color, a first response to an outside stimuli, a second response to a loud noise, a shaking of a body part, and a skin color.

According to an embodiment, monitoring the brain activity comprises an electroencephalogram (EEG) configured to measure the brain activity and identifying a distinctive brain activity pattern that marks a loss of consciousness or a hallucination, wherein the electroencephalogram (EEG) is configured to detect electrical activity of the brain of the patient.

According to an embodiment, the first sensor comprises at least one of an electrocardiogram (ECG) electrode, a respiratory sensor, a sweat sensor, and a temperature sensor.

According to an embodiment, at least one of the pupil color, the pupil dilation, the pupil constriction is monitored using an eye mask comprising sensors.

According to an embodiment, the patient monitoring module is a wearable jacket.

According to an embodiment, the patient monitoring module is portable and is configured to be attached to a surface where the patient is supported.

According to an embodiment, the patient monitoring module is configured to be integrated to a surface where the patient is supported.

According to an embodiment, the first sensor is wearable.

According to an embodiment, the first sensor is wearable and flexible to contour around a body part of the patient.

According to an embodiment, the physiological condition comprises at least one of a heart rate, a respiratory rate, a blood pressure, a perspiration level, and a body temperature of the patient.

According to an embodiment, the patient monitoring module is further configured to store monitoring data of the patient to a database.

According to an embodiment, the drug monitoring and control module is configured to monitor a quantity of the drug and a rate of drug delivery to the patient.

According to an embodiment, the drug monitoring and control module is further configured to store data of the quantity of the drug delivered to the patient to a database.

According to an embodiment, the drug monitoring and control module is further configured to store data of the rate of drug delivery to a database.

According to an embodiment, the indicating signal is a light signal.

According to an embodiment, the indicating signal is a light signal of a color and is configured for a specific message.

According to an embodiment, the indication signal is configured to be a light cue at least in one of a room, a door, a chair, a personal wearable device, and a computer.

According to an embodiment, the predefined threshold is configured for the patient based on historic health record and current physiological condition.

According to an embodiment, the dynamically adjusting the time for the session and the drug delivery is based on feedback from the first sensor and the second sensor.

According to an embodiment, the system further comprises a push notification module configured to deliver automated message notifications to the patient and an attendee.

According to an embodiment, the system further comprises an authentication module configured to check credentials of a user from a database of authorized users stored in a memory.

According to an embodiment, the system is further configured to generate and execute a dosage rule based on the physiological condition of the patient.

According to an embodiment, the system is further configured to generate and execute a sequence of drugs and a dosage rule based on the physiological condition of the patient.

According to an embodiment, the system is further configured to record feedback of the patient.

According to an embodiment, the system further comprises a pre-recording module configured to create individual distributions of the physiological condition of the patient to identify the predefined threshold for a monitoring period.

According to an embodiment, the patient monitoring module further comprises artificial intelligent techniques to determine the drug delivery based on the physiological condition of the patient during the session.

According to an embodiment, the patient monitoring module further comprises artificial intelligent techniques to determine a quantity of the drug and a drug rate based on the physiological condition of the patient during the session.

According to an embodiment, the physiological condition is configured to be assessed based on time trend.

According to an embodiment, the system is configured to provide situational awareness about the patient.

According to an embodiment, the system is configurable to be implemented with a plurality of patients in the session.

According to an embodiment, the system is configurable for the plurality of sessions for the plurality of patients simultaneously.

According to an embodiment, the patient monitoring module is configured to monitor the patient continuously.

According to an embodiment, the drug monitoring and control module is configured to monitor the drug delivery to the patient continuously.

According to an embodiment, the system is integrated with a chair on which the patient is supported.

According to an embodiment, the system is integrated with a bed on which the patient is supported.

According to an embodiment, the system further comprises a first authentication module for the session.

According to an embodiment, the system further comprises a second authentication module for the patient.

According to an embodiment, the system further comprises predicting a risk of the drug.

According to an embodiment, the system further comprises generating a corrective action towards a predicted risk.

According to an embodiment, the system further comprises a cybersecurity module for securing first data of the patient and second data of the session.

According to an embodiment, the first data and the second data are secured.

According to an embodiment, data of the patient is accessible by a drug dispensing system for dispensing a drug.

Another embodiment related to a method, comprising the steps of, setting a time for a session, administering a drug to a patient by an automated infusion module, monitoring a physiological condition in the patient, monitoring a quantity of the drug and a rate of drug delivery to the patient, analyzing the physiological condition, the quantity of the drug, and the rate of drug delivery, generating an indication signal when a value of at least one of the physiological condition, the quantity of the drug, and the rate of drug delivery exceeds a predefined threshold, controlling a quantity of the drug and a rate of drug delivery to the patient based on the physiological condition, changing the time for the session based on the physiological condition, and wherein the method is configured for remote monitoring of the patient and the session.

Another embodiment relate to a system, comprising, a timer module comprising a timer configured to set a time for a session, an infusion module comprising an infusing device for administering a drug to a patient, a patient monitoring module comprising a first sensor configured for monitoring of a physiological condition in the patient, a drug monitoring module comprising a second sensor configured for monitoring of quantity of the drug and a rate of drug delivery to the patient, a drug control module comprising an actuator configured to control the rate of drug delivery, an alarm generating module comprising an indication signal configured to generate an alarm when a value of at least one of the physiological condition, the quantity of the drug and the rate of drug delivery exceeds a predefined threshold and herein the system is configured for remote monitoring of the patient; and wherein the system is configured for a remote control of the quantity of the drug and a rate of drug delivery.

Another embodiment relates to a system, comprising a timer module comprising a timer configured to a time for a session, an automated infusion module comprising a drug infusing device for administering a drug to a patient, a monitoring module comprising, a first sensor configured for monitoring of a physiological condition in the patient, a second sensor configured for monitoring of quantity of the drug and a rate of drug delivery to the patient, a third sensor configured for monitoring of a patient movement, a fourth sensor configured for monitoring of an eye activity, a fifth sensor configured to monitor a brain activity, an alarm generating module comprising an indication signal configured to generate an alarm when a value of at least one of the physiological condition, the time of the session, the quantity of the drug and the rate of drug delivery exceeds a predefined threshold and wherein the time for the session is dynamically adjusted based on at least one of the physiological condition, the eye activity, and the brain activity, and wherein the system is configured for remote monitoring.

In an embodiment, the cyber security module further comprises an information security management module providing isolation between the system and the server.

In an embodiment, the information security management module is operable to, receive data from at least one of the user interface, the infusion module, the patient monitoring module, the drug monitoring and control module, the alarm generating module, and the database, exchange a security key at a start of the communication between the communication module and the server, receive the security key from the server, authenticate an identity of the server by verifying the security key, analyze the security key for a potential cyber security threat, negotiate an encryption key between the communication module and the server, encrypt the data; and transmit the encrypted data to the server when no cyber security threat is detected.

In an embodiment, the information security management module is operable to exchange a security key at a start of the communication between the communication module and the server, receive the security key from the server, authenticate an identity of the server by verifying the security key, analyze the security key for a potential cyber security threat, negotiate an encryption key between the system and the server, receive encrypted data from the server, decrypt the encrypted data, perform an integrity check of the decrypted data and transmit the decrypted data to at least one of the user interface, the infusion module, the patient monitoring module, the drug monitoring and control module, the alarm generating module and the database through the communication module when no cyber security threat is detected.

In an embodiment, the information security management module is configured to raise an alarm when the cyber security threat is detected.

In an embodiment, the information security management module is configured to raise an alarm when the cyber security threat is detected.

In an embodiment, the information security management module is configured to discard the encrypted data received if the integrity check of the encrypted data fails.

In an embodiment, the information security management module is configured to check the integrity of the encrypted data by checking accuracy, consistency, and any possible data loss during the communication through the communication module.

In an embodiment, the information security management module is configured to perform asynchronous authentication and validation of the communication between the communication module and the server.

In an embodiment, a perimeter network provides an extra layer of protection.

In an embodiment, the perimeter network protects the system from a cyber security threat by using a plurality of firewalls.

DETAILED DESCRIPTION

Definitions and General Techniques

Figure 1:
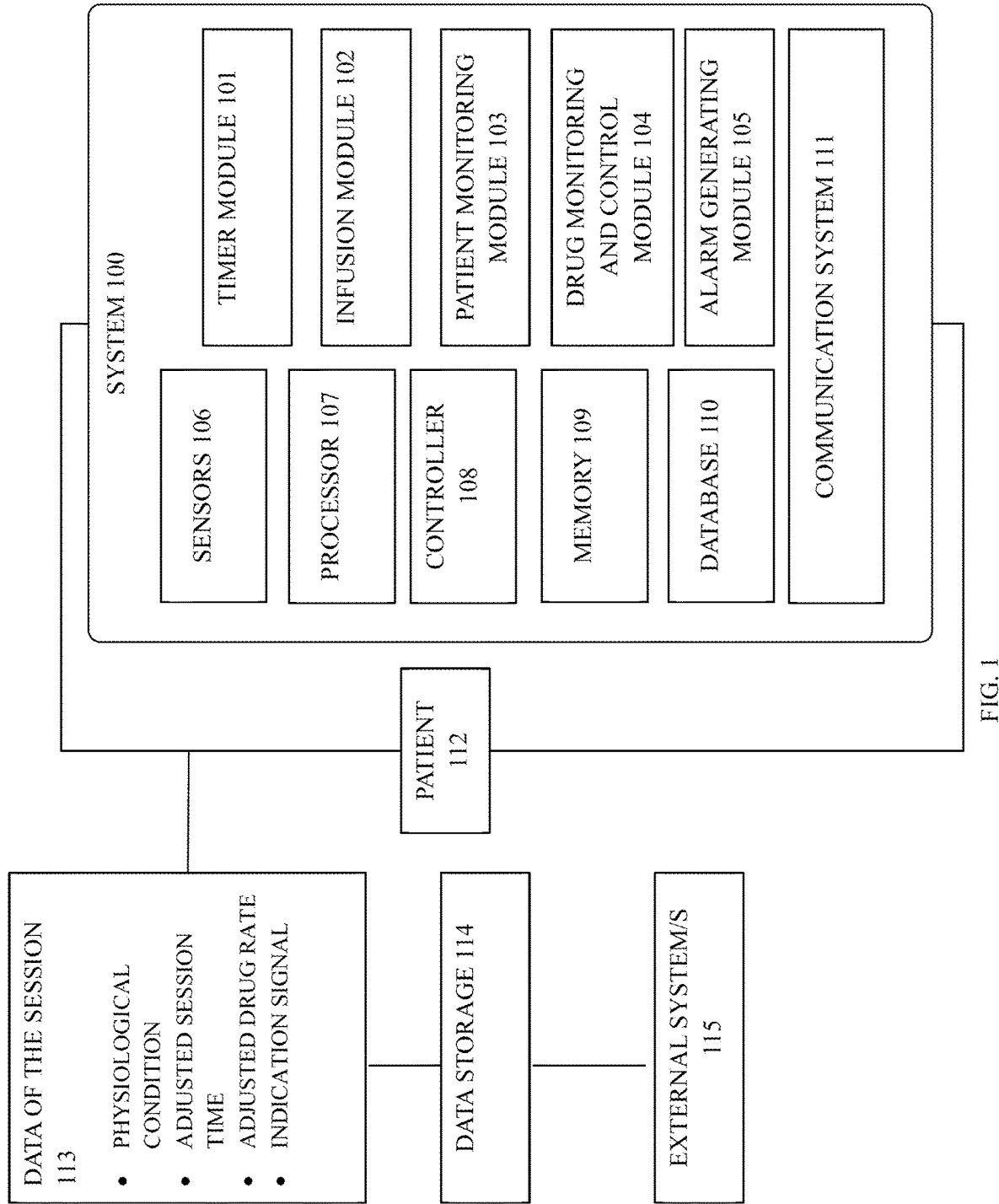
FIG. 1 shows a drug infusion and monitoring system according to an embodiment of the invention.

For simplicity and clarity of illustration, the drawing figures illustrate the general manner of construction. Descriptions and details of well-known features and techniques may be omitted to avoid unnecessarily obscuring the present disclosure. The dimensions of some of the elements in the figures may be exaggerated relative to other elements to help improve understanding of embodiments of the present disclosure. The same reference numeral, if any, in different figures denotes the same elements.

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only and is not intended to be limiting. Unless defined otherwise, all technical and scientific terms used herein have the same meaning as commonly understood by one with ordinary skill in the art to which this disclosure belongs.

The articles "a" and "an" are used herein to refer to one or to more than one (i.e., to at least one) of the grammatical object of the article. By way of example, "an element" means one element or more than one element.

The terms "first," "second," "third," and the like in the description and in the claims, if any, are used for distinguishing between similar elements and not necessarily for describing a particular sequence or chronological order. It is to be understood that the terms so used are interchangeable under appropriate circumstances such that the embodiments described herein are, for example, capable of operation in sequences other than those illustrated or otherwise described herein. Furthermore, the terms "include," "have," and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

No element act, or instruction used herein should be construed as critical or essential unless explicitly described as such. Furthermore, as used herein, the term "set" is intended to include items (e.g., related items, unrelated items, a combination of related items and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The terms "couple," "coupled", "couples," "coupling," and the like should be broadly understood and refer to as connecting two or more elements mechanically, electrically, and/or otherwise. Two or more electrical elements may be electrically coupled together, but not be mechanically or otherwise coupled together. Coupling may be for any length of time, e.g., permanent, or semi-permanent or only for an instant. "Electrical coupling" includes electrical coupling of all types. The absence of the word "removably", "removable", and the like near the word "coupled," and the like does not mean that the coupling, etc. in question is or is not removable.

As defined herein, two or more elements or modules are "integral" or "integrated" if they operate functionally together. As defined herein, two or more elements are "non-integral" if each element can operate functionally independently.

As defined herein, "real-time" can, in some embodiments, be defined with respect to operations carried out as soon as possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

As used herein, the term "component" is intended to be broadly construed as hardware, firmware, and/or a combination of hardware and software.

As used herein, the term "approximately" can mean within a specified or unspecified range of the specified or unspecified stated value. In some embodiments, "approximately" can mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All variations which come within the meaning and range of equivalency of the claims are to be embraced within their scope.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products i.e., one or more modules of computer program instructions encoded on a computer-readable medium for execution by, or to control the operation of, data processing apparatus. The computer-readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example, a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal (e.g., a machine-generated electrical, optical, or electromagnetic signal) that is generated to encode information for transmission to a suitable receiver apparatus.

The actual specialized control hardware or software code used to implement these systems and/or methods is not limiting of the implementations. Thus, the operation and behavior of the systems and/or methods described herein without reference to specific software code, it being understood that any software and any hardware can be designed to implement the systems and/or methods based on the description herein.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any appropriate kind of digital computer. Generally, a processor will receive instructions and data from a read-only memory or a random-access memory or both. Elements of a computer can include a processor for performing instructions and one or more memory devices for storing instructions and data. Generally, a computer will also include, or be operatively coupled to receive data, transfer data or both, to/from one or more mass storage devices for storing data e.g., magnetic disks, magneto optical disks, optical disks, or solid-state disks. However, a computer need not have such devices. Moreover, a computer may be embedded in another device, e.g., a mobile telephone, a personal digital assistant (PDA), a mobile audio player, a Global Positioning System (GPS) receiver, etc. Computer-readable media suitable for storing computer program instructions and data include all forms of non-volatile memory, media and memory devices, including, by way of example, semiconductor memory devices (e.g., Erasable Programmable Read-Only Memory (EPROM), Electronically Erasable Programmable Read-Only Memory (EEPROM), and flash memory devices), magnetic disks (e.g., internal hard disks or removable disks), magneto optical disks (e.g. Compact Disc Read-Only Memory (CD ROM) disks, Digital Versatile Disk-Read-Only Memory (DVD-ROM) disks) and solid-state disks. The processor and the memory may be supplemented by, or incorporated in, special purpose logic circuitry.

To provide for interaction with a user, implementations may be realized on a computer having a display device, e.g., a Cathode Ray Tube (CRT) or Liquid Crystal Display (LCD) monitor, for displaying information to the user, and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back-end component, e.g., a data server, or that includes a middleware component, e.g., an application server, or that includes a front-end component, e.g., a client computer having a graphical user interface or a Web browser through which a user may interact with an implementation, or any appropriate combination of one or more such back-end, middleware, or front-end components. The components of the system may be interconnected by any appropriate form or medium of digital data communication, e.g., a communication network. Examples of communication networks include a Local Area Network (LAN) and a Wide Area Network (WAN), e.g., Intranet and Internet.

The computing system may include clients and servers. A client and server are generally remote from each other and typically interact through a communication network. The relationship of the client and server arises by virtue of computer programs running on the respective computers and having a client-server relationship to each other.

Embodiments of the present invention may comprise or utilize a special purpose or general purpose computer including computer hardware. Embodiments within the scope of the present invention may also include physical and other computer-readable media for carrying or storing computer-executable instructions and/or data structures. Such computer-readable media can be any media that can be accessed by a general purpose or special purpose computer system. Computer-readable media that store computer-executable instructions are physical storage media. Computer-readable media that carry computer-executable instructions are transmission media. Thus, by way of example and not limitation, embodiments of the invention can comprise at least two distinctly different kinds of computer-readable media: physical computer-readable storage media and transmission computer-readable media.

In addition, it will be appreciated that the various operations, processes, and methods disclosed herein may be embodied in a non-transitory machine-readable medium and/or a system. Accordingly, the specification and drawings are to be regarded in an illustrative rather than a restrictive sense.

Physical computer-readable storage media includes RAM, ROM, EEPROM, CD-ROM or other optical disk storage (such as CDs, DVDs, etc.), magnetic disk storage or other magnetic storage devices, solid-state disks or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry desired program code means in the form of computer-executable instructions or data structures, and which can be accessed by a general purpose or special purpose computer. Combinations of the above, that enable the transport of electronic data between computer systems and/or modules and/or other electronic devices, are also included within the scope of computer-readable media.

Further, upon reaching various computer system components, program code in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (NIC), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions may be, for example, binary, intermediate format instructions such as assembly language, or even source code. Although the subject matter has been described in language specific to structural features and/or methodological acts, it is to be understood that the subject matter defined in the claims is not necessarily limited to the described features or acts described. Rather, the described features and acts are disclosed as example forms of implementing the claims.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order to achieve desired results, this should not be understood as requiring that such operations be performed in the particular order shown or in sequential order or that all illustrated operations be performed, to achieve desirable results. In certain circumstances, multitasking and parallel processing may be advantageous. Moreover, the separation of various system components in the implementations should not be understood as requiring such separation in all implementations, and it should be understood that the described program components and systems may generally be integrated together in a single software product or packaged into multiple software products.

Even though particular combinations of features are recited in the claims and/or disclosed in the specification, these combinations are not intended to limit the disclosure of possible implementations. Other implementations are within the scope of the following claims. For example, the actions recited in the claims may be performed in a different order and still achieve desirable results. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

Further, the methods may be practiced by a computer system including one or more processors and computer-readable media such as computer memory. In particular, the computer memory may store computer-executable instructions that when executed by one or more processors cause various functions to be performed such as the acts recited in the embodiments.

The disclosure provides illustration and description but is not intended to be exhaustive or to limit the implementations to the precise form disclosed. Modifications and variations are possible in light of the above disclosure or may be acquired from practice of the implementations.

Those skilled in the art will appreciate that the invention may be practiced in network computing environments with many types of computer system configurations including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, etc. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

As used herein, the term "API" stands for Application Programming Interface. It is an interface that defines interactions between multiple software applications or mixed hardware-software intermediaries. It defines the kinds of calls or requests that can be made, how to make them, the data formats that should be used, the conventions to follow, etc. It can also provide extension mechanisms so that users can extend existing functionality in various ways and to varying degrees. An API can be entirely custom, specific to a component, or designed based on an industry-standard to ensure interoperability. Through information hiding, APIs enable modularity, allowing users to use the interface independently of the implementation. Web APIs are now the most common meaning of the term API. There are also APIs for programming languages, software libraries, computer operating systems, and computer hardware.

The APIs may be dynamically derived by the network. In other implementations, the APIs may be derived from API records that are stored by the network. Additionally, when new APIs are derived for a particular network service, the APIs may be recorded in case a similar network service request (e.g., from another user) is received, in which case the record may be promptly used to determine the appropriate API, or set of APIs, for the requested network service.

The API request (e.g., for a name, an ID, or another type of information in the request) may correspond to network interactions, communications, events, etc., that are to occur in order to provide the network service. The chain of network interactions, communications, events, etc., may be stored in libraries/repositories of the Software Defined Networking (SDN). APIs may be derived based on the characteristics of each of the interactions, communications, events, etc., being mapped to characteristics of APIs (also stored in libraries/repositories of the SDN architecture).

Secure Socket Layer (SSL) and Transport Layer Security (TLS), the successor to SSL, are cryptographic protocols that may be used by networking switches to secure data communications over a wireless network.

As used herein, the term "logging" is the process of collecting and storing data over a period in order to analyze specific trends or record the data-based events/actions of a system, network, or Information Technology (IT) environment. It enables the tracking of all interactions through which data, files or applications are stored, accessed, or modified on a storage device or application.

As used herein, the term "unauthorized access" is when someone gains access to a website, program, server, service, or other system using someone else's account or other methods. For example, if someone kept guessing a password or username for an account that was not theirs until they gained access, it is considered unauthorized access.

As used herein, the term "data maintenance" is the process of organizing and curating data according to industry needs. Properly maintaining and caring for data is essential to ensuring that data remains accessible and usable for its intended purposes.

As used herein, the term "IoT" stands for Internet of Things which describes the network of physical objects "things" or objects that are embedded with sensors, software, and other technologies for the purpose of connecting and exchanging data with other devices and systems over the internet.

As used herein, the term "machine learning" refers to algorithms that give a computer the ability to learn without being explicitly programmed including algorithms that learn from and make predictions about data. Machine learning algorithms include, but are not limited to, decision tree learning, artificial neural networks (ANN) (also referred to herein as a "neural net"), deep learning neural network, support vector machines, rules-based machine learning, random forest, etc. For the purposes of clarity, algorithms such as linear regression or logistic regression can be used as part of a machine learning process. However, it is understood that using linear regression or another algorithm as part of a machine learning process is distinct from performing a statistical analysis such as regression with a spreadsheet program. The machine learning process can continually learn and adjust the classifier as new data becomes available and does not rely on explicit or rules-based programming.

As used herein, the term "data mining" is a process used to turn raw data into useful information.

As used herein, the term "data acquisition" is the process of sampling signals that measure real world physical conditions and converting the resulting samples into digital numeric values that can be manipulated by a computer. Data acquisition systems typically convert analog waveforms into digital values for processing. The components of data acquisition systems include sensors to convert physical parameters to electrical signals, signal conditioning circuitry to convert sensor signals into a form that can be converted to digital values, and analog-to-digital converters to convert conditioned sensor signals to digital values. Stand-alone data acquisition systems are often called data loggers.

As used herein, the term "dashboard" is a type of interface that visualizes particular Key Performance Indicators (KPIs) for a specific goal or process. It is based on data visualization and infographics.

As used herein, a "database" is a collection of information that is organized so that it can be easily accessed, managed, and updated. Computer databases typically contain aggregations of data records or files.

As used herein, the term "data set" (or "dataset") is a collection of data. In the case of tabular data, a data set corresponds to one or more database tables, where every column of a table represents a particular variable, and each row corresponds to a given record of the data set in question. The data set lists values for each of the variables, such as height and weight of an object, for each member of the data set. Each value is known as a datum. Data sets can also consist of a collection of documents or files.

The following terms and phrases, unless otherwise indicated, shall be understood to have the following meanings.

The term "authentication module" as used herein refers to a module which performs user authentication and verifies the identity of a user attempting to gain access to a network or computing resource by authorizing a human-to-machine transfer of credentials during interactions on a network to confirm a user's authenticity. Authentication module keeps unauthorized users from accessing sensitive information. It can refer to a password-based authentication, certificate-based authentication, biometric authentication, token-based authentication, a multi-factor authentication, etc.

The term "brain activity" as used herein refers to neural activity and when captured using measuring devices such as functional Magnetic Resonance Imaging (fMRI), magnetoencephalography (MEG) and electroencephalography (EEG), brain state can be analyzed which reflects engagement, motivation, or drowsiness over longer periods (hours to days), etc. Brain signals or activity may be recorded shortly after the onset of visual, physical, or audio stimuli.

The term "comfort" as used herein refers to a state of physical and/or mental ease and freedom from pain or constraint. It is usually measured by comparing movement or non-movement of the patient's body part when the patient is at ease and in comfort to that of when he is in pain or discomfort.

The term "continuous monitoring" as used herein refers to the practice of monitoring potential or interested parameters. These services pair well with periodic checks and are typically conducted to notify the concerned person of any changes to the monitored parameter/s in real-time. Continuous monitoring is performed in conjunction with alarm monitoring to trigger alarms when critical systems exceed defined performance thresholds.

The term "dosage" as used herein refers to an amount of drug or drug concentration taken at any one time or within a session at a prescribed drug delivery rate. A dose is a measured quantity of a medicine, nutrient, or pathogen which is delivered as a unit. The greater the quantity delivered, the larger the dose. Doses are most commonly measured for compounds in medicine. The term is usually applied to the quantity of a drug or other agent administered for therapeutic purposes but may be used to describe any case where a substance is introduced to the body.

The term "drug" as used herein refers to any substance (other than food) that is used to prevent, diagnose, treat, enhance, inhibit, or relieve symptoms of a disease or abnormal condition. Some drugs may be used for psychedelic reasons. Some drugs may inhibit memory (for example, ketamine) for a period or enhance unconscious activity, to reduce hallucinations. It includes psilocybin and *cannabis* compounds.

The term "drug delivery" as used herein refers to a method or process of administering a pharmaceutical compound to achieve a therapeutic effect in humans or animals. In the drug delivery process, rate of the drug delivery, and the amount of drug delivered are monitored along with other parameters.

The term, "drug delivery system" as used herein refers to a system that controls a rate at which a drug is released. The drug delivery system also comprises a system that controls a location in the body where it is released. Some systems can control both location of drug delivery and the rate at which drug is released.

The term "drug monitoring module" as used herein refers to a module where drug related parameters are monitored. These parameters can be drug dosage, drug delivery rate of the pump or infusion device. It also includes drug identification number, drug name, drug sequence, manufacturing date, expiration date, etc. The monitoring of drugs may involve measuring drug concentrations in plasma, serum, or blood. This information may be used to individualize dosage so that drug concentrations can be maintained within a target range.

The term "dynamically" as used herein refers to a way that is continuously changing or developing as a situation changes. It is also characterized by continuous change, activity, or progress.

The term "eye activity" as used herein refers to a point of gaze (where one is looking), a motion of an eye relative to the head, eye position, size of pupil, pupil dilation or constriction, blinking patterns, visual attention, etc. An eye tracker is a device for measuring eye positions and eye movement.

The term "feedback" as used herein refers to when output of a system is routed back as inputs as part of a chain of cause-and-effect that forms a circuit or loop. The system can then be said to feed back into itself. A feedback mechanism is a loop system in which the system responds to perturbation either in the same direction (positive feedback) or in the opposite direction (negative feedback). In a system, a feedback mechanism involves a process, a signal, or a mechanism that tends to initiate (or accelerate) or to inhibit (or slow down) a process. As an example, when a drug infusion slows down the heart rate or drops a body temperature, the drug delivery rate is reduced or stopped to improve the patient's physiological condition.

The term "gesture" as used herein refers to a user action that expresses an intended idea, action, meaning, result, and/or outcome. The user action can include manipulating a device (e.g., opening or closing a device, changing a device orientation, moving a trackball or wheel, etc.), movement of a body part in relation to the device or in relation to a reference point, movement of an implement or tool in relation to the device, audio inputs, etc. A gesture may be made on a device (such as on the screen) or with the device to interact with the device.

The term "gesture capture" as used herein refers to a sense or otherwise a detection of an instance and/or type of user gesture. The gesture capture can be received by sensors in three-dimensional space. Further, the gesture capture can occur in one or more areas of a screen, for example, on a touch-sensitive display or a gesture capture region. A gesture region can be on the display, where it may be referred to as a touch sensitive display, or off the display, where it may be referred to as a gesture capture area.

The term "health record" as used herein refers to a compilation of pertinent facts of an individual's health history, including all past and present medical conditions, illnesses, and treatments, with emphasis on the specific events affecting the patient during the current episode of care. The information documented in the health record is created or maintained by all healthcare professionals providing care and is used for continuity of care. The data is often confidential. An Electronic Health Record (EHR) is an electronic version of a patient's medical history, which is maintained by the provider over time, and may include all key administrative clinical data relevant to that person's care under a particular provider, including demographics, progress notes, problems, medications, vital signs, past medical history, immunizations, laboratory data and radiology reports.

The term "in communication with" as used herein, refers to any coupling, connection, or interaction using electrical signals to exchange information or data, using any system, hardware, software, protocol, or format, regardless of whether the exchange occurs wirelessly or over a wired connection.

The term "infusion device" as used herein refers to a medical device that delivers fluids, such as nutrients and medications, into a patient's body in controlled amounts. An infusion pump has a built-in software interface and can be programmed to a rate and duration of fluid delivery. Infusion pumps can deliver nutrients or medications, such as insulin or other hormones, antibiotics, chemotherapy drugs, and pain relievers. They may be stationary or ambulatory infusion pumps which are designed to be portable or wearable.

The term "Infusion module" as used herein refers to a module comprising an infusion pump that continuously or intermittently delivers fluids, medications, blood and blood products to a patient or a user. It may refer to the plurality of infusion devices managed by a software program and a control unit. It may refer to a module comprising one or more software programs and one or more control units, or it may refer to a module comprising a plurality of software programs and a plurality of control units.

The term "infusion therapy" as used herein refers to medication or fluids administered through a needle or catheter. It is a way of delivering medication that cannot be taken orally, or that needs to be dispensed at a controlled pace. It is a method of putting fluids, including drugs, into the bloodstream. Also referred to as intravenous infusion. It includes vitamin infusion as well.

The term "infusion therapy session" as used herein refers to a session in which treatment of a patient is provided with intravenously applied infusion solutions in order to enable a patient's recovery or to improve from his illness.

The term "psychedelic drug" as used herein refers to a drug or a medication primarily used as a treatment for depression and an antidote to suicidal thoughts. It is also used for induction and maintenance of anesthesia. It induces dissociative anesthesia, a trance-like state providing pain relief, sedation, and amnesia. It may, in general, also refer to any drug that provides anti depression effects, for example, Ketamine, Zoloft®.

The term "module" as used herein refers to a set of standardized or independent units/parts that can be used to construct a more complex structure. A module is a combination of both hardware units and software programs to control hardware units. It refers to any known or later developed hardware, software, firmware, artificial intelligence, fuzzy logic, or combination of hardware and software that is capable of performing the functionality associated with that element.

The term "monitoring" as used herein refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" can include monitoring of blood gas levels, blood hydration, blood flow, and metabolite/electrolyte levels. For example, the term patient monitoring as used herein refers to a system that enables monitoring of a patient's health or physiological condition. Patient monitoring can be wireless, portable, and remote. As a more specific example, a noninvasive health and environmental monitor system/network may support a therapeutic drug study by noninvasively monitoring the real-time drug dosage in the body through multiwavelength pulse oximetry, monitoring core body temperature through thermal sensing of the tympanic membrane, and monitoring environments which may positively or negatively affect the quality of the drug therapy. Patient monitoring systems are collections of machines or equipment used to constantly monitor patients through various vital signs and warning systems to detect and record changes in patient wellbeing.

The term "nurse" or "attendant" as used herein refers to a person who is attending or monitoring the patient.

The term "patient" or "subject" or "user" as used herein refers to a person receiving or registered to receive medical treatment. A patient is also referred to as a user as he receives treatment using the therapy system.

The term "physiological condition" as used herein refers to a condition or state of the body or bodily functions. It is also referred to as a physiological state. Examples include but not limited to asphyxia, consciousness, alertness, acapnia, hypercapnia, hypothermia, hyperthermia, upset, cryptobiosis, good health, myasthenia, atherosclerosis, myocardial infarction, angina pectoris, arrhythmias (irregular heartbeat), chronic heart failure, blood pressure, glucose or blood sugar, temperature, drowsiness, hallucinations, slow breathing, dry mouth, anxiety, vomiting, confusion, drowsiness, slurred speech, rambling speech, lack of coordination, mood changes, involuntary eye movement, dizziness, alertness, restlessness, dilated pupils, nasal congestion, behavior changes, chills, sweating, loss of memory, teeth clenching, coordination problems, impulsive behavior, pain sensitivity, tremors, rashes, euphoria, sense of pain, etc. Some signs may be directly measured, for example, heart rate and some may be indirectly measured, for example, measuring brain activity to analyze the state of consciousness. In the embodiments herein, the term "physiological" is intended to be used broadly, covering both physical and psychological characteristics of or from the body of an organism.

The term "pre-recording module" as used herein refers to a module where a pre-recorded data specific to the patient is fed into the system or where a pre-recording of patient related data is measured in real time and fed into the system. Feeding of the data to the system can be either manual, wired transfer or wireless transfer of data. The pre-recording module may be interfaced with the system and can automatically read the patient data and store it into the system to reflect the patient related data.

The term "profile" relates to a summary of noteworthy characteristics and/or habits of an individual or group of individuals. These characteristics may be physiological (health-related), environmental, statistical, demographical, behavioral, and the like. Age, location, gender, sex, weight, ethnicity, and/or height may be included in a profile. The profile and the aforementioned characteristics and/or habits can be used in the context of social media and further information in the interactions within a social media network can be extracted to form a part of a profile as well. Additionally, a profile may reference the buying and/or spending habits of an individual or group and can further include a credit rating. Profiles may be utilized in making predictions about an individual or group. It can refer to any data structure, data store, and/or database that includes one or more items of information associated with a system, a device (e.g., a mobile device, laptop, mobile phone, etc.), or a person.

The term "quantity of drug" as used herein refers to dosage of the drug administered to a subject at a given time or over a cumulative period of time.

The term "rate of drug delivery" as used herein refers to a rate at which a drug is released.

The term "remote monitoring" as used herein refers to a standard specification that facilitates the monitoring of network operational activities through the use of remote devices known as monitors or probes.

The term "sensor" as used herein refers to a device that detects or measures a physical property and enables the recording, presentation and/or system response to such detection or measurement using processor and optionally memory. A sensor and processor can take one form of information and convert such information into another form, typically having more usefulness than the original form. For example, a sensor may collect raw physiological or environmental data from various sensors and process this data into a meaningful assessment, such as pulse rate, blood pressure, or air quality using a processor. A "sensor" herein can also collect or harvest acoustical data for biometric analysis (by a processor) or for digital or analog voice communications. A "sensor" can include any one or more of a physiological sensors (e.g., blood pressure, heartbeat, etc.), a biometric sensor (e.g., a heart signature, a fingerprint, etc.), an environmental sensor (e.g., temperature, particles, chemistry, etc.), a neurological sensor (e.g., brainwaves, EEG, etc.), or an acoustic sensor (e.g., sound pressure level, voice recognition, sound recognition, etc.) among others. A variety of microprocessors or other processors may be used herein. Although a single processor or sensor may be represented in the figures, it should be understood that the various processing and sensing functions can be distributed among multiple processors and sensors operate cooperatively or execute on a single processor and sensor arrangement that includes transceivers and numerous other functions as further described herein. A sensor is a device that measures physical input from its environment and converts it into data that can be interpreted by either a human or a machine. Most sensors are electronic (the data is converted into electronic data), but some are simpler, such as a glass thermometer, which presents visual data.

The term "session time" as used herein refers to a session length and is the amount of time a user or patient spends in a therapy session during a single session. A session is a period of time wherein a user is under therapy. A session records the length and frequency of the therapy or use of the therapy system for further analytics such as to determine the average length of time users spend on therapy, as well as the time-of-day users are most likely to prefer therapy. Monitoring period may be different from session time as monitoring may happen before and after the session time.

The term "situational awareness" as used herein refers to a state of being aware of what is happening around the system in terms of analyzing and checking whether all the elements in the system, patients, nurses, attendants, etc. are doing what they are supposed to be doing, whether anyone or anything in and around the system is a threat to health and safety of the patient.

The term "threshold limits" as used herein refers to known stored data parameters segregating safe and undesirable patient physiological conditions (a safety data set) into groups by threshold limits. They can be upper threshold and lower threshold. They can be either upper or lower threshold only. They can also be of the form either yes or no. For example, historic reactions to a drug as a yes or a no.

The term "timer" or "timer module" or "timer programmer" as used herein refers to a software program or hardware device that keeps track of the elapsed time between two events. A timer may also measure a specified amount of time and signal the user when the "time is up". When an input is activated, the timer starts its operation keeping track of the time. When this time exceeds the programmed time then the timer activates its output. A timer is a clock that controls the sequence of an event while counting in fixed intervals of time. It may also be used for producing precise time delay. It can be used to repeat or initiate an action after a known period of time. An example could be setting up an alarm which triggers at a point of time or after a period of time.

The term "vial" as used herein is a small glass or plastic vessel or bottle, often used to store medication as liquids, powders or capsules for single-dose or multi-dose. Vials comprise barcode technology and when scanned reveal the information regarding drug, manufacturing date, expiration date, dosage, quantity, etc.

The term "vitals", "vital sign", or "vital signal" as used herein refers to signs that provide critical information regarding a patient's current or changing physiological status. They measure the body's core ability to stay alive. Breathing/respiration, heart rate or pulse, temperature and blood pressure are often referred to as vitals. They are signs because they can be observed and/or measured by healthcare professionals. A sign is an observable, objective measure that can often be quantified by using valid and reliable measurement instruments. A sign is different from a symptom, which is how a person experiences a condition. A symptom is subjective and often difficult to measure directly.

The term "wearable" as used herein refers to wearable technology and is a category of electronic devices that can be worn as accessories, embedded in clothing, implanted in the user's body, or even tattooed on the skin. An example of wearable technology is a disposable skin patch with sensors that transmit patient data wirelessly to a nearby control device. Another example could be fitness trackers, often in the form of wristbands or straps, which monitor things like physical activity and vital signs. Trackers may connect wirelessly to an app for data storage, processing, and reporting.

The term "cyber security" as used herein refers to application of technologies, processes, and controls to protect systems, networks, programs, devices, and data from cyber-attacks.

The term "cyber security module" as used herein refers to a module comprising application of technologies, processes, and controls to protect systems, networks, programs, devices and data from cyber-attacks and threats. It aims to reduce the risk of cyber-attacks and protect against the unauthorized exploitation of systems, networks, and technologies. It includes, but is not limited to, critical infrastructure security, application security, network security, cloud security, Internet of Things (IoT) security.

The term "encrypt" used herein refers to securing digital data using one or more mathematical techniques, along with a password or "key" used to decrypt the information. It refers to converting information or data into a code, especially to prevent unauthorized access. It may also refer to concealing information or data by converting it into a code. It may also be referred to as cipher, code, encipher, encode. A simple example is representing alphabets with numbers—say, 'A' is '01', 'B' is '02', and so on. For example, a message like "HELLO" will be encrypted as "0805121215," and this value will be transmitted over the network to the recipient(s).

The term "decrypt" used herein refers to the process of converting an encrypted message back to its original format. It is generally a reverse process of encryption. It decodes the encrypted information so that an authorized user can only decrypt the data because decryption requires a secret key or password. This term could be used to describe a method of unencrypting the data manually or unencrypting the data using the proper codes or keys.

The term "cyber security threat" used herein refers to any possible malicious attack that seeks to unlawfully access data, disrupt digital operations, or damage information. A malicious act includes but is not limited to damage data, steal data, or disrupt digital life in general. Cyber threats include, but are not limited to, malware, spyware, phishing attacks, ransomware, zero-day exploits, trojans, advanced persistent threats, wiper attacks, data manipulation, data destruction, rogue software, malvertising, unpatched software, computer viruses, man-in-the-middle attack, data breaches, Denial of Service (DoS) attacks, and other attack vectors.

The term "hash value" used herein can be thought of as fingerprints for files. The contents of a file are processed through a cryptographic algorithm, and a unique numerical value—the hash value—is produced that identifies the contents of the file. If the contents are modified in any way, the value of the hash will also change significantly. Example algorithms used to produce hash values: the Message Digest-5 (MD5) algorithm and Secure Hash Algorithm-1 (SHA1).

The term "integrity check" as used herein refers to the checking for accuracy and consistency of system related files, data, etc. It may be performed using checking tools that can detect whether any critical system files have been changed, thus enabling the system administrator to look for unauthorized alteration of the system. For example, data integrity corresponds to the quality of data in the databases and to the level by which users examine data quality, integrity, and reliability. Data integrity checks verify that the data in the database is accurate, and functions as expected within a given application. Data integrity refers to the accuracy and consistency (validity) of data over its lifecycle. Compromised data is of little use to enterprises, not to mention the dangers presented by sensitive data loss.

The term "alarm" as used herein refers to a trigger when a component in a system or system fails or does not perform as expected. System may enter an alarm state when a certain event occurs. An alarm Indication signal is a visual signal to indicate the alarm state. For example, the heart rate is very low, a light emitting diode (LED) may glow red alerting that it is beyond the specified limits, and it turns green when the heart rate is within specified limits. Another example could be, when a cyber security threat is detected, a network administrator may be alerted via sound alarm, a message, a glowing LED, a pop-up window, etc. Alarm indication signal may be reported downstream from a detecting device, to prevent adverse situations or cascading effects.

The term "in communication with" as used herein, refers to any coupling, connection, or interaction using electrical signals to exchange information or data, using any system, hardware, software, protocol, or format, regardless of whether the exchange occurs wirelessly or over a wired connection.

As used herein, the term "cryptographic protocol" is also known as security protocol or encryption protocol. It is an abstract or concrete protocol that performs a security-related function and applies cryptographic methods often as sequences of cryptographic primitives. A protocol describes how the algorithms should be used. A sufficiently detailed protocol includes details about data structures and representations, at which point it can be used to implement multiple, interoperable versions of a program. Cryptographic protocols are widely used for secure application-level data transport. A cryptographic protocol usually incorporates at least some of these aspects: key agreement or establishment, entity authentication, symmetric encryption, and message authentication material construction, secured application-level data transport, non-repudiation methods, secret sharing methods, and secure multi-party computation. Hashing algorithms may be used to verify the integrity of data. Secure Socket Layer (SSL) and Transport Layer Security (TLS), the successor to SSL, are cryptographic protocols that may be used by networking switches to secure data communications over a network.

As used herein, the term "perimeter network" refers to a network closest to a router that is not under the enterprise or organization control. Usually, a perimeter network is the final step a packet takes traversing one of your networks on its way to the internet; and conversely the first network encountered by incoming traffic from the Internet. A network perimeter is a secured boundary between the private and locally managed side of a network, often a company's intranet, and the public facing side of a network, often the Internet. The boundary is defined as a perimeter network.

As used herein, the term "network" may include the Internet, a local area network, a wide area network, or combinations thereof. The network may include one or more networks or communication systems, such as the Internet, the telephone system, satellite networks, cable television networks, and various other private and public networks. In addition, the connections may include wired connections (such as wires, cables, fiber optic lines, etc.), wireless connections, or combinations thereof. Furthermore, although not shown, other computers, systems, devices, and networks may also be connected to the network. Network refers to any set of devices or subsystems connected by links joining (directly or indirectly) a set of terminal nodes sharing resources located on or provided by network nodes. The computers use common communication protocols over digital interconnections to communicate with each other. For example, subsystems may comprise the cloud. Cloud refers to servers that are accessed over the Internet, and the software and databases that run on those servers. Cloud servers are located in data centers all over the world. By using cloud computing, users and companies don't have to manage physical servers themselves or run software applications on their own machines.

As used herein, the term "system hardening" is a collection of tools, techniques, and best practices to reduce vulnerability in technology applications, systems, infrastructure, firmware, and other areas. The goal of system hardening may be to reduce security risk by eliminating potential attack vectors and condensing the system's attack surface.

As used herein, the term "SHA256" stands for Secure Hash Algorithm 256-bit is a hash function and it is used for cryptographic security. Cryptographic hash algorithms produce irreversible and unique hashes. The larger the number of possible hashes, the smaller the chance that two values will create the same hash.

The Infusion and Monitoring System (or the System)

An embodiment relates to a system, comprising, a timer module comprising a timer configured to set a time for a session; an infusion module comprising an infusing device configured for administering a drug to a patient; a patient monitoring module comprising a first sensor configured for monitoring a physiological condition of the patient; a drug monitoring and control module comprising a second sensor configured for monitoring a drug delivery to the patient; an alarm generating module comprising signal generator that generates an indication signal when a value of the physiological condition is outside a predefined threshold; wherein the time for the session is dynamically adjusted during the session; and wherein the drug delivery is dynamically adjusted during the session In an embodiment, the system further comprises a remote monitoring system for remotely monitoring the system. In an embodiment, the infusion and monitoring system is integrated with a chair supporting the patient's body and weight. In an embodiment, the infusion and monitoring system is integrated with a bed supporting the patient's body and weight. In an embodiment, the system comprises a first authentication module for authenticating a user to access and initiate a session. In an embodiment, the system further comprises a second authentication module for the patient. In an embodiment, the system further comprises predicting a risk of the drug. In an embodiment, the system further comprises generating a corrective action towards a predicted risk.

In an embodiment, the system is configured to provide situational awareness about the patient. In an embodiment, the system is configurable to be implemented with the plurality of patients in the session. In an embodiment, the system is configurable for a plurality of sessions for a plurality of patients simultaneously. In an embodiment, the patient monitoring module is configured to monitor the patient continuously.

Another embodiment relates to a system, comprising, a timer module comprising a timer configured to set a time for a session; an infusion module comprising an infusing device for administering a drug to a patient; the patient monitoring module comprising a first sensor configured for monitoring of a physiological condition in the patient; the drug monitoring module comprising a second sensor configured for monitoring of quantity of the drug and a rate of drug delivery to the patient; the drug control module comprising an actuator configured to control the rate of drug delivery; an alarm generating module comprising an indication signal configured to generate an alarm when a value of at least one of the physiological condition, the quantity of the drug and the rate of drug delivery exceeds a predefined threshold; and wherein the system is configured for a remote monitoring of the patient; and wherein the system is configured for a remote control of the quantity of the drug and a rate of drug delivery.

Another embodiment relates to a system, comprising, a timer module comprising a timer configured to a time for a session; an automated infusion module comprising a drug infusing device for administering a drug to a patient; a monitoring module comprising, a first sensor configured for monitoring of a physiological condition in the patient; a second sensor configured for monitoring of quantity of the drug and a rate of drug delivery to the patient; a third sensor configured for monitoring of the patient movement; fourth sensor configured for monitoring of an eye movement; a fifth sensor configured to monitor a brain activity; an alarm generating module comprising an indication signal configured to generate an alarm when a value of at least one of the physiological condition, the time of the session, the quantity of the drug and the rate of drug delivery exceeds a predefined threshold; and wherein the time for the session is dynamically adjusted based on at least one of the physiological condition, the eye activity, and the brain activity; wherein the system is configured for a remote monitoring.

Another embodiment relates to a method, comprising the steps of; setting a time for a session; administering a drug to a patient by an automated infusion module; monitoring a physiological condition in the patient; monitoring a quantity of the drug and a rate of drug delivery to the patient; generating an indication signal when a value of at least one of the physiological condition, the quantity of the drug, and the rate of drug delivery exceeds a predefined threshold; and wherein the method is configured for remote monitoring of the patient and the session.

In an embodiment, the system takes a prescription, recognizes the drugs using optical character recognition (OCR) and generates a sequence of instructions to the system processor for executing the drug sequence and dosage for the patient. Optical character recognition (OCR) technology is a business solution for automating data extraction from printed or written text from a scanned document or image file and then converting the text into a machine-readable form to be used for downstream applications. In case of digital or electronic prescriptions, the data is extracted by the processor using Natural Language Processing (NLP) and generates a sequence of instructions to the system processor for executing the drug sequence and dosage for the patient. For example, the prescription may be a combination of ketamine and ondansetron with a mention of dosage. The system captures a picture of the prescription, or reads a digital or electronic prescription, or takes the feed from a drug dispensing system, and programs the drug sequence and drug dosage steps for the treatment. In an embodiment, the time for the session is generated based on initial prediction of the dosage and delivery rate. In an embodiment, a therapy plan is generated with scheduled times and shared with the user or patient.

In an embodiment, the drug vials or pouches can be preloaded in the system manually. In another embodiment, the drug is loaded directly from the drug dispensing system. In an embodiment, the system pauses and alerts when a particular drug in the sequence is a mismatch and/or not found preloaded and/or the drug vial or pouch is empty or expired.

In an embodiment, the settings of the drug infusion are on the prescription or are checked with that of the settings of the drug infusion on the device or system. If there is a mismatch, a warning alarm is provided. An alarm can be an indication signal with light, vibration, sound, or a combination thereof.

An embodiment relates to systems and methods for delivering drugs to a patient using drug infusion devices and control of such devices.

An embodiment relates to systems and methods for monitoring and/or controlling infusion devices, and more particularly to systems and methods of providing or adjusting treatment based upon a patient's physiological condition.

An embodiment relates to monitoring systems, either centralized or decentralized, analysis methods and automatic detections of irregularities in the system and the patient, and alarm indication signal generations.

FIG. 1 shows a drug infusion and monitoring system according to an embodiment of the invention. An embodiment relates to a system, comprising; a timer module 101 comprising a timer configured to set a time for a session; an infusion module 102 comprising an infusing device configured for administering a drug to a patient; a patient monitoring module 103 comprising a first sensor configured for monitoring a physiological condition of the patient; a drug monitoring and control module 104 comprising a second sensor configured for monitoring a drug delivery to the patient; an alarm generating module 105 comprising signal generator that generates an indication signal when a value of the physiological condition is outside a predefined threshold; wherein the time for the session is dynamically adjusted during the session; and wherein the drug delivery is dynamically adjusted during the session. The system further comprises sensors 106 to sense the data, for example of a patient 112 or a drug delivery dosage of drug delivery and control module 104, a processor 107 to analyze the data, a controller 108 to control various devices connected to the system, a memory 109 and a database 110 to store the data. The data can be generated within the system or received from outside the system manually, by wired devices or wireless devices. The system database could be either local to the system or on a remote system. The system comprises a communication system 111 to communicate within the system and outside of the system various messages and instructions as necessary for the system. The data generated during a treatment session 113 such as physiological condition of the patient, session time, adjusted session time, adjusted drug rate, indication signals, etc. are all stored to a data storage along with a time stamp. The data storage (database) can be accessed by the external systems 115 that are authenticated to connect to the database. External systems can be computers, mobile phones, or any other electronic device.

Figure 2:
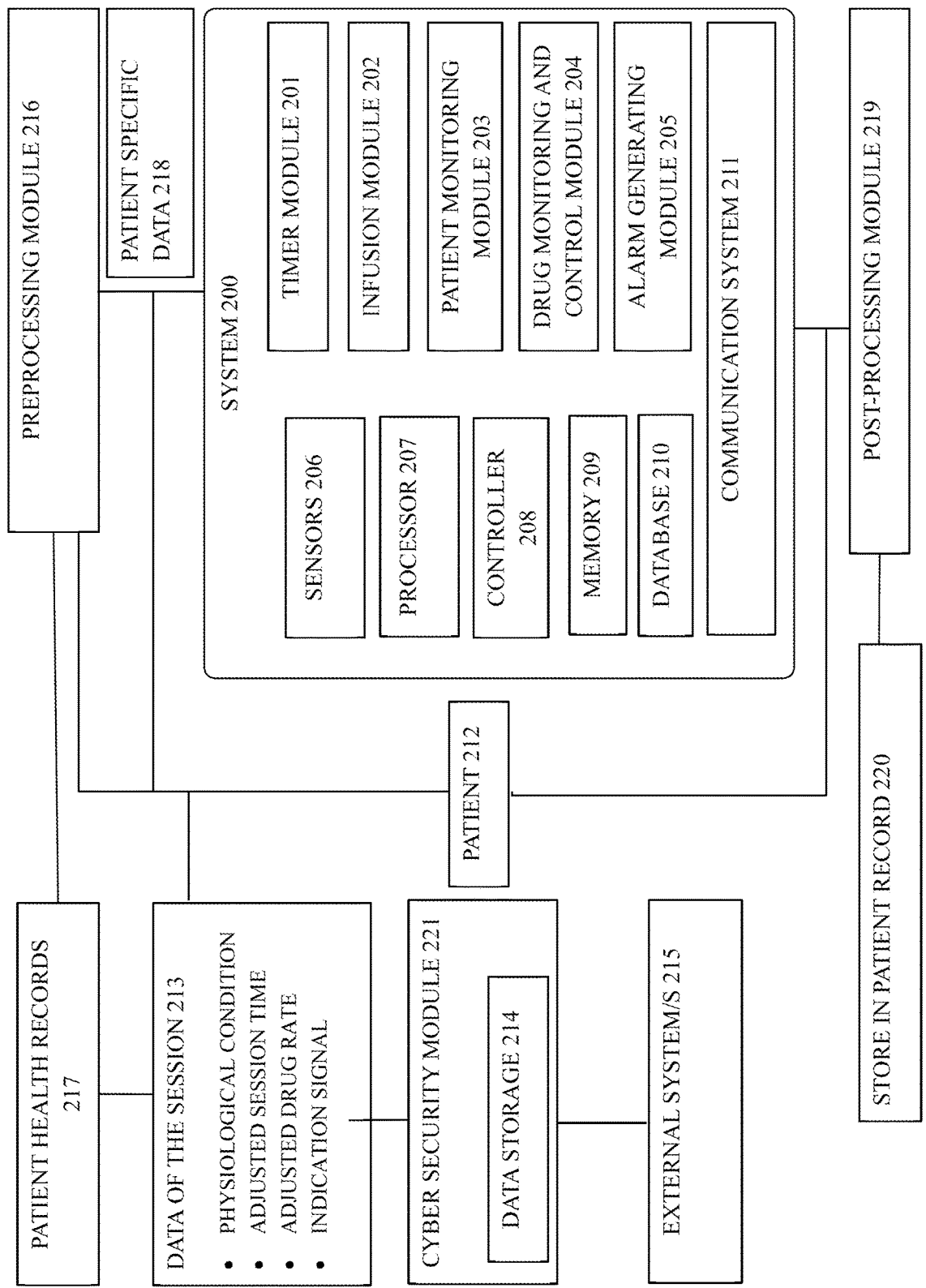
FIG. 2 shows a drug infusion and monitoring system interfacing with additional modules according to an embodiment of the invention.

FIG. 2 shows a drug infusion and monitoring system interfacing with additional modules according to an embodiment of the invention. System 200 interfaces with a pre-processing module 216. In an embodiment, pre-processing module 216 may be connected to patient historical health records 217 and would be generating a profile of the patient along with his physiological condition parameters and thresholds. For example, 218 can be heart rate, blood pressure limits, etc., that are specific to the patient. In another embodiment, the pre-processing module 216 collects the health record data of the patient in real time and will be feeding the data to the system. This patient specific data 218 may be used to generate patient specific treatment plans and patient specific threshold limits for physiological conditions such as heart rate, body temperature, blood pressure, perspiration, etc. In an embodiment, the treatment plan comprises the drug delivery rate and the drug dosage specific to the patient.

In an embodiment, computer systems or kiosks are utilized for automated data collection to collect patient specific data 218 from a subject. In certain embodiments, one or more characteristics of a subject are sensed and compared with corresponding sensed characteristics from other subjects. In one embodiment, data from a subject is utilized to evaluate the overall health of the subject as part of the check-in process. A medical kiosk may be further equipped to provide tele-medicine services, check-in services, and/or prescription services for a subject. The medical kiosk can include a user video conferencing system that is designed to enable the user to have a real-time or near real-time teleconference with a medical provider located remotely from the medical kiosk.

The system 200 further comprises a post-processing module, where the data of the patient and the session data will be part of a statistical data, for usage in cluster analysis to find treatment plans for a patient falling into the cluster. Data security protocols, cyber security 221 and methods will be in place while accessing any patient related data for analysis.

System 200, timer module 201, infusion module 202, patient monitoring module 203, drug monitoring and control module 204, alarm generating module 205, sensors 206, processor 207, controller 208, memory 209, database 210, communication system 211 may be similar to the corresponding elements of system 100 in some embodiments.

Timer Module

A timer is a software program or hardware device that keeps track of the elapsed time between two events. A timer may also measure a specified amount of time and signal the user when the "time is up". When an input is activated, the timer starts its operation keeping track of the time. When this time exceeds the programmed time then the timer activates its output. A timer is a clock that controls the sequence of an event while counting in fixed intervals of time. It is used for producing precise time delay. It can be used to repeat or initiate an action after a known period. An example could be setting up an alarm which triggers at a point of time or after a period. Most microcontrollers have built-in timers that not only generate time delays but can also be used as counters to count an action or event. The value of a counter increases by one every time its corresponding action or event occurs. Timers in a controller are in-built chips or internally integrated devices controlled by special function registers (SFRs) assigned for Timer operations. These SFRs are used to configure Timers in different modes of operation.

In an embodiment, the timer module includes a programmer-timer capable of estimating or calculating a patient's state relevant to the provision of therapy, wherein the programmer-timer communicates with the infusion device either directly or via an external program to effect changes in treatment according to a patient's state.

Figure 3A:
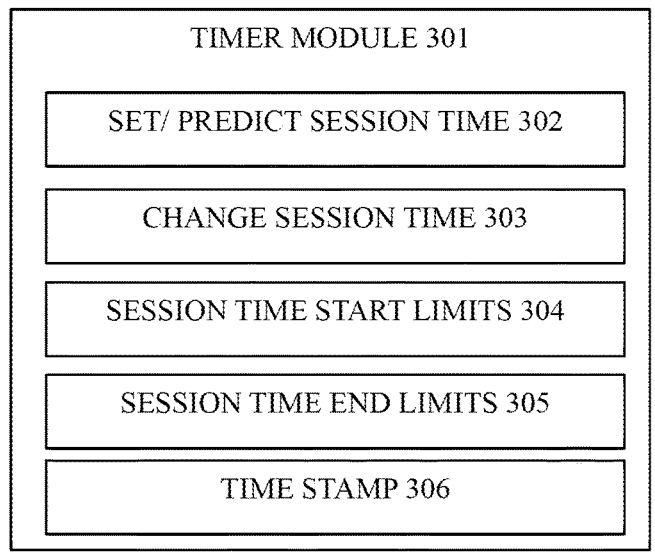
FIG. 3A shows timer module parameters that can be accessed and controlled by the system according to an embodiment of the invention.

FIG. 3A shows timer module 301 parameters that can be accessed and controlled by the system according to an embodiment of the invention. The parameters include but are not limited to; set a session time or predict a session time 302, change session time 303, session time start limits 304, session time end limits 305, and time stamp 306.

Figure 3B:
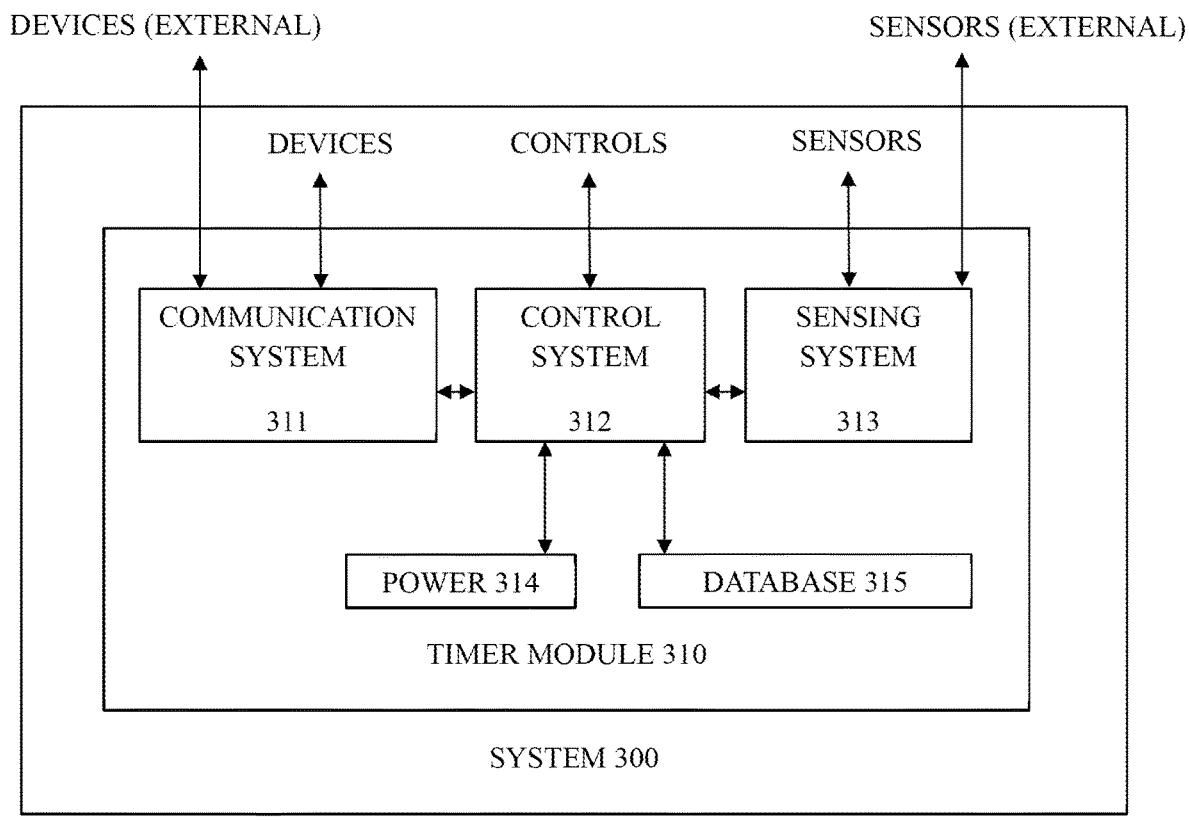
FIG. 3B shows a timer module interfacing with the system according to an embodiment of the invention.

FIG. 3B shows a timer module interfacing with the system according to an embodiment of the invention. As shown in FIG. 3B, the timer module or timer-programmer module can communicate with the system. The timer-programmer can communicate via the communication module or communication system 311 during a treatment session. The programmer can contain a control system 312 and a database 315. Control system 312, for example, can control or implement different treatment protocols, the parameters for each protocol, and an alert event set. The timer-programmer can also include a power supply 314 which may be a wired power supply or a battery. In an embodiment, the timer-programmer may have a stimulation module, wherein a stimulation module provides a predefined stimulation to measure the response of a patient.

The timer-programmer can be realized in internal embodiments or in external embodiments. For example, the timer-programmer may be incorporated into a watch-like mechanism that serves as an external programmer and is worn on a patient's wrist. The timer-programmer can be realized in the form of a software module of an external programmer that works with the stimulator. In an embodiment, the external programmer, and the communication module of the stimulator each include a transceiver operable in a permitted band of frequency, enabling communication between the devices over a range of several meters. A timer-programmer can serve to turn the stimulation device "on" or "off" and can automatically send alerts and has provisions for incorporating additional features. The timer-programmer thereby allows generic stimulators, which are already Food and Drug Administration (FDA) approved, to provide treatment according to timing or other information, even if this capability is not normally available in the generic device. The timer module may be independent or a part of the system. It may utilize the sensing system, control system and communication system, power and database of the system or can have its own sensing system, control system and communication system, power, and database to make it independent of the system but can connect to the system. The timer module includes a sensing system 313 that communicates with one or more sensors adapted to collect information from the patient, thereby allowing the timer module to adjust treatment, for example, based upon a patient's state derived from sensed data. Alternatively, if the infusion device has sensors, then the timer module can use sensor data which is obtained by the device and transmitted to the timer module. If the timer module is expected to perform a large amount of communication with the device, it may include a communication subsystem as a separate subsystem and, rather than using telemetry, the timer-programmer can have a physical communication port. This port allows a physical connection to be made between the timer-programmer and at least one infusion device which is also configured with a communication port so that a physical link can connect the two devices.

The timer-programmer can be programmed to communicate with most commercially available devices that are already designed to communicate with the external programmers provided by a manufacturer. To accomplish this, the communication subsystem can include routines for identifying an infusion device, establishing communication, making error and parity checks, dysfunction alert routines to alert the concerned in the case of breakage, and alert routines for automatically notifying or querying the concerned about treatment operations that have been defined as alert events.

According to an embodiment, the timer module 301 is programmed to set session time or predict a session time 302, change session time 303, session time start limits 304, session time end limits 305 and record the data along with a time stamp 306. It can further record the time stamp data along with the drug information, for example drug id, drug delivery rate, and time stamp.

In an embodiment, the timer module is configured to monitor the session time continuously. In an embodiment, the time for the session comprises stages of therapy, wherein the stages of therapy are monitored, and a stage time and a stage drug delivery rate are configured to be adjusted based on the physiological condition of the patient. In an embodiment, the time for the session is a predetermined value based on a health condition of the patient. In an embodiment, the session comprises at least one of a psychotherapy session, a massage session, a chemotherapy session, and a surgery.

Infusion Module and Infusion Device

Figure 4A:
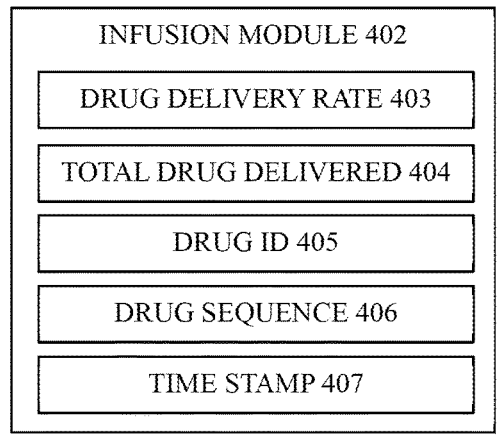
FIG. 4A shows infusion module parameters that can be accessed and controlled by the system according to an embodiment of the invention.

FIG. 4A shows infusion module 402 parameters, drug delivery rate 403, total drug delivered 404, drug id 405, drug sequence 406, time stamp 407 that can be accessed and controlled by the system according to an embodiment of the invention.

Figure 4B:
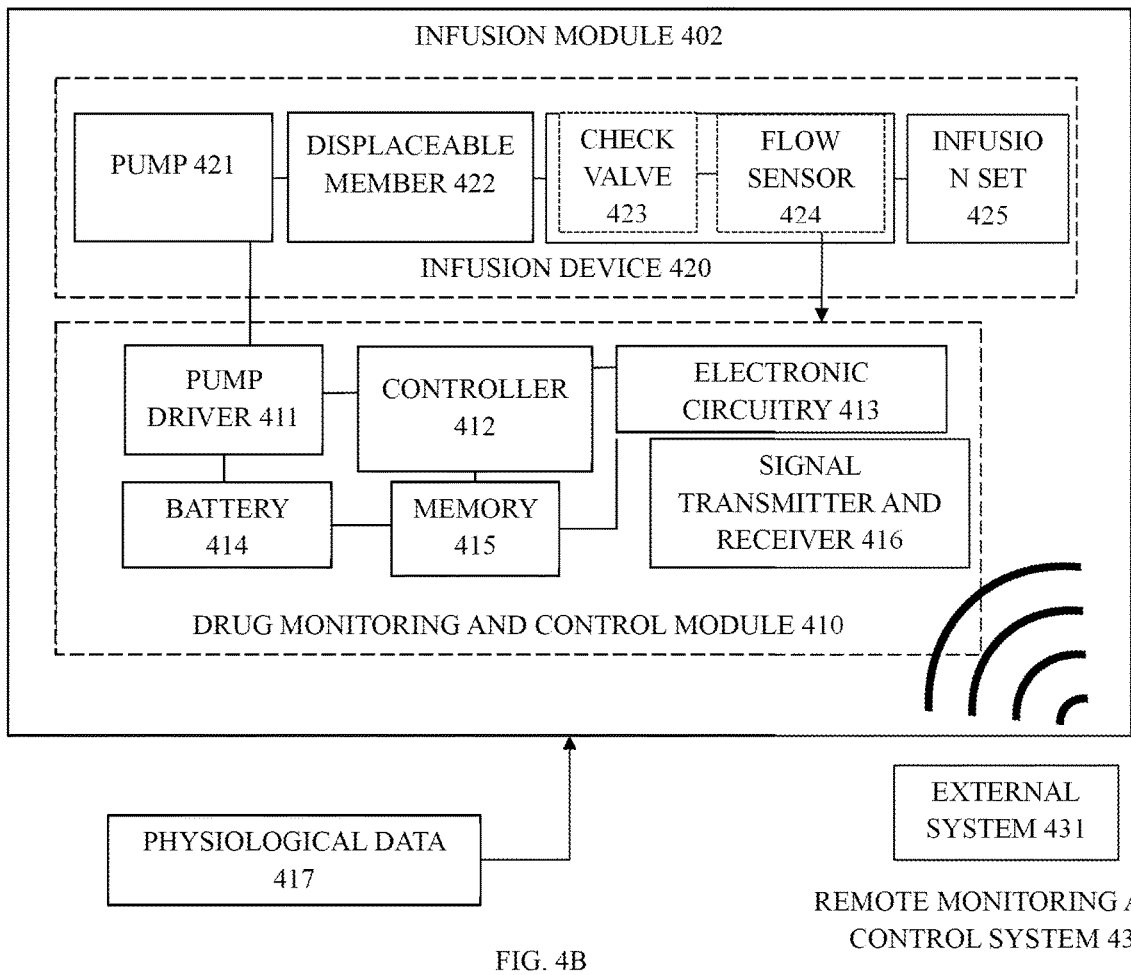
FIG. 4B shows infusion module interfacing with the drug monitoring and control module of the system according to an embodiment of the invention.

FIG. 4B shows infusion module 402 interfacing with the drug monitoring and control module 410 of the system according to an embodiment of the invention. In an embodiment, the infusion device 420 includes a drug reservoir that interfaces with a pump 421 via a displaceable member. The displaceable member may be, for example, a piston, diaphragm, bladder, or plunger. While in use, the drug reservoir is filled with medication in liquid form, a vial, and pressure generated by the pump 421 which moves or expands the displaceable member 422 so as to push the liquid drug out of the reservoir. A cannula connected to an outlet of the drug reservoir conducts the liquid to an infusion set 425. The cannula may be made of impermeable tubing, such as medical-grade plastic. The infusion set 425 may include a catheter that is fluidically connected to the cannula and delivers the drug to a target region. A lancet and associated insertion mechanism may be used to drive the catheter through the skin. Alternatively, the infusion set may include another type of drug-delivery vehicle, e.g., a sponge or other means facilitating drug absorption through the skin surface. The pressure generated by the pump 421 may be regulated via a pump driver 411 by a controller 412. In an embodiment, the controller can be a system level controller in communication with the device. For example, in an electrolytic pump, the controller 412 may set the drive current and thereby control the rate of drug delivery, which, in turn, determines the pressure. The cannula may further include a check valve 423 that prevents backflow of liquid into the drug reservoir. The drug pump device may include electronic circuitry 413, integrated with the controller 412, for processing the sensor signal(s) and, optionally, providing pump status information to a user or an attendant by means of LEDs, other visual displays, vibrational signals, or audio signals. In addition to controlling the drug pump, the controller may be used to control other components of the drug pump system; for example, it may trigger insertion of the lancet and catheter. The controller may be a microcontroller, i.e., an integrated circuit including a processor core, memory (e.g., in the form of flash memory, read-only memory (ROM), and/or random-access memory (RAM)), and input/output ports. The memory may store firmware that directs operation of the drug pump device. In addition, the device may include read-write system memory. In certain alternative embodiments, the controller 412 is a general-purpose microprocessor that communicates with the memory 415. The memory (or memory that is part of a microcontroller) may store a drug-delivery protocol in the form of instructions executable by the controller, which may be loaded into the memory by data transfer from a hard drive, flash drive, or other storage device, e.g., via a USB, Ethernet, or firewire port. In alternative embodiments, the controller 412 comprises analog circuitry designed to perform the intended function, e.g., to deliver the drug to the patient. In general, drug pump devices may be configured to achieve sustained drug release over periods ranging from several hours to several months, with dosage events occurring at specific times or time intervals. Flow rates of fluid flowing through the cannula may range from nanoliters per minute to microliters per minute. In an embodiment, the patient condition data, physiological data 417, may be fed to the infusion module 402 which would control the drug dosage by altering the pump settings. In an embodiment, a clinician or a nurse may alter the pump programming in system memory if the patient's condition changes.

In an embodiment, an external system 431, for example a smartphone may communicate with the drug pump device/infusion device 420 using a connection already built into the phone, such as a Wi-Fi, Bluetooth, or near-field communication (NFC) connection. Alternatively, a smartphone dongle may be used to customize the data-transfer protocol between the smartphone and the infusion device, which facilitates optimizing the sender and/or receiver components of the drug pump device, e.g., for reduced power consumption, and may provide a layer of security beyond that available through the smartphone. A smartphone dongle is a special hardware component, typically equipped with a microcontroller, designed to mate with a corresponding connector on the smartphone (e.g., a Mini USB connector or the proprietary iPhone connector). The connector may accommodate several power and signal lines (including, e.g., serial, or parallel ports) to facilitate communication between the dongle and the smartphone and to power the dongle via the phone.

In certain embodiments, the smartphone and pump device communicate over a (unidirectional or bidirectional) infrared (IR) link, which may utilize one or more IR light-emitting diodes and phototransistors as transmitters and receivers, respectively. Data transfer via the IR link may be based on a protocol with error detection or error correction on the receiving end. A suitable protocol is the IrDA standard for IR data communication, which is well-established and easy to implement. Communication between the drug pump device and the smartphone may also occur at radio frequencies (RF), using, e.g., a copper antenna as the transmitter/receiver component. The transmitter/receiver and associated circuitry, which may collectively be referred to as the communication module of the drug pump device, may be powered by the battery and/or by the signal transmitted from the smartphone or other communication device. In some embodiments, the communication module remains in a dormant state until "woken up" by an external signal, thereby conserving power. In an embodiment, the device data and access are secured and encrypted to remove any Man-in-the-middle attacks.

In some embodiments, the smartphone is used to send real-time signals to the drug pump device, for example, to turn the pump on or off, or to adjust an otherwise constant drug delivery rate, and in some embodiments, the smartphone serves to program or reprogram the drug pump device for subsequent operation over a period in accordance with a drug-delivery protocol. The communication link between the smartphone and the drug pump device may be unidirectional (typically allowing signals only to be sent from the phone and received by the drug pump device) or bi-directional (facilitating, e.g., transmission of status information from the infusion device to be sent to the smartphone). A special software application (e.g., an "app") executing as a running process on the smartphone may provide a user interface for controlling the infusion pump device via the smartphone display. As a security measure, the application may be configured to be accessible only when the dongle is connected to the smartphone. The application may further facilitate communication between the smartphone and a remote party. For example, a health-care provider may communicate with his patient's smartphone to obtain status updates from the drug pump device and based on this information, push a new drug-delivery protocol onto the patient's smartphone, which in turn uploads this new protocol to the drug pump device. In an embodiment, the device data and access are secured and encrypted to remove any Man-in-the-middle attacks.

In an embodiment, the infusion pump is configured to receive data from external monitoring devices or wearable devices, such as a heart rate monitor from a wearable watch. The processor on the infusion pump or on the system may analyze the heart rate changes and predict a level or a stage in the treatment the patient is experiencing. In an embodiment, it can predict a drug dosage and a drug dosage rate with the inputs it receives about the physiological condition of the patient. In another embodiment, the infusion pump can predict and design a therapy based on the physiological condition inputs of the patient. In an embodiment, the infusion pump may be incorporated within the chair. In an embodiment the sensors that provide physiological condition data are incorporated into the chair. In another embodiment, these sensors which provide physiological condition data may be wearable devices.

In an embodiment, the drug delivery device is configured for automatic and continuous monitoring of the level of consciousness in a patient based on voltages representative of the patient's cortical activity obtained by means of an electroencephalograph (EEG). In an embodiment, the system is configured for automatic and continuous monitoring of the level of consciousness in a patient based on voltages representative of the patient's cortical activity obtained by means of an electroencephalograph (EEG) and feeds the data to drug delivery devices.

In an embodiment, the device maintains, increases, or decreases a drug rate delivery to the patient, via an infusion device, in response to selected frequencies of brain potential to maintain a level of consciousness. In an embodiment, it is a device for measuring a patient's sensitivity to pain during the provision of a drug, by applying a stimulus and regulating the level of drug delivery in response to EEG signals indicating the patient's response to the stimulus. In an embodiment, physiological measures such as heart rate, respiration rate, and eye activity are sensed and evaluated to determine if the patient is sleeping or awake.

In an embodiment, the device comprises a plurality of pumps configured to hold a plurality of drugs and execute commands to deliver a certain drug for a certain duration and sequence in which the drugs are to be delivered.

In an embodiment, the infusing device is configured to receive at least a vial comprising the drug, wherein a vial has a unique identifier. In an embodiment, the infusing device is configured to receive a plurality of vials comprising the drug and a second drug, wherein each of the plurality of vials has a unique identifier. In an embodiment, the drug is a curing drug, and a second drug is a drug to counter a side effect of the drug. In an embodiment, the drug is a psychotherapy drug comprising ketamine. In an embodiment, the infusing device is configured to administer the plurality of drugs as per a dosage rule and in a specific sequence. In an embodiment, the specific sequence is predetermined or determined dynamically during the session. In an embodiment, the administering the drug is continuous and automated and can be controlled by the system. In an embodiment, the administering the drug is continuous and automated and controlled from a device outside of the system for remote monitoring and control.

Drug Monitoring Module

Figure 5A:
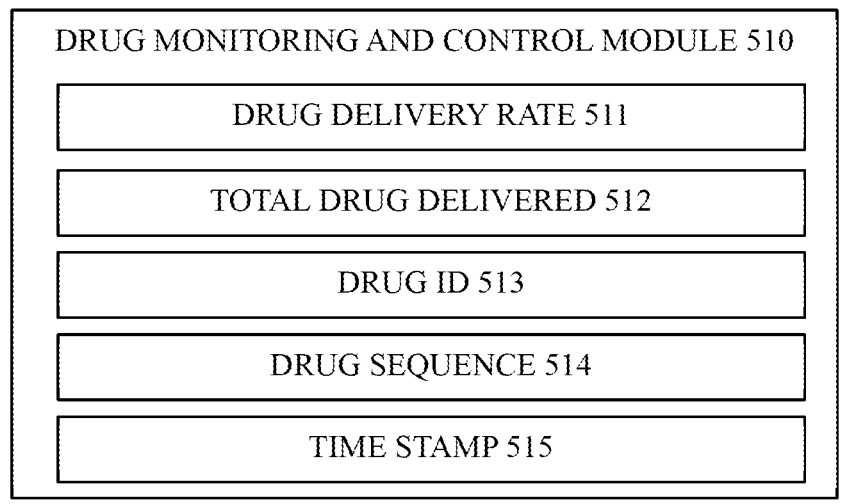
FIG. 5A shows drug monitoring and control module parameters that can be accessed and controlled by the system according to an embodiment of the invention.

A drug monitoring module monitors the delivery of the drug to a patient. FIG. 5A shows drug monitoring and control module 510 parameters that can be accessed and controlled by the system according to an embodiment of the invention. The parameters include but are not limited to drug delivery rate 511, total drug delivered 512, drug id 513, drug sequence 514, time stamp 515.

Figure 5B:
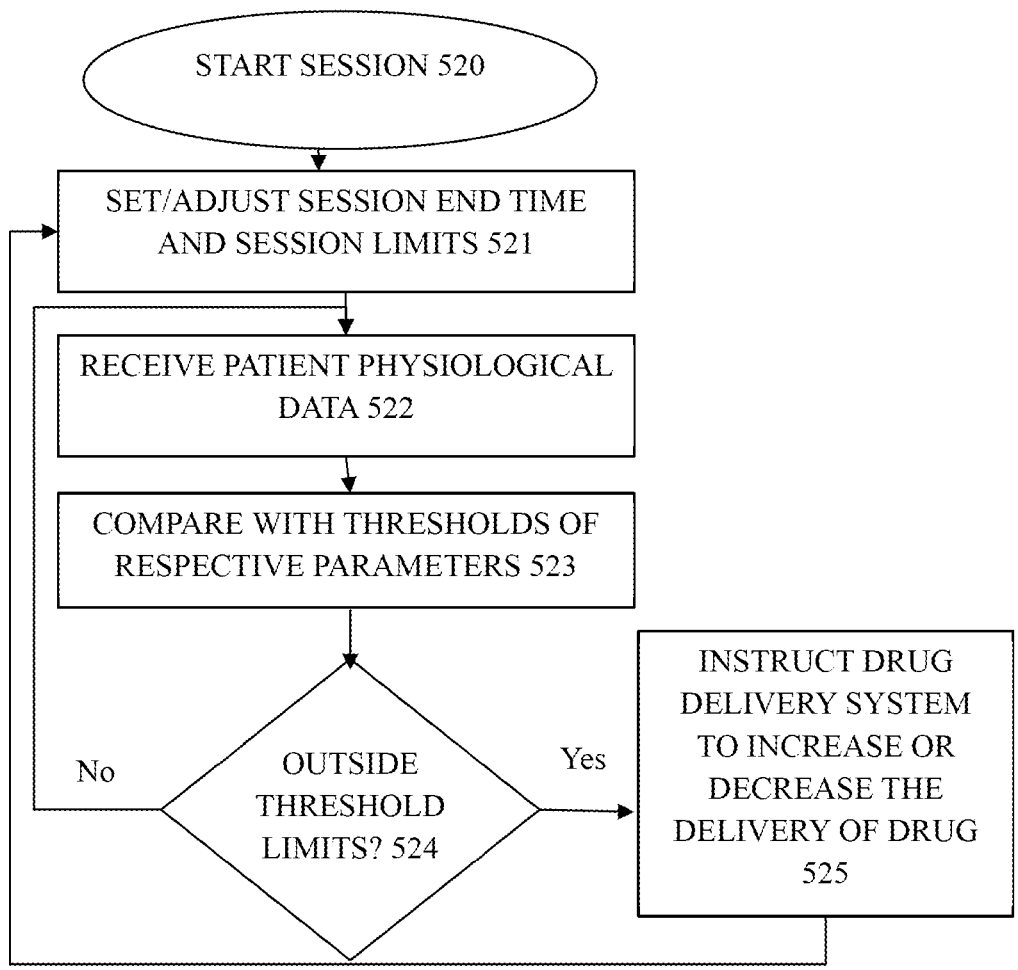
FIG. 5B shows drug monitoring and control module logic of the system according to an embodiment of the invention.

FIG. 5B shows drug monitoring and control logic of the system according to an embodiment of the invention. FIG. 5B is a block diagram overview of an embodiment of the invention showing a data flow diagram depicting the drug delivery management steps performed by the software/logic control of the microprocessor controller. It comprises starting of the session as shown at 520 and then setting of initial session time and session limits. Session limits could be minimum and maximum limits which correspond to the range of time in which the session either can start as in case of session start limits or stop as in case of session end limits. In an embodiment, one or more patient health monitors, which may include one or more known patient physiological condition monitors as shown in 522 such as pulse oximeters, capnometers, other ventilatory monitors, non-invasive blood pressure monitors, EKG, EEG, and others, as well as a patient consciousness monitoring system, are electronically coupled, through suitable Analogue to Digital (A-D) converters where appropriate, to the electronic controller. Patient health monitors generate electronic feedback signals representing actual patient physiological data which are converted to electronic signals and then provided to the controller. The electronic controller, e.g., through appropriate software and/or logic, compares the received electronic patient feedback signals with the threshold limits stored in a memory device as shown at 523.

The stored threshold limits contain at least one set of data parameters that represent limits that segregate safe and undesirable patient physiological conditions. In an embodiment, these can be derived from a pre-processing module. In an embodiment, the patient may be checked in real time for generating these thresholds. In another embodiment, a cluster analysis is performed to determine the threshold limits for patients falling into that cluster. Based on the comparison of the actual monitored patient physiological data with the threshold limits, the controller determines whether the monitored patient physiological data is outside of a safe range as shown at 524. If the monitored patient data is outside of a threshold, the electronic controller sends instruction commands (signals) to the drug delivery controller instructing the drug delivery controller to manage or adjust (e.g., reduce, increase, or maintain) a drug delivery rate as shown at 525. When the drug delivery rate is changed, the session end time is set to a new limit as shown at 521. Drug delivery controller may be a standard solenoid valve-type electronic flow controller known to those skilled in the art.

In an embodiment, the drug monitoring logic may interface with a drug dosage request device which allows a direct control of drug dosage. A feedback signal from an infusion device representing the patient's increase or decrease in drug dosage request is electronically communicated to the controller which employs decision-making software, including comparison of monitored patient conditions with stored threshold limits reflecting patient safe physiological conditions, to effect safe, optimized drug delivery in response to patient physiological condition. In an embodiment, the amount of increase or decrease administered by the controller can be pre-set by the physician. In another embodiment, the amount of increase or decrease administered by the controller can be a function of the physiological condition of the patient. For example, where the drug being delivered is Ketamine, the increase or decrease may be within approved limits, or they can be such that the session can end in a pre-set maximum time limit. When a change in the physiological condition of the patient is within the safe limits, that is within thresholds, the drug delivery device remains to deliver the drug at the rate at which it was delivered. The invention thus integrates and correlates drug delivery and control systems with electronic monitoring of patient physiological conditions. For example, if the patient experiences a drop in body temperature, the system automatically sends a control signal to the controller for an adjustment (a decrease or stop or a halt) in drug dosage.

Controller generates an instruction in response thereto to maintain, increase, or decrease the level of drug delivery provided to the patient thereby managing and correlating drug delivery to safe, cost-effective, and optimized values. The controller is operatively and electronically coupled to electronic flow controllers that adjust flow of drug in a closed-loop fashion. In intravenous embodiments such flow controllers would adjust the flow of one or more combinations of intravenous (IV) drugs. It should be recognized that the electronic values provided to microprocessor controllers to effect management and correlation of drug delivery, could include one or more signals representing patient vital signs and other health conditions such as pulse oximetry, without necessarily including signal(s) representing level of patient consciousness, and vice versa.

According to an embodiment, the drug monitoring and control module is programmed to monitor drug delivery rate, total drug delivered, drug id, drug sequence along with time stamp. In an embodiment, the infusion pump is equipped to alert in the event of a problem, e.g., when air or another blockage is detected in the tubing that delivers fluid to the patient, a risk of an adverse drug interaction, or when the pump parameters are set outside of specified safety limits.

In an embodiment, the drug monitoring and control module is configured to monitor a quantity of the drug and a rate of drug delivery to the patient. In an embodiment, the drug monitoring module is further configured to store data of the amount of drug delivered to the patient over a period. In an embodiment, the drug monitoring module is further configured to store data of the rate of drug delivery to a database.

In an embodiment, the predetermined threshold is configured for the patient based on historic health record and current physiological condition. In an embodiment, dynamically adjusting the time for the session and the rate of drug delivery are based on feedback from the first sensor and the second sensor.

Alarm Generating Module

Figure 6:
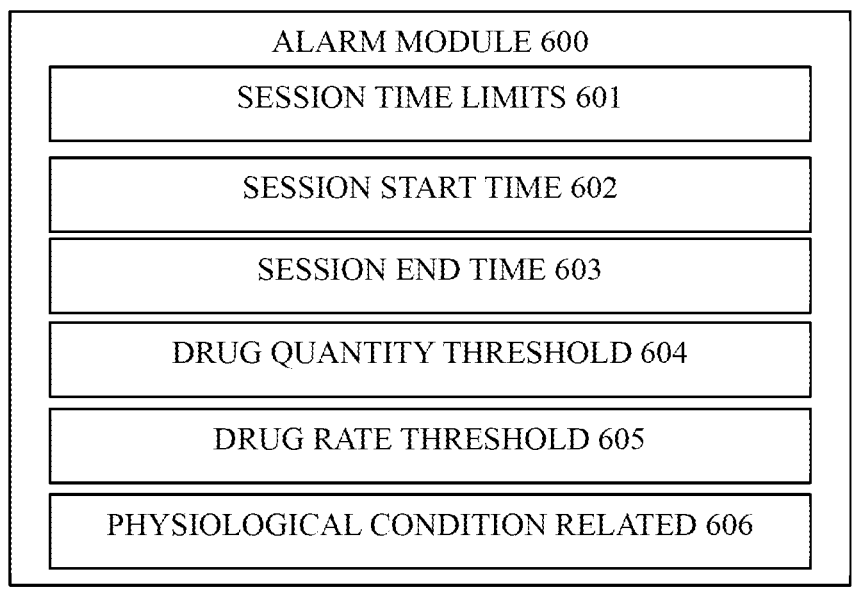
FIG. 6 shows alarm module parameters that can be accessed and controlled according to an embodiment of the invention.

FIG. 6 shows parameters of the alarm module as shown in 600 that can be accessed and controlled according to an embodiment of the invention. The parameters include but are not limited to session time limits 601, session start time 602, session end time 603, drug quantity threshold 604, drug rate threshold 605, physiological condition related thresholds 606. In some embodiments, the system may generate an alarm when it predicts that any parameter may go beyond the threshold.

Various forms of notification, according to varying degrees of urgency, are possible in a system. For example, if the patient is likely to be disturbed during sleep or relaxation by an audio signal, and such a high level of intrusion is unnecessary, the system may send a text alert signal to an external device or a registered device, allowing the patient or the concerned to check for alerts when the patient awakens. In such a case, a flashing light may also be provided, like voicemail indicators found on telephones.

In an embodiment, the timer module is connected to a light indication signal system. In an embodiment, outside of the patient therapy receiving room would be a light indication signal system that is programmed to send the signal to a registered device such as an iPad or some other kind of system such as a light fixed on a door. In an embodiment, the timer is then connected to the front desk, which can be used to monitor the sensor data for example, vitals, heart monitor, and pupils of the patient. The front desk may be used to monitor the patient remotely. In an embodiment, a light will indicate that the session is going to end in a certain period, for example, in 15 minutes.

In an embodiment, the patient will be notified of the stage of treatment by a color of light. The light may be embedded in a chair, a smart band, a smart watch, a mobile phone, an attendant's computer, a front desk door, etc. For example, a yellow light can mean the session will be ending in the next 15 minutes. In an embodiment, the treatment session can be divided into phases and each phase can be associated and indicated by a certain color of light.

In an embodiment, the treatment is divided into stages. Each of the stages is mapped based on patient symptoms or experience. For example, a first stage, a take-off stage where the drug is getting into the bloodstream, but the patient is not feeling anything, then a second stage, a cruise stage where the patient is subconscious and having an experience, and then a third stage, a landing stage where the patient is coming out of the drug or weaning out of it. A different color of light may be used to monitor and indicate which stage of treatment the patient is in. In an embodiment, the stages of the treatment are marked based on an average or a statistical parameter of data collected from samples of patients who are undergoing or have undergone the treatment. In another embodiment, the stages are determined based on at least one selected from patient's vitals, physiological condition, patient movement, patient comfort and/or a correlation among the sensed parameters. In an embodiment, the data from the patients may be used to perform cluster analysis. In an embodiment, the cluster analysis may be used in conjunction with a predictive algorithm to predict/determine treatment time of the session and each stage within the session. In an embodiment, patient characteristics such as body weight, height, age, demographics, race, ethnicity, residence, genetic information, etc., may be used by the predictive algorithm.

In an embodiment, the pump is programmed to infuse the drugs in a specific sequence and at a specific drug delivery rate based on a prediction of session time. In an embodiment, the drug delivery rate, amount of drug and session end time are adjusted based on real-time feedback from the patient's vitals, physiological condition, and patient movement. In an embodiment, in the treatment drug delivery rate, the amount of drug is adjusted in each stage based on real-time feedback from the patient's vitals, physiological condition, and patient movement which is an indication of comfort of the patient while in therapy.

In an embodiment, the indicating signal is a light signal. In an embodiment, the indicating signal is a light signal of a color and is configured for a specific message. In an embodiment, the indication signal is configured to be a light cue at least in one of a room, a door, a chair, a wearable device, and a computer.

In an embodiment, the system further comprises a push notification module configured to deliver automated message notifications to the patient and an attendee.

Patient Monitoring Module

Figure 7:
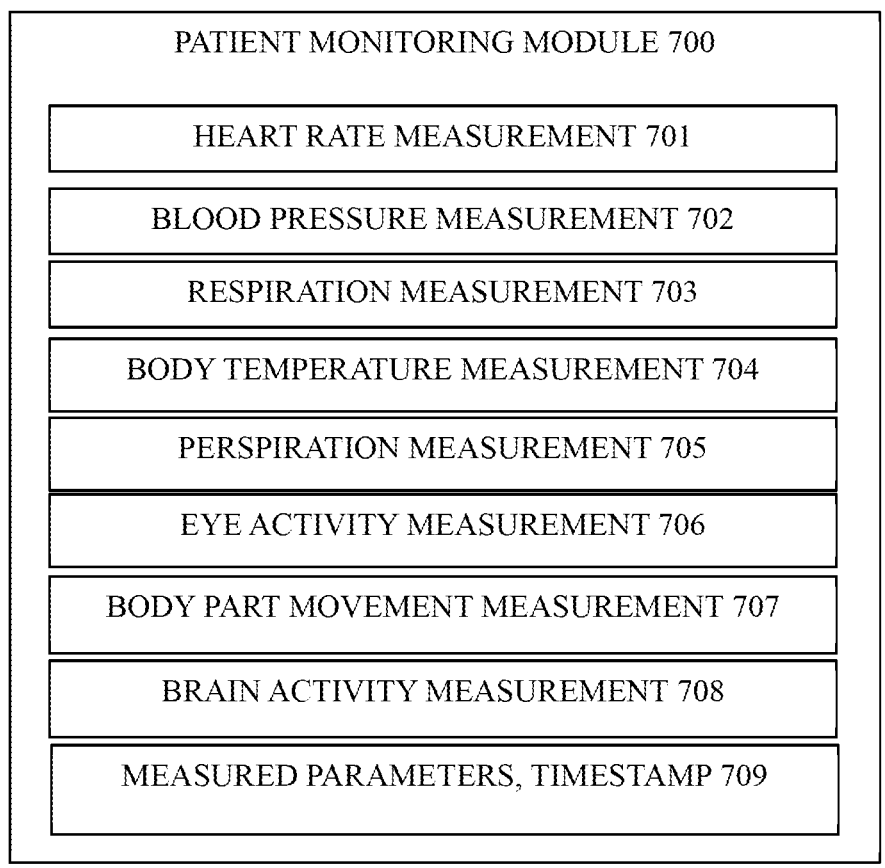
FIG. 7 shows patient monitoring module parameters that can be accessed and controlled by the system according to an embodiment of the invention.

FIG. 7 shows parameters of the patient monitoring module as shown at 700 that can be accessed and controlled by the system according to an embodiment of the invention. These parameters include but not limited to heart rate 701, blood pressure 702, respiration (breathing rate) 703, body temperature 704, perspiration 705, eye activity 706, body part movement 707 for example head movement, brain activity 708, where the measured parameter is provided along with time stamp as shown at 709.

Physiological condition monitoring: In an embodiment, the patient monitoring module comprises a monitoring system to monitor at least a parameter related to the patient, wherein the parameter comprises at least one selected from a brain activity, a responsiveness, a seizure, a vomiting, a breathing rate, a heart rate, a heart activity, a body temperature, a blood pressure, a pupil color, a pupil dilation, a pupil constriction, a sound made by the patient, a lip color, a fingertip color, a response to an outside stimuli, a response to a loud noise, a shaking of a body part, and a skin color.

Sensors may be included and positioned in such places where the user or the patient interacts with the system. For example, a chair, a wearable device, etc. In an embodiment, these sensors obtain data about the health of the user/patient data and/or data about the comfort of the user/patient. According to an embodiment, the health data sensors can be included in the drug dispensing system, a therapy receiving chair, and a seat where the patient is checked for vitals before moving on to therapy. These sensors can measure various health telemetry for the patient/user (e.g., heart rate, temperature, blood pressure, blood presence, blood composition, etc.).

In an embodiment, sensors in the seats may also provide for health telemetry (e.g., presence of liquid, weight, weight shifts, etc.). Infrared sensors could detect a person's temperature, optical sensors can determine a person's position and whether the person has become unconscious. Optionally, the chair sensors or wearable sensors may provide health telemetry and/or identification via one or more of load cells, force transducers, weight sensors, moisture detection sensor, electrical conductivity/resistance sensor, and the like. For example, the chair sensor may determine a user's weight and may compare it to user data stored in memory to determine whether a match exists between the detected weight and the patient. In an embodiment, if the chair sensors detect that a patient is fidgeting, or moving, in a seemingly uncontrollable manner, the system may determine that the user has suffered or suffering a nervous and/or muscular system issue (e.g., seizure, etc.) or having a discomfort while taking the therapy or the drug that is being given. The system control may then cause the drug delivery to slow down or stop and in addition or alternatively the system controller can alert a nurse or an attendant of an emergency. Other health sensors are possible and included herein.

Health telemetry and other data may be collected using sensors via the chair arm rests or where the patient places or relaxes his hands comprising sensors. Optionally, the sensors embedded in arm rests or where the patient places his arms while taking the therapy, may collect heart rate, temperature, blood pressure, and the like, associated with the patient via at least one contact disposed on or about the arm rest. In an embodiment, the system may receive them via a wearable device, like a watch.

Safety sensors can measure whether the person is safe or acting safe. Optical sensors can determine a person's position and focus. If the person stops looking at an object, the optical sensor can detect the lack of focus. Sensors in the chair may detect if a person is leaning forward or stationary or moving continuously, etc. Other sensors are possible and contemplated as if included herein.

Environmental sensors, including one or more of temperature, humidity, air, oxygen, carbon monoxide, smoke, and other environmental condition sensors may be used in the system. In another embodiment, the environmental condition sensors may be embedded outside the system and in the room or place where the therapy is given, for example a therapy room, and the system may interface to collect the data from these sensors. These environmental sensors may be used to collect data relating to the safety, comfort, and/or condition of the interior space where the patient is receiving the therapy. Among other things, the data collected by the environmental sensors may be used by the system control to alter functions of a therapy.

The environment may correspond to an interior space of a therapy receiving room and/or specific areas and/or zones of the room. It should be appreciated that an environment may correspond to a patient. For example, a low oxygen environment may be detected by the environmental sensors and associated with a patient who is receiving or taking a therapy in that zone. In response to detecting the low oxygen environment, the system may alter the environment, or provide an alert to alter the environment, especially in the zone, to increase the amount of oxygen in the zone. Additionally, or alternatively, the environmental sensors may be used to report conditions associated with a vehicle (e.g., low oxygen, low humidity, etc.). The conditions may be reported to a user and/or a third party via at least one communication module as provided herein.

Comfort sensors can collect information about a person's comfort. Temperature sensors may detect a temperature of the therapy area where the patient is receiving therapy. Moisture sensors can determine relative humidity. Audio sensors can detect sounds or other distractions. Audio sensors may also receive input from a person through voice data. Other comfort sensors are possible and contemplated as if included herein.

The system may include one or more motion sensors. These motion sensors may detect motion and/or movement of patients or users. Optionally, the motion sensors may be used alone or in combination to detect movement. For example, a patient may be receiving a therapy and the movement of the patient could be detected by the motion sensors. Optionally, a nurse or therapy provider could be alerted of this movement by one or more of the devices connected to the system. In another example, a patient may attempt to reach for a water container. In this case, the movement (i.e., reaching) of the patient may be detected by the motion sensors. Optionally, the path, trajectory, anticipated path, and/or some other direction of movement/motion may be determined using the motion sensors. In response to detecting the movement and/or the direction associated with the movement, the patient may be prevented from interfacing with and/or accessing at least some of the system control features (e.g., the features represented by icons may be hidden or locked from a user interface like increasing the drug rate, the features may be accessible for use by the user, for example music control or a game to play while receiving therapy). As can be appreciated, the user or nurse may be alerted of the movement/motion such that the patient can be prevented from interacting with the controls. Optionally, the number of motion sensors in a system or a chair, or areas of a system or a chair, may be increased to increase an accuracy associated with motion detected.

The user interface may comprise sensors configured to collect data relating to one or more patients receiving a therapy using the system. As can be appreciated, the system may include sensors that are configured to collect data from patients in one or more areas and zones of the system. For example, each area and/or zone of the system may include one or more of the sensors. Examples of associated sensors may include, but are not limited to, infrared sensors, motion sensors, weight sensors, wireless network sensors, biometric sensors, camera (or image) sensors, audio sensors, and more.

Infrared sensors may be used to measure IR light irradiating from at least one surface, patient, or other object in the system. Among other things, the Infrared sensors may be used to measure temperatures, form images (especially in low light conditions), identify users, and even detect motion.

Weight sensors may be employed to collect data relating to objects and/or users in various areas. In some cases, the weight sensors may be included in the seats and/or floor or a floor mat.

Optionally, the system may include a wireless network sensor. This sensor may be configured to detect one or more wireless network(s). Examples of wireless networks may include, but are not limited to, wireless communications utilizing Bluetooth®, Wi-Fi™, ZigBee, IEEE 802.11, and other wireless technology standards. For example, a mobile hotspot may be detected via the wireless network sensor. In this case, the system may determine to utilize and/or share the mobile hotspot detected via/with one or more other devices and/or components associated with the system.

Biometric sensors may be employed to identify and/or record characteristics associated with a user. It is anticipated that biometric sensors can include at least one of image sensors, IR sensors, fingerprint readers, weight sensors, load cells, force transducers, heart rate monitors, blood pressure monitors, and the like as provided herein.

The camera sensors may be similar to image sensors. Optionally, the camera sensors may record still images, video, and/or combinations thereof. The audio sensors may be similar to the interior sound receivers. The audio sensors may be configured to receive audio input from a user of the system. The audio input from a user may correspond to voice commands, sounds made by the user, phone calls made while using the system, and/or other audible expressions made.

The force sensors may include one or more sensors configured to detect a force observed. One example of a force sensor may include a force transducer that converts measured forces (e.g., force, weight, pressure, etc.) into output signals. Orientation sensors can include accelerometers, gyroscopes, magnetic sensors, and the like that are configured to detect an orientation associated with the user.

An associated device sensor can include any sensors that are associated with a device while using the system. Typical devices may include smartphones, tablets, laptops, mobile computers, smart watches, smart wearables, and the like. It is anticipated that the various sensors associated with these devices can be employed by the system control. For example, a typical smartphone can include an image sensor, an IR sensor, audio sensor, gyroscope, accelerometer, wireless network sensor, fingerprint reader, and more. A typical smart watch may include heart rate sensor, temperature sensor, motion sensor, etc. It is an aspect of the present disclosure that one or more of these associated device sensors may be used by the system.

The biological sensors may include at least one of RF sensors, IR sensors, image sensors and the like that are configured to detect biological entities. For example, an IR sensor may be used to determine that an object, or biological entity, has a specific temperature, temperature pattern, or heat signature. Continuing this example, a comparison of the determined heat signature may be compared to known heat signatures associated with recognized biological entities (e.g., based on shape, locations of temperature, and combinations thereof, etc.) to determine whether the heat signature is associated with a biological entity or an inanimate, or non-biological object.

The wireless signal sensors may include one or more sensors configured to receive wireless signals from signal sources such as Wi-Fi™ hotspots, cell towers, other electronic devices, and satellite positioning systems. Optionally, the wireless signal sensors may detect wireless signals from one or more of a mobile phone, mobile computer, keyless entry device, radio-frequency identification (RFID) device, near field communications (NFC) device, and the like.

Among other things, the sensors as disclosed herein may communicate with each other, with devices, and/or with the control system via the signal carrier network. Additionally, or alternatively, the sensors disclosed herein may serve to provide data relevant to more than one category of sensor information including, but not limited to, combinations of environmental information, patient information, and therapy information to name a few. Further, the communication is secure and configured to happen via encrypted channel/s.

Patient monitoring system or module comprises patient monitoring device, a central or capital equipment and software. Central or capital equipment used in patient monitoring may utilize a complex interconnected system, Printed Circuit Boards (PCBs), and wire harnesses as well as some display/screen/monitor where the data is shared in a usable format. In an embodiment, the patient monitoring central, or capital equipment comprises a computer with a processor, memory, and non-volatile storage such as a hard drive, or solid-state storage media.

Patient monitoring devices typically contain a sensor for capturing important patient information (e.g., heart rate) and an interconnect solution (e.g., PCBs, connectors, wiring, etc.) that can transmit the information to a capital equipment. For example, a pulse oximeter senses and transmits a patient's pulse to the capital equipment as an example of the patient monitoring device component. A patient monitoring device itself collects and sometimes stores vital patient data. The data may then be sent, either wired or wirelessly, to a capital equipment where it is processed, analyzed, stored, and displayed. Hardware devices gather the data, and software makes the data usable. The software, drivers, applications, and programs that process, store, and visually transform the data are often integral parts of any patient monitoring system.

In some embodiments, the patient's ear canal can be an ideal location on or in the human body for a wearable health and environmental monitor. The ear canal is a relatively immobile platform that does not obstruct a person's movement or vision. Devices located along the ear can have access to the inner-ear canal and tympanic membrane (for measuring core body temperature), muscle tissue (for monitoring muscle tension). The ear canal is also at or near the point of exposure to environmental breathable toxicants of interest (volatile organic compounds, pollution, etc.); noise pollution is also experienced by the ear and its assorted pathway to the tympanic membrane called the External Auditory Canal (EAC). Internal to the skull, this location contains a soft tissue which is adjacent to the brain, as such the ear canal serves as an excellent location for mounting neurological and electrical sensors for monitoring brain activity. Furthermore, as the ear canal is naturally designed for capturing or harvesting acoustical energy, the ear canal provides an optimal location for monitoring internal sounds, such as heartbeat, breathing rate, and mouth motion, and one's own voice via bone conduction. In some embodiments, other locations on the body can be outfitted with sensors and operate in conjunction with sensors in an ear canal. For example, some embodiments can optionally use the pinna and earlobe (for monitoring blood gas levels), the region behind the ear (for measuring skin temperature and galvanic skin response), and the internal carotid artery (for measuring cardiopulmonary functioning). The blood gas levels, and skin temperature may also be measured within the ear canal as well. In some embodiments, the sensors can be embedded or formed on or within an expandable element or balloon that is used to occlude the ear canal. Such sensors can include non-invasive contactless sensors that have electrodes for EEGs, ECGs, transdermal sensors, temperature sensors, transducers, microphones, optical sensors, motion sensors or other biometric, neurological, or physiological sensors that can monitor brainwaves, heartbeats, breathing rates, vascular signatures, pulse oximetry, blood flow, skin resistance, glucose levels, and temperature among many other parameters. The sensor(s) can also be environmental, including, but not limited to, ambient microphones, temperature sensors, humidity sensors, barometric pressure sensors, radiation sensors, volatile chemical sensors, particle detection sensors, or other chemical sensors. The sensors can be directly coupled to the processor or wirelessly coupled via a wireless communication system. In some embodiments, an external portion of the earpiece (e.g., an end cap) can include a fingerprint sensor and/or gesture control sensor to detect a fingerprint and/or gesture. Other sensors and analysis can correlate other parameters to confirm the user fits a predetermined or historical profile within a predetermined threshold. For example, a resting heart rate can typically be within a given range for a given amount of detected motion. In another example, a predetermined brainwave pattern in reaction to a predetermined stimulus (e.g., music, sound pattern, visual presentation, tactile stimulation, etc.) can also be found within a given range for a particular person. In yet another example, sound pressure levels (SPL) of a user's voice and/or of an ambient sound can be measured contexts (e.g., in a particular store or at a particular venue as determined by GPS or a beacon signal) to verify and corroborate additional information alleged by the user. The sensors can also detect physiological changes or metabolic changes. In some embodiments, the sensors can include electrodes or contactless sensors and provide for neurological readings including brainwaves. In some embodiments, the earpiece and electrodes or contactless sensors can be used in Evoked Potential Tests. Evoked potential tests measure the brain's response to stimuli that are delivered through sight, hearing, or touch. These sensory stimuli evoke minute electrical potentials that travel along nerves to the brain and can be recorded typically with patch-like sensors (electrodes) that are attached to the scalp and skin over various peripheral sensory nerves; in these embodiments, the contactless sensors in the earpiece can be used instead. For example, the wearable monitoring device may include an impedance plethysmography to monitor blood pressure in real-time. Note that one or more of these physiological sensors can be incorporated within or on the expandable element or balloon in the earpiece sensor.

Each physiological sensor can be configured to detect and/or measure one or more of the following types of physiological information: heart rate, pulse rate, breathing rate, blood flow, heartbeat signatures, cardio-pulmonary health, organ health, metabolism, electrolyte type and/or concentration, physical activity, caloric intake, caloric metabolism, blood metabolite levels or ratios, blood pH level, physical and/or psychological stress levels and/or stress level indicators, drug dosage and/or dosimetry, physiological drug reactions, drug chemistry, biochemistry, position and/or balance, body strain, neurological functioning, brain activity, brain waves, blood pressure, cranial pressure, hydration level, auscultatory information, auscultatory signals associated with pregnancy, physiological response to infection, skin and/or core body temperature, eye muscle movement, blood volume, inhaled and/or exhaled breath volume, physical exertion, exhaled breath, snoring, physical and/or chemical composition, the presence and/or identity and/or concentration of viruses and/or bacteria, foreign matter in the body, internal toxins, heavy metals in the body, blood alcohol levels, anxiety, fertility, ovulation, sex hormones, psychological mood, sleep patterns, hunger and/or thirst, hormone type and/or concentration, cholesterol, lipids, blood panel, bone density, organ and/or body weight, reflex response, sexual arousal, mental and/or physical alertness, sleepiness, auscultatory information, response to external stimuli, swallowing volume, swallowing rate, mandibular movement, mandibular pressure, chewing, sickness, voice characteristics, voice tone, voice pitch, voice volume, vital signs, head tilt, allergic reactions, inflammation response, auto-immune response, mutagenic response, DNA, proteins, protein levels in the blood, water content of the blood, blood cell count, blood cell density, pheromones, internal body sounds, digestive system functioning, cellular regeneration response, healing response, stem cell regeneration response, and/or other physiological information.

Each environmental sensor is configured to detect and/or measure one or more of the following types of environmental information: climate, humidity, temperature, pressure, barometric pressure, light intensity, light frequency, light flicker, light phase, number of people in a vicinity of the person, coughing and/or sneezing sounds from people in the vicinity of the person, loudness and/or pitch from those speaking in the vicinity of the person, and/or other environmental information, as well as location, speaker identity of current speaker, how many individual speakers in a group, the identity of all the speakers in the group, semantic analysis of the wearer as well as the other speakers, and speaker ID. Essentially, the sensors herein can be designed to detect a signature or levels or values (whether of sound, chemical, light, particle, electrical, motion, or otherwise) as can be imagined.

Eye movement tracking: In an embodiment, a device is incorporated with sensors to monitor the patient's eyes and the changes in the eye movement. Eyes may be monitored to find them in an open position or a closed position, monitored for changes in the pupil, monitored for changes in the cornea. These measurements can be fed back to the system. In an embodiment, it is a system that is simultaneously monitoring and checking the patient's health using the eye and the eye movement.

Eye tracking is the process of measuring a point of gaze (where one is looking), the motion of an eye relative to the head, eye position, size of pupil, pupil dilation or constriction, etc. An eye tracker is a device for measuring eye position and eye movement. Eye-trackers measure rotations of the eye in one of several ways. They fall into one of three categories: (i) measurement of the movement of an object (normally, a special contact lens) attached to the eye; (ii) optical tracking without direct contact to the eye; and (iii) measurement of electric potentials using electrodes placed around the eyes. In an embodiment, eye tracking uses a non-contact, optical method for measuring eye motion. Light, typically infrared, is reflected from the eye and sensed by a video camera or some other specially designed optical sensor. The information is then analyzed to extract eye rotation from changes in reflections. Video-based eye trackers typically use the corneal reflection and the center of the pupil as features to track over time. A more sensitive type of eye-tracker, the dual-Purkinje eye tracker, uses reflections from the front of the cornea and the back of the lens as features to track. In an embodiment, it uses a method of tracking image features from inside the eye, such as tracking the retinal blood vessels as the eye rotates. In another embodiment, eye tracking uses electric potentials measured with electrodes placed around the eyes. The eyes are the origin of a steady electric potential field which can also be detected in total darkness and if/when the eyes are closed. It can be modeled to be generated by a dipole with its positive pole at the cornea and its negative pole at the retina. The electric signal that can be derived using two pairs of contact electrodes placed on the skin around one eye is called Electrooculogram (EOG). If the eyes move from a center position towards a periphery, the retina approaches one electrode while the cornea approaches the opposing one. This change in the orientation of the dipole and consequently the electric potential field results in a change in the measured EOG signal. By analyzing EOG signals, changes in eye movement can be tracked. In an embodiment, it uses two separate movement components: a horizontal and a vertical. In another embodiment, it comprises a third EOG component, the radial EOG channel, which is the average of the EOG channels referenced to some posterior scalp electrode. This radial EOG channel is sensitive to the saccadic spike potentials stemming from the extraocular muscles at the onset of saccades and allows reliable detection of even miniature saccades. Saccades are a rapid movement of the eye between fixation points. In an embodiment, the eye movement is tracked using a sensor embedded in a mask worn by the patient.

Brain activity measuring: In an embodiment, monitoring neurological functioning can be accomplished via electrodes or via non-invasive contactless sensors placed at the ear, near the ear, or within the walls of the ear canal and particularly closer to the skull. When such electrodes are placed along the forehead, this process is described as electroencephalography, and the resulting data is called an electroencephalogram (EEG). These electrodes can be either integrated into an earpiece module or connected to an earpiece module, according to some embodiments of the present invention. For example, the balloon can be modified to conform with EEG electrodes or other electrodes for measuring brain waves or neurological activity. For monitoring neurological functioning, a temple earpiece may also be used. Electrodes may be positioned in a temple earpiece region near the temples of a user for direct contact with the skin. In some embodiments, direct contact is not necessary, and the neurological functioning can be monitored capacitively, inductively, electromagnetically, or a combination of these approaches. In some embodiments, brain waves may couple with low frequency acoustic sensors integrated into an earpiece module. In some embodiments, the electrodes in an earpiece can use multimodal electrodes to monitor or measure various parameters. For example, the electrode can be used to monitor one or more of brain activity (EEG), cardiac activity (ECG or EKG), muscular activity (EMG), skin conductivity, breathing, or speech. The multimodal electrode can be used for concurrent and co-located electrical and mechanical signal acquisition.

In an embodiment, it is a mobile wearable electromagnetic brain activity monitor comprising: a wearable frame which is configured to be worn on a person's head, wherein the wearable frame comprises the frame of a pair of eyeglasses, wherein this wearable frame is configured to encircle a portion of the person's head; a plurality of electromagnetic energy sensors which are configured to be held in electromagnetic communication with the person's brain by the wearable frame, wherein these sensors collect data concerning the person's electromagnetic brain activity; and a control unit is part of the wearable frame with one or more components selected from the group consisting of power source and/or power-transducing component, data transmission and data reception component, data memory component, and data processor.

Comfort measuring: One of the parameters that can be monitored is the comfort and relaxation of the patient while receiving the therapy. In an embodiment, stages of the drug therapy are identified and marked. For example, a first stage when the drug infusion therapy starts, a second stage when the drug therapy is in progress and stable, and a third stage when the drug therapy is heading towards end. Each of these stages bring different changes to the human body and is different from one patient to another. In an embodiment, comfort measurement is to ensure that the patient is comfortable in each of the stages of therapy. According to an embodiment, comfort is measured and fed back to the system. Based on the current comfort level, therapy is adjusted in a way to create a change in the comfort level using the feedback. In an embodiment, comfort is measured by measuring the movement of a body part. For example, if the therapy is creating discomfort in the head and the patient is moving, these movements are captured via pressure sensors using at least one of a wearable cap, a wearable mask, and a spread or blanket fitted with sensors on which the patient may lie or cover his body. In an embodiment, the comfort measurement is correlated with vital parameters or physiological parameters. In an embodiment, comfort is measured from the vitals of the patient. When any form of drug is consumed or taken changes in the person taking the drug are almost immediate, for example, any sort of a narcotic type of drug, changes in the cornea, and the pupil and the cornea, etc. are very observable.

In an embodiment, a heated blanket may be automatically deployed to cover the body of a patient when a drop in body temperature is observed. In another embodiment, the room temperature can be adjusted to increase the comfort level of the patient.

In an embodiment, collecting comfort information associated with the user corresponds to the settings of a user on a therapy system and/or setting of a device within the therapy system and/or settings of an area and the settings of the area in terms of ambience, temperature, lights, music, etc., around the system. They may include, but are not limited to, preferred music stations, content applications, listening content, viewing content, content playback settings (e.g., volume, speed, quality, etc.), genres, content consumption habits (e.g., including listening times, associated content, trends, etc.), recording preferences, and/or the like. The comfort information may correspond to one or more comfort settings of the user. Comfort settings can include, but are in no way limited to, at least one preference such as lighting, temperature, air composition, humidity, oxygen levels, background music/noise, etc.

User settings may be stored in the user profile associated with the user. The comfort and/or preferences information can be stored (in user profile associated with the user) in the profile data memory. The profile data memory can be found on a device, a system, attached to a communication network, and/or some other location (e.g., associated with a system, etc.).

In an embodiment, monitoring the brain activity comprises an electroencephalogram (EEG) configured to measure the brain activity and identifying a distinctive brain activity pattern that marks the loss of consciousness or hallucination, wherein EEG is configured to detect electrical activity of the brain of the patient. In an embodiment, the first sensor comprises at least one of an electrocardiogram (ECG) electrode, a respiratory sensor, a sweat sensor, and a temperature sensor. In an embodiment, the pupil color, the pupil dilation, and the pupil constriction are monitored using an eye mask comprising a third sensor. In an embodiment, the patient monitoring module is a wearable jacket. In an embodiment, the devices capturing patient physiological data are gesture controlled, wherein a gesture for a control command execution is predefined.

In an embodiment, the patient monitoring module is portable and is configured to be attached to a surface where the patient is supported. In an embodiment, the patient monitoring module is configured to be integrated to a surface where the patient is supported. In an embodiment, the first sensor is wearable. In an embodiment, the first sensor is wearable and flexible to contour around a body part of the patient. In an embodiment, the physiological condition comprises at least one of a heart rate, a respiratory rate, a blood pressure, a perspiration level, and a body temperature of the patient. In an embodiment, the patient monitoring module is further configured to store monitoring data of the patient to a database.

In an embodiment, the patient monitoring module further comprises artificial intelligent techniques to determine the rate of drug delivery based on the physiological condition of the patient during the session. In an embodiment, the physiological condition is configured to be assessed based on time trend.

In an embodiment, the system is further configured to generate and execute a dosage rule based on the physiological condition of the patient.

In an embodiment, the system is further configured to record feedback of the patient.

In an embodiment, the system further comprising a pre-recording module configured to create individual distributions of the physiological condition of the patient to identify an upper alarm threshold and a lower alarm threshold for the monitoring period.

In an embodiment, the drug monitoring and control module is configured to monitor the quantity of the drug and the rate of drug delivery to the patient continuously.

Figure 8:
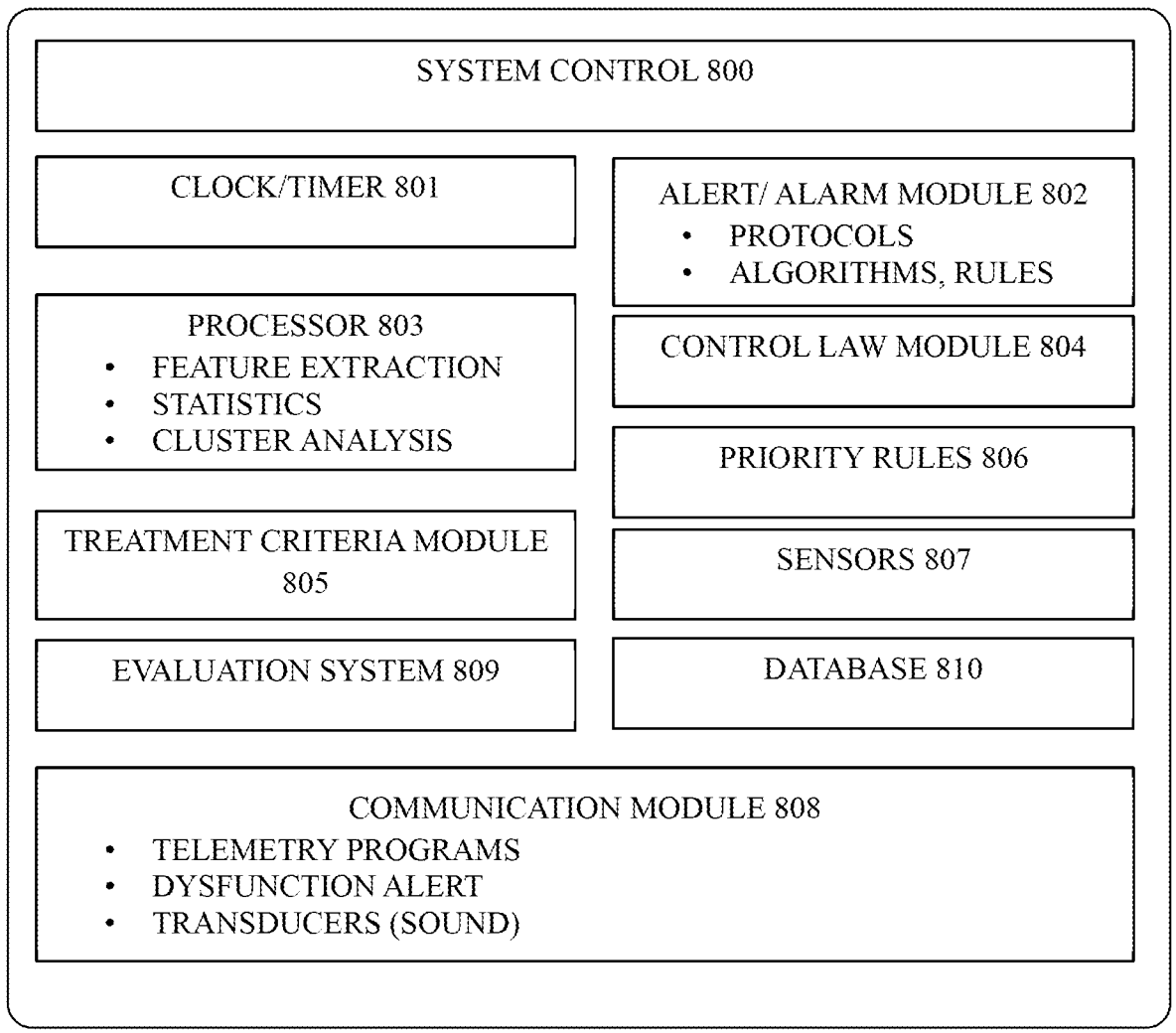
FIG. 8 shows a system control algorithm according to an embodiment of the invention.

FIG. 8 shows a system control algorithm according to an embodiment of the invention. FIG. 8 shows an overall block diagram of an example control system that allows devices to implement features according to an embodiment. The control system implements the treatment program according to the control algorithm of the treatment module. The treatment module contains the treatment program, which may be part of or interact with the control algorithm, and implements the treatment program by communicating with, coordinating, and controlling the modules of the control system and their operations. In an embodiment, the control system serves to realize the treatment program by controlling the stimulation system, sensing system, and evaluation system, according to stimulation, sensing, and evaluation algorithms and associated protocols.

The control system of the timer module can include all or some of these components, although these would be adapted to control the infusion device rather than being located within the infusion device itself. Accordingly, the control system may be implemented either as a single component within the infusion device or as distinct modules distributed throughout a system.

A clock 801 of the system control 800, may be a real-time clock or simply an interval timer, provides time information which may be used in calculating a patient's state or otherwise adjusting therapy. For example, the clock/timer 801 permits the system control 800 to select a protocol for drug therapy.

The system control 800 can utilize an algorithm which compares the current time of the clock to time criteria to determine a patient's state or to determine that some operation is scheduled to occur, for example change in the drug. This time algorithm is part of the treatment program which uses a treatment protocol that has parameter values.

The control system 800 comprises an alert module 802 configured to automatically provide notice to the patient and/or attendant of "alert events", using indication signals. The alarm module or alert module 802 implements an alert algorithm that uses alert rules to provide the alert signal.

The algorithm can assess if alert events have occurred and can be informed that these have occurred from other modules of the system control 800. Alert events include any operation (e.g., medically relevant events) which is defined as requiring that an alert signal be sent, as may be defined in the "alert event set" which is programmed into a database 810, or into the alert module by the algorithm itself. For example, the alert module 802 can automatically send alert signals to notify the nurse or patient about the completion of treatment or a predicted time to complete the treatment. The characteristics of the alert signal or indication signal which is provided can be defined according to the alert algorithm using alert rules of the alert module 802 and can be defined separately in an "alert signal set" or can be part of the alert event set and be stored as information accessed when their respective alert events occur.

The alert module 802 may cause the communication module 808 to send an alert signal to a device or concerned person. An alert signal can be a visual, auditory or vibrotactile alert signal as well as a text-based message. Additionally, the communication module 808, itself contains various transducers to provide alert signals in the form of auditory tones, vibrotactile signals, somatosensory electrical stimulation patterns, and other modes and combinations, according to the alert signal that was selected by the alert module 802. For example, an auditory signal which repeats 3 long beeps 2 times might signify that the system is going into a "sleep" mode, a red light for indicating the treatment session has an emergency that needs to be attended by a nurse.

Alert rules can be modified and changed as required and suitable for the therapy and the patient. The alert module 802 operates according to the alert algorithm and its protocol which includes alert rules. The alert rules can be defined within the alert event set or be otherwise stored or accessed by the alert module 802.

The control system comprises a processing module or processor 803, which can be configured to extract features from the sensed data, as well as calculate statistical properties of these features such as mean, standard deviation and z-scores. The processor 803 can also provide the database 810 with the calculated values to provide self-norm reference data which may be used for such purposes as calculation of the current patient's state and determining if a patient's state has changed, or storing the number of detected events (e.g., alert events) which have occurred over a recent period. The processor 803 can also include filtering, classification, template matching, and other signal analysis modules. The processor can process sensed data for use by the control law module 804 to generate output signals according to the control law selected in the protocol that is implemented by the system control 800. The control law, for example, can provide priority of system level alerts to device level alerts. It can resolve and execute rules when there is a conflict between alert rules or where an anomaly is detected but there is no action coded for the same. The algorithms of the processing module can be utilized by the evaluation system 809 in the evaluation of sensed and processed data.

The system control 800 also contains a treatment criteria module 805 which assists the evaluation system 809 in comparing, for example, processed data or time information to treatment criteria. The treatment criteria module 805 loads treatment criteria values from the database according to the selected evaluation protocol. The treatment criteria module 805 can detect medically relevant events which result in responsive stimulation. The treatment criteria module 805 can include treatment benefit criteria which assist in calculating measures that are reflective of, for example, whether treatment is decreasing or otherwise altering the number or severity of detected medical events, compared to (mean values of) a reference treatment period.

The system control 800 also contains a priority rules module 806, which can implement priority rules. A priority rule can be pre-set or set dynamically according to a patient's state or for different operations. For example, when a drug delivery dosage is modified according to an identified physiological sign, say cardiac activity, and if cardiac activity transitions from bad to worse, causing a detection of a first and then a second alert event, the detection of this alert event can have priority and the system control algorithm can alert for a nurse for immediate presence and/or stop or change the drug to alleviate the patient physiological condition. In an embodiment, the system and all the subsystems and elements of the systems and subsystems have built in manual override or remote system override functions where a human can override the system commands and system control and take in charge completely of the system and operate it as a manual system. In other embodiments, the manual override will be for a momentary control of certain parameters or devices and the system goes back to machine controls.

The control system or system control 800 comprises sensors 807, which determine the patient's state, infusion state, drug device state, environment state, or in general situational awareness using data from the device (such as time data, patient response data, and sensor data) processed through the algorithm.

The control system 800 comprises health-related Artificial Intelligence (AI) applications to analyze relationships between drug dosage and patient outcomes. AI programs are applied to treatment protocol development and patient monitoring. Machine learning assembles techniques that learn from experience to improve their performance at a given task (e.g., clustering, classification, prediction). Model performance is evaluated during the learning process to improve it by estimating algorithm parameters. K-means clustering, logistic regression, and principal component analysis methods may be used to analyze the data using artificial intelligence techniques. In an embodiment, machine learning based prediction models predict opioid overdose of patients based on the history of patients' electronic health records (EHR). Random forest method, logistic regression, decision tree, gradient boosting, and deep learning methods may be employed in the prediction models. In an embodiment, K-Means clustering, an unsupervised algorithm, is used to explore drug-drug interactions that might be of concern to a patient's health. In another embodiment, the prediction model can predict drug dosage protocol from the patient's electronic health record. In an embodiment, reduced tolerance due to a recent period of abstinence is considered into the model.

Figure 9:
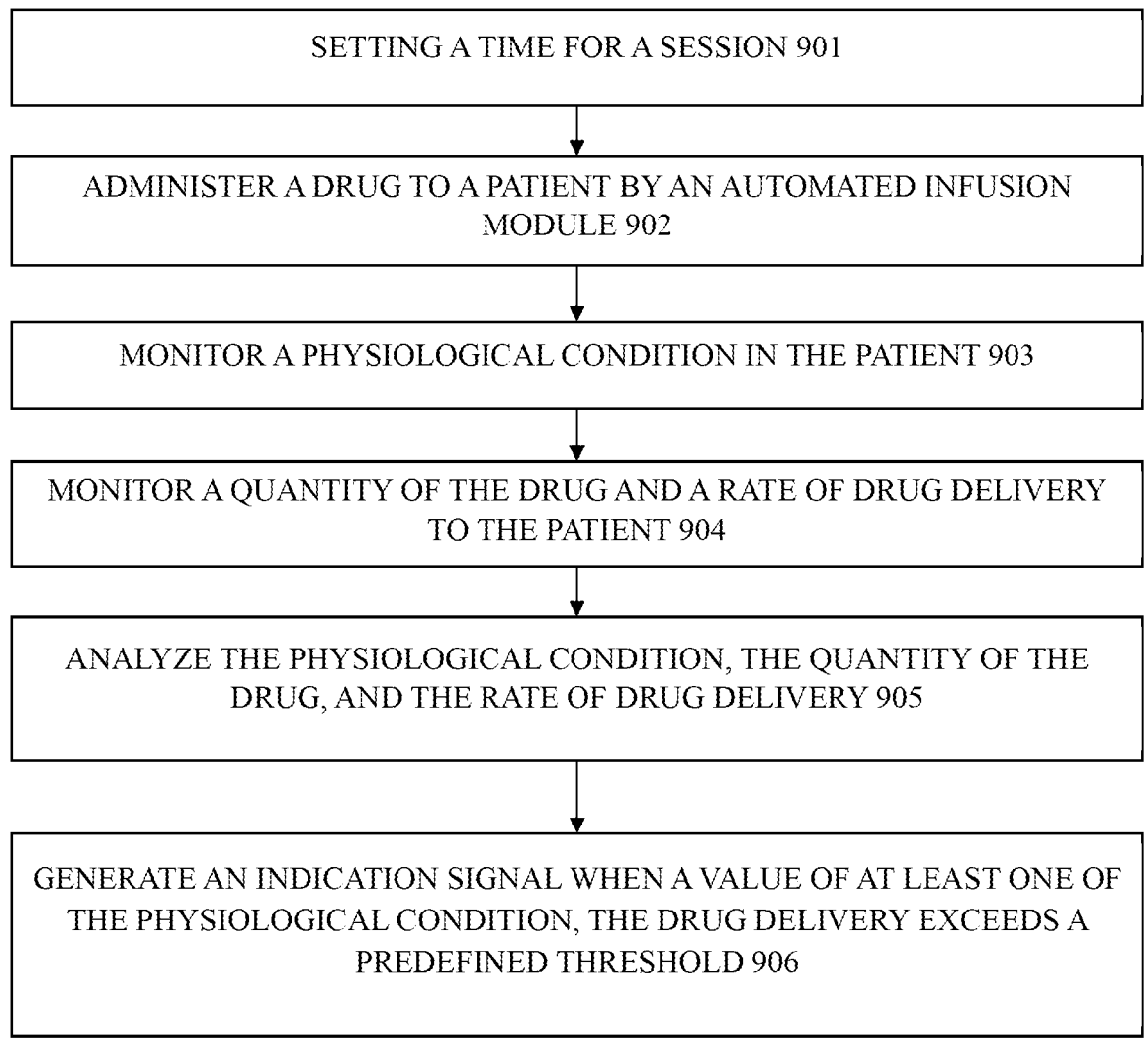
FIG. 9 shows method steps for implementing infusion and patient monitoring in the system according to an embodiment.

FIG. 9 shows method steps for implementing infusion and patient monitoring in the system according to an embodiment. According to an embodiment it is a method, comprising the steps of; setting a time for a session 901, administering a drug to a patient by an automated infusion module 902, monitoring a physiological condition in the patient 903, monitoring a quantity of the drug and a rate of drug delivery to the patient 904, analyzing the physiological condition, the quantity of the drug, and the rate of drug delivery 905, generating an indication signal when a value of at least one of the physiological condition, the quantity of the drug, and the rate of drug delivery exceeds a predefined threshold 906, controlling a quantity of the drug and a rate of drug delivery to the patient based on the physiological condition and changing the time for the session based on the physiological condition, and wherein the method is configured for remote monitoring of the patient and the session.

Data Storage, Data Access and Authentication

In an embodiment, the system further comprises an authentication module configured to check credentials of the user from a database of authorized users.

In an embodiment, the system determines the baseline biometric profile associated with at least one user and stores the determined baseline biometric profile in a user profile memory associated with at least one user. In an embodiment, the system determines the presence of at least one user comprising detecting a person via at least one image sensor associated with the system.

In an embodiment, determining the identity of the at least one user further comprises: identifying facial features associated with the person detected via at least one image sensor; and determining whether the identified facial features associated with the person match user characteristics stored in a memory. In an embodiment, the data associated with the at least one user is provided by a sensor worn by the at least one user.

Cyber Security

In an embodiment, the system may comprise a cyber security module, a communication module, a server, and a database.

In one aspect, a secure communication management (SCM) computer device for providing secure data connections in the healthcare environment is provided. The SCM computer device includes a processor in communication with memory. The processor is programmed to receive, from a first user computer device, a first data message from a user or an attendant. The first data message is in a standardized data format. The processor is also programmed to analyze the first data message for potential cyber security threats. If the determination is that the first data message does not contain a cyber security threat, the processor is further programmed to convert the first data message into a first data format associated with the healthcare environment and transmit the converted first data message to the healthcare system using a first communication protocol associated with the healthcare system.

According to an embodiment, secure authentication for data transmissions comprises, provisioning a hardware-based security engine (HSE) located in communications system, said HSE having been manufactured in a secure environment and certified in said secure environment as part of an approved network; performing asynchronous authentication, validation and encryption of data using said HSE, storing user permissions data and connection status data in an access control list used to define allowable data communications paths of said approved network, enabling communications of the communications system with other computing system subjects to said access control list, performing asynchronous validation and encryption of data using security engine including identifying a user device (UD) that incorporates credentials embodied in hardware using a hardware-based module provisioned with one or more security aspects for securing the system, wherein security aspects comprising said hardware-based module communicating with a user of said user device and said HSE.

In an embodiment, there is a cyber security module embedded in each of the layers namely Human Layer, Perimeter Layer, Network Layer, Endpoint Layer, Application Layer, Data Layer, and Mission Critical Layer. Each layer represents a different stage in network communication, from a human typing on a keyboard to the data system used for applications.

Figure 10A:
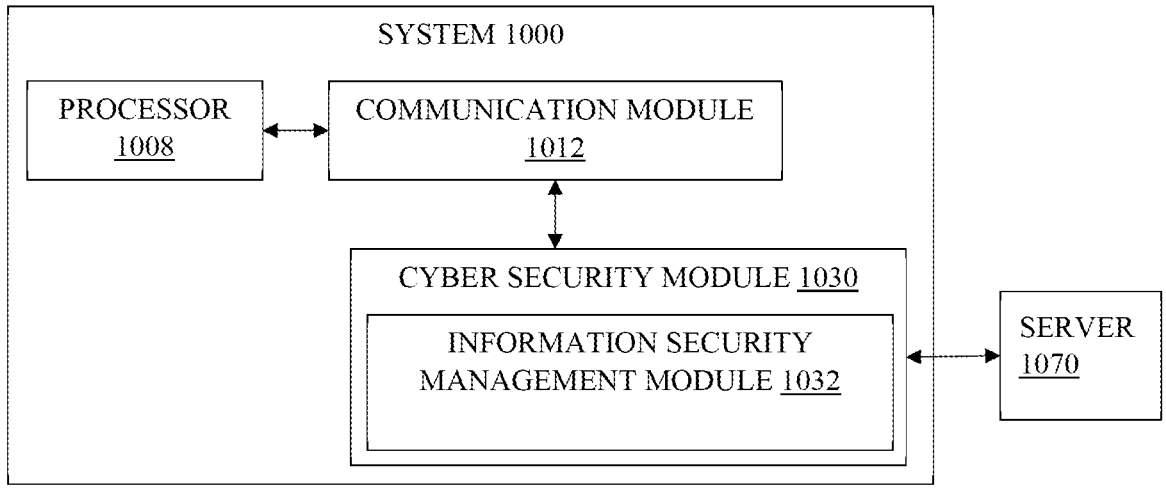
FIG. 10A shows a block diagram of the cyber security module in view of the system and server.

In an embodiment, FIG. 10A shows the block diagram of the cyber security module. The communication of data between the system 1000 and the server 1070 through the communication module 1012 is first verified by the information security management module 1032 before being transmitted from the system to the server or from the server to the system. The information security management module is operable to analyze the data for potential cyber security threats, encrypt the data when no cyber security threat is detected, and transmit the data encrypted to the system or the server.

Figure 10B:
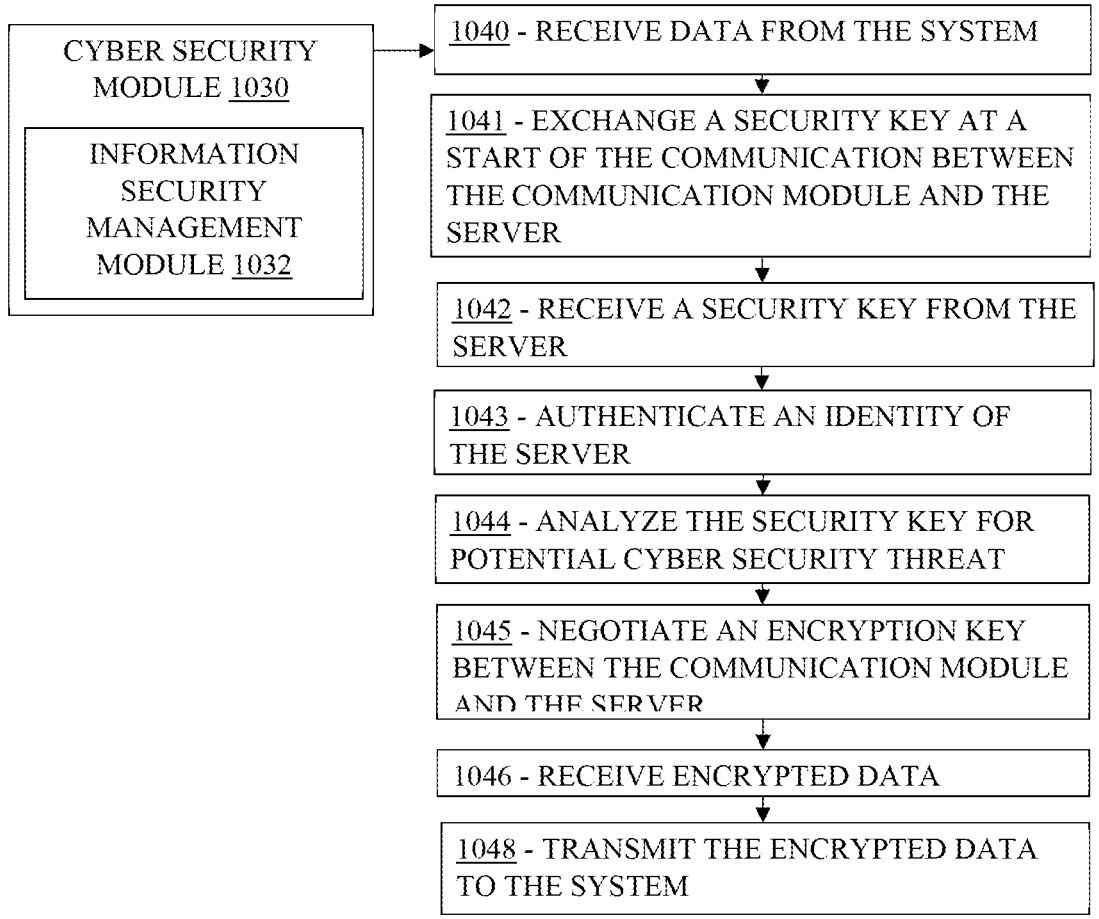
FIG. 10B shows an embodiment of the cyber security module.

In an embodiment, the cyber security module further comprises an information security management module providing isolation between the system and the server. FIG. 10B shows the flowchart of securing the data through the cyber security module 1030. At step 1040, the information security management module is operable to receive data from the system, for example, at least one of an input interface, the drug storage, and the database. At step 1041, the information security management module exchanges a security key at a start of the communication between the communication module and the server. At step 1042, the information security management module receives a security key from the server. At step 1043, the information security management module authenticates an identity of the server by verifying the security key. At step 1044, the information security management module analyzes the security key for potential cyber security threats. At step 1045, the information security management module negotiates an encryption key between the communication module and the server. At step 1046, the information security management module encrypts the data. At step 1047, the information security management module transmits the encrypted data to the server when no cyber security threat is detected.

Figure 10C:
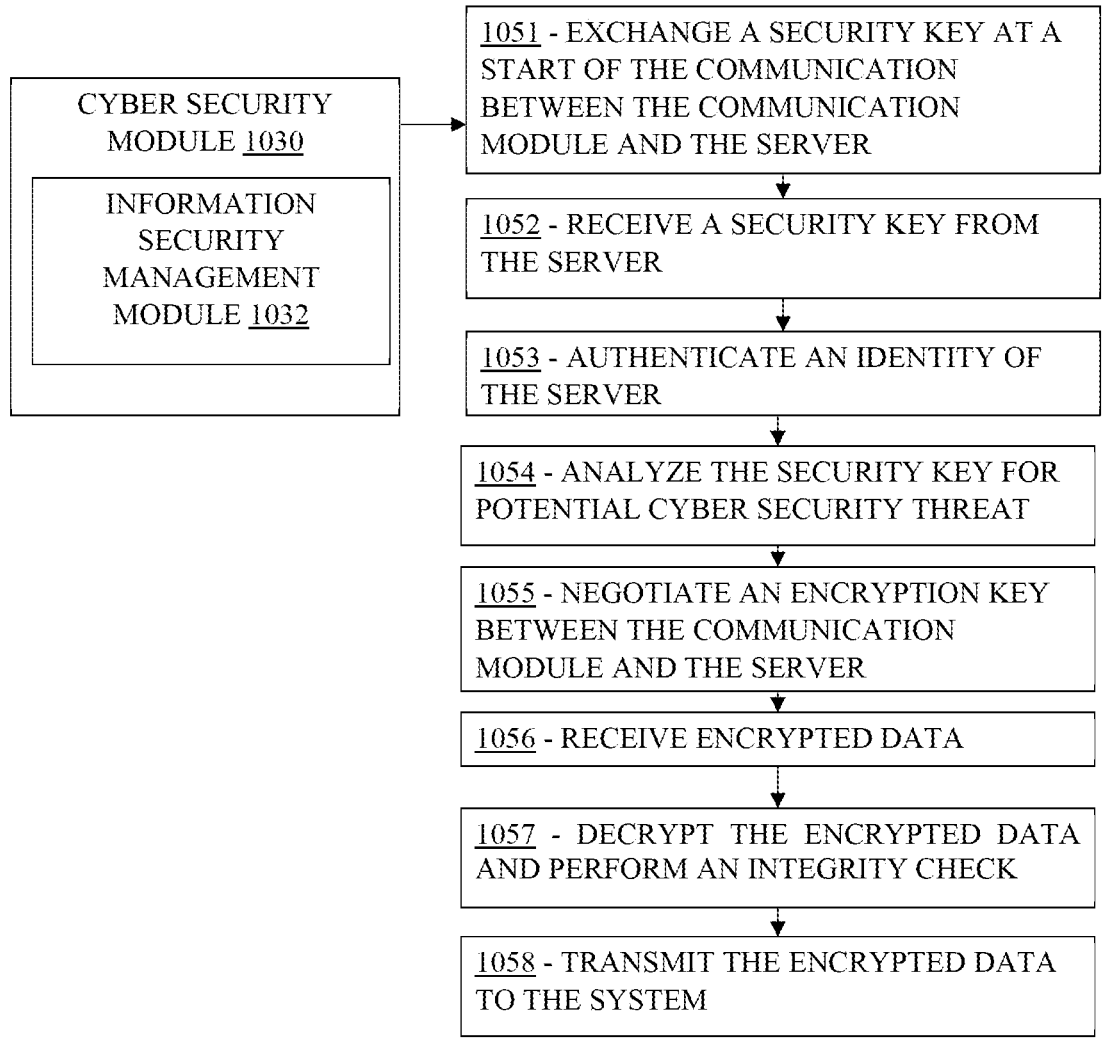
FIG. 10C shows another embodiment of the cyber security module.

In an embodiment, FIG. 10C shows the flowchart of securing the data through the cyber security module 1030. At step 1051, the information security management module is operable to: exchange a security key at a start of the communication between the communication module and the server. At step 1052, the information security management module receives a security key from the server. At step 1053, the information security management module authenticates an identity of the server by verifying the security key. At step 1054, the information security management module analyzes the security key for potential cyber security threats. At step 1055, the information security management module negotiates an encryption key between the system and the server. At step 1056, the information security management module receives encrypted data. At step 1057, the information security management module decrypts the encrypted data, performs an integrity check of the decrypted data. At step 1058, the information security management module transmits the decrypted data to the system, for example, at least one of output interface, drug storage, and the database through the communication module when no cyber security threat is detected.

In an embodiment, the integrity check is a hash-signature verification using a Secure Hash Algorithm 256 (SHA256) or a similar method. A cryptographic hash (sometimes called 'digest') is a kind of 'signature' for a text or a data file. SHA256 generates an almost-unique 256-bit (32-byte) signature for a text.

In an embodiment, the information security management module is configured to perform asynchronous authentication and validation of the communication between the communication module and the server.

In an embodiment, a perimeter network provides an extra layer of protection. In an embodiment, the perimeter network protects the system from a cyber security threat by using a plurality of firewalls. Usually, a perimeter network is the final step a packet takes traversing one of the system's networks on its way to the internet; and conversely the first network encountered by incoming traffic from the Internet to the system.

In an embodiment, a demilitarized zone (DMZ) network functions as a subnetwork containing an organization's exposed, outward-facing services. It acts as the exposed point to an untrusted network, commonly the Internet. A DMZ network will add an extra layer of security to an organization's local area network. It is a protected and monitored network node that faces outside the internal network and can access what is exposed in the DMZ, while the rest of the organization's network is safe behind a firewall. A DMZ Network gives organizations extra protection in detecting and mitigating security breaches before they reach the internal network, where valuable assets are stored. All services accessible to users on communicating from an external network can and should be placed in the DMZ, if one is used. The most common services include, but are not limited to, web servers, mail servers, file transfer protocol (FTP) servers.

In an embodiment, the information security management module is configured to raise an alarm if a cyber security threat is detected. In an embodiment, the information security management module is configured to discard the encrypted data received if the integrity check of the encrypted data fails.

In an embodiment, the information security management module is configured to check the integrity of the encrypted data by checking accuracy, consistency, and any possible data loss during the communication through the communication module.

In an embodiment, the information security management module is configured to perform asynchronous authentication and validation of the communication between the communication module and the server.

In an embodiment, the server is physically isolated from the system through the information security management module. When the system communicates with the server as shown in FIG. 10A, identity authentication is firstly carried out on the system and the server. The system is responsible for communicating/exchanging a public key of the system and a signature of the public key with the server. The public key of the system and the signature of the public key are sent to the information security management module. The information security management module decrypts the signature and verifies whether the decrypted public key is consistent with the received original public key or not. If the decrypted public key is verified, the identity authentication is passed. Similarly, the system and the server carry out identity authentication on the information security management module. After the identity authentication is passed on to the information security management module, the two communication parties, the system, and the server, negotiate an encryption key and an integrity check key for data communication of the two communication parties through the authenticated asymmetric key. A session ID number is transmitted in the identity authentication process, so that the key needs to be bound with the session ID number; when the system sends data to the outside, the information security gateway receives the data through the communication module, performs integrity authentication on the data, then encrypts the data through a negotiated secret key, and finally transmits the data to the server through the communication module. When the information security management module receives data through the communication module, the data is decrypted first, integrity verification is carried out on the data after decryption, and if verification is passed, the data is sent out through the communication module; otherwise, the data is discarded.

In an embodiment, the identity authentication is realized by adopting an asymmetric key with a signature.

In an embodiment, the signature is realized by a pair of asymmetric keys which are trusted by the information security management module and the system, wherein the private key is used for signing the identities of the two communication parties, and the public key is used for verifying that the identities of the two communication parties are signed.

In an embodiment, the identity authentication is that both communication parties need to authenticate their own identities through a pair of asymmetric keys, and a task in charge of communication with the information security management module of the system is identified by a unique pair of asymmetric keys.

In an embodiment, the dynamic negotiation key is encrypted by adopting an Rivest-Shamir-Adleman (RSA) encryption algorithm. RSA is a public-key cryptosystem that is widely used for secure data transmission. The negotiated keys include a data encryption key and a data integrity check key.

In an embodiment, the data encryption method is a Triple Data Encryption Algorithm (3DES) encryption algorithm. The integrity check algorithm is a Hash-based Message Authentication Code (HMAC-MD5-128) algorithm. When data is output, integrity check calculation is carried out on the data, the calculated Message Authentication Code (MAC) value is added with the head of the value data message, then the data (including the MAC of the head) is encrypted by using a 3DES algorithm, the head information of a security layer is added after the data is encrypted, and then the data is sent to the next layer for processing.

In an embodiment the next layer refers to a transport layer in the Transmission Control Protocol/Internet Protocol (TCP/IP) model.

In an embodiment, when the receiving side finds an authentication error or a MAC decryption error, it is necessary to send a fatal error message to the transmitting side and close the connection.

The information security management module ensures the safety, reliability, and confidentiality of the communication between the system and the server through the identity authentication when the communication between the two communication parties starts the data encryption and the data integrity authentication in the communication process. The method is particularly suitable for an embedded platform which has less resources and is not connected with a Public Key Infrastructure (PKI) system and can ensure that the safety of the data on the server of the drug storage cannot be compromised by hacker attack under the condition of the Internet by ensuring the safety and reliability of the communication between the system and the server in the system for smart storage.

In an embodiment, a system hardening strategy is implemented to prevent at least one attack. An attack graph analysis may be used to help analyze network vulnerability. Once an attack graph of conditions and/or exploits (e.g., at least one goal condition, at least one initial condition, at least one exploit) is obtained, allowable actions that may harden the conditions may be obtained. Costs associated with the allowable actions may also be obtained. Recommended actions to harden the network with respect to one or more goal conditions may be determined.

Figure 11:
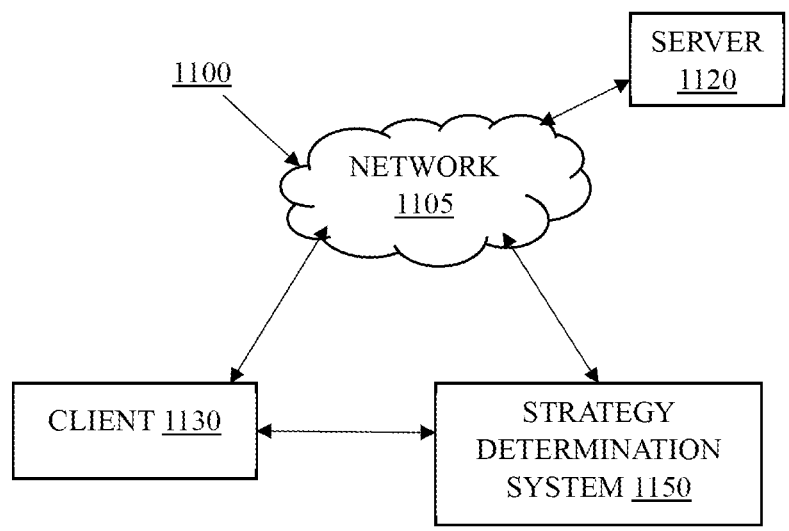
FIG. 11 is an example system where a system hardening strategy may be implemented according to an embodiment of the invention.

FIG. 11 is a system 1100 according to an embodiment of the invention. In this example, the system 1100 may comprise a network 1105 (e.g., the Internet, an intranet) wherein one or more computers 1120 (e.g., server, client) may communicate with one another. A strategy determination system 1150 may communicate with the client and/or the server. The strategy determination system 1150 may obtain an attack graph of conditions and/or exploits (e.g., using known techniques), obtain allowable actions that may remove one or more initial conditions to harden the network with respect to one or more goal conditions; obtain costs associated with the allowable actions, and determine recommended system hardening strategies to efficiently harden the network with respect to the goal condition(s), each system hardening strategy consisting of one or multiple allowable actions. As attackers may leverage complex interdependencies of network configurations and vulnerabilities to penetrate seemingly well-guarded networks, in an embodiment, the recommended actions may consider attacker exploits in isolation and/or in combination. Attack graphs may reveal such threats by enumerating potential paths that attackers can take to penetrate networks. This may help determine whether a given set of system hardening measures provides safety for given critical resources.

System hardening goal conditions may have a corresponding impact on removing paths in the attack graph. In addition, system hardening solutions that are optimal with respect to some notion of cost and/or time may be determined. Such system hardening solutions prevent the attack from succeeding, while minimizing the associated costs.

The strategy determination system 1150 may comprise: a determine allowable actions module; an associate costs module; a determine recommended actions module; or an approximation module; or any combination thereof. In the strategy determination method, an attack graph comprising conditions and/or exploits may be obtained, allowable actions that remove one or more initial conditions may be obtained, costs associated with the allowable actions may be obtained, and recommended strategies comprising allowable actions may be determined based upon costs and/or time constraints.

Spyware is a type of malware that may be installed on computers and collects bits of information at a time about users without their knowledge. The presence of spyware is typically hidden from the user and may be difficult to detect. Spyware programs may collect various types of personal information, such as Internet surfing habits and sites that have been visited but may also interfere with user control of the computer in other ways, such as installing additional software and redirecting Web browser activity.

Figure 12:
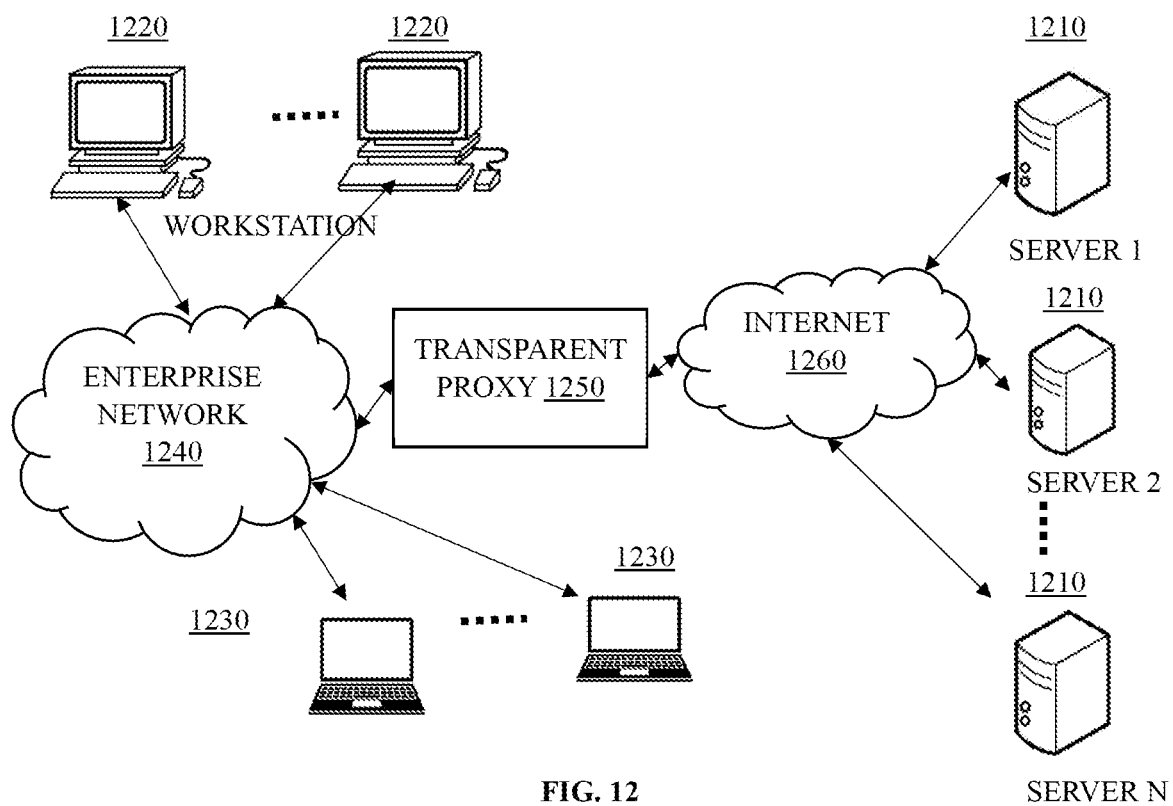
FIG. 12 shows an architecture of a network using a transparent proxy in an Enterprise network as per an aspect of an embodiment of the present invention for active malware detection.

Passive detection may identify a fraction of the malware that is collected in an enterprise network but may not identify all of them. Embodiments of the present invention utilize active detection mechanism(s). The active detection mechanism(s) may also be called Active Content Challenges and may be implemented using a transparent proxy. FIG. 12 shows the architecture of a network using an embodiment of the transparent proxy 1250 in an Enterprise network 1240 including workstations 1220 and laptops 1230. The architecture may be fully transparent and may not require any application or network modifications both for client applications and servers and may accommodate various protocols including HTTP, encrypted HTTP (HTTPS) and Voice over IP (VOIP) protocols. The transparent proxy 1250 may mediate all traffic both encrypted and unencrypted when an application initiates a communication with a server 1210 connected to Internet 1260 outside the enterprise. Communication may pass through the firewall while being examined and analyzed by the transparent proxy 1250. According to an embodiment, a transparent proxy may be in a laptop or workstation. The transparent proxy may mediate all traffic both encrypted and unencrypted when an application initiates a communication with a remote server connected to the internet.

The transparent proxy 1250 may intercept outbound requests and issue Active Content Challenges to the requesting application. The principle is similar to Turing puzzles and Captchas, however, rather than trying to distinguish a human from software, the objective is to distinguish legitimate software from malware. Thus, unlike existing mechanisms that demand end-users to be involved in the identification process by solving a puzzle, the approach in this embodiment requires no user involvement or application modification. The transparent proxy for malware detection may include a monitor module, a protocol determination module, a challenge generation module, a response determination module, and a data control module. The transparent proxy may include interfaces for receiving and transmitting applications traffic and remote server traffic. The transparent proxy may be located on a network edge or on a laptop or workstation and may examine outgoing traffic. In general, the approach frustrates the communication of the malware by injecting traffic that the malware is incapable of parsing and generating a valid response contrary to the legitimate application.

In an embodiment, a secure virtual browsing environment is provided which includes creating a virtual browsing environment with a virtualized operating system sharing an operating system kernel of a supporting operating system and executing the browser application within the virtual browsing environment. Another embodiment includes receiving a website selection within a browser application, determining if the website selection corresponds to a secure bookmark, and creating a second virtual browsing environment and executing the browser application within the second virtual browsing environment to access the website selection when the website selection corresponds to a website specified as a secure bookmark. Another embodiment includes monitoring operation of the operating system within the at least one virtual browsing environment, determining when the operation of the operating system includes potential malicious activity, and terminating the virtual browsing environment when the operation includes potential malicious activity.

Figure 13A:
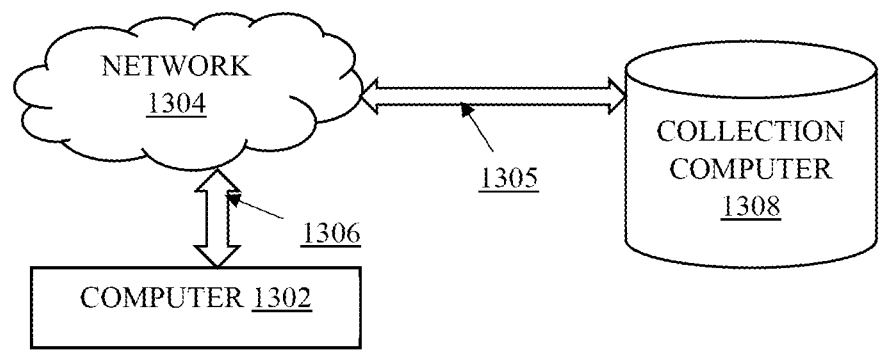
FIG. 13A illustrates a system for providing a virtual browsing environment according to an aspect of an embodiment of the invention.

FIG. 13A illustrates a system 1300 for providing a virtual browsing environment according to one embodiment of the invention. As described below, embodiments of the system 1300 may provide a virtual browsing environment for executing a browser application on a computer. By executing the browser application within a separate virtual browsing environment, other applications, data, and modules of the computer may be protected from any malicious activity associated with the execution of the browser application. In addition, because in some embodiments only the browser application may be executed within the virtual browsing environment, malicious activity associated with the execution of the browser application may be easily detected. The system 1300 may include at least one computer 1302, at least one network 1304, and at least one collection computer ("CC") 1308 and other components. The computer 1302 and the network 1304 may be connected by a connection 1306, and the network 1304 and the collection computer 1308 may be connected by a connection 1305. The collection computer 1308 may receive data from the network 1304 over the connection 1305. In some embodiments, the collection computer 1308 may also send data to the network 1304 or one or more computers or networks. The collection computer 1308 may also include hardware, such as one or more memory modules, one or more processors, and one or more input/output modules. In addition, the collection computer 1308 may include an operating system to manage the hardware. In some embodiments, the collection computer 1308 may also include a database that stores data received from the network 1304. The data included in the database may be stored in the collection computer's 1308 one or more memory modules, and the data may be managed by a database management application.

Figure 13B:
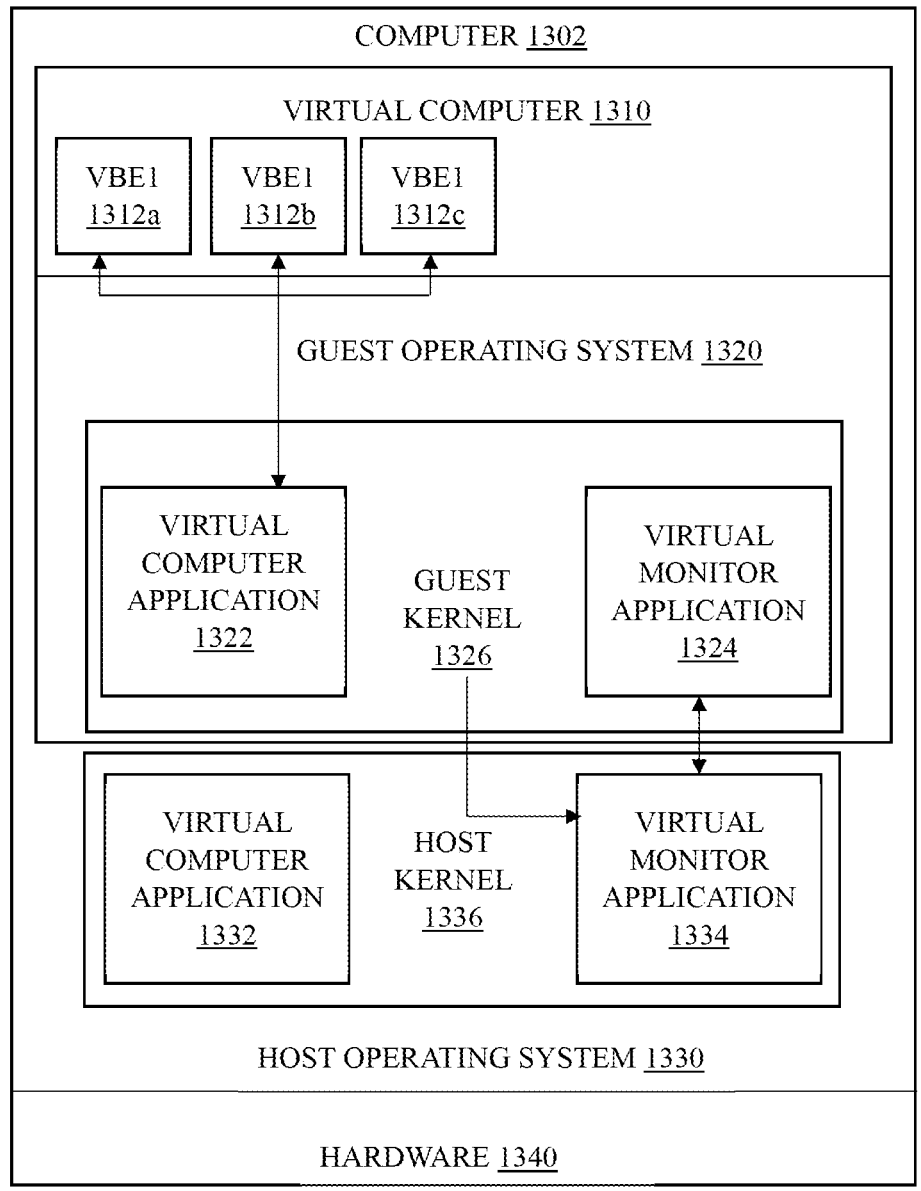
FIG. 13B illustrates a computer included in the system of FIG. 13A, according to an embodiment of the invention.

FIG. 13B illustrates the computer 1302 of FIG. 13A which includes a host operating system 1330 that provides an interface between the hardware 1340 and a user operating the computer 1302. The host operating system 1330 may be stored in the one or more memory modules and may be executed on the one or more processors included in the hardware 1340. The host operating system 1330 may include at least one host kernel 1336. The host kernel 1336 may manage the communication between the hardware 1340 and applications executed by the hardware 1340. The host kernel 1336 may use the virtual control application (VCA) 1334 to create and manage a virtual computer. Accordingly, the VCA 1334 may provide virtualization functionality. The host kernel 1336 may also include a shared preference directory 1332, which may store preferences for an application, such as a browser application. It should be understood that the one or more memory modules included in the hardware 1340 may store other applications besides those explicitly shown in FIG. 13B. In addition, the functionality provided by the applications stored in the one or more memory modules may be combined and distributed in various configurations.

In operation, as shown in FIG. 13B, the host kernel 1336 may execute the VCA 1334 to create a virtual computer 1310. The virtual computer 1310 may include its own guest host operating system 1320 with a guest kernel 1326. The guest operating system 1320 and guest kernel 1326 may operate similar to the host operating system 1330 and host kernel 1336. This type of virtualization where a generally complete copy of an operating system is provided within a virtual computer is generally referred to as "full virtualization." Outside of the virtual computer 1310, the host operating system 1330 may continue to interact and manage the hardware 1340, while the guest operating system 1320 also may interact and manage the hardware 1340. Therefore, the virtual computer 1310 may create a second, isolated computing environment within the computer 1302. Each computing environment may execute different applications, access data from different locations in a memory module or from different memory modules, provide different operating systems, or combinations thereof. Creating the virtual computer 1310 may provide isolation between computing performed within the virtual computer 1310 and computing performed outside the virtual computer 1310 through the host operating system 1330. For example, the virtual computer 1310 may be unaware of any computing performed outside of the virtual computer 1310. Accordingly, an application executed within the virtual computer 1310 generally cannot access an application executed outside the virtual computer 1310.

As shown in FIG. 13B, the guest kernel 1326 may include a virtual computer control application ("VCCA") 1322 and a virtual computer monitor application ("VCMA") 1324. The VCCA 1322 may manage the operation of the virtual computer 1310. For example, as shown in FIG. 13B, the VCCA 1322 may create one or more virtual browsing environments ("VBE") 1312 (e.g., VBE 1 1312 *a*, VBE 2 1312 *b*, and VBE 3 1312 *c*). Once created, the VCMA 1324 may monitor the operation of each VBE 1312 and may report each VBE's operation to the VCA 1334. To create a VBE 1312, the VCCA 1322 may use one or more virtualization modules or applications, such as OpenVZ, UnionFS patches, Solaris Zones, BSD Jail, or combinations thereof.

It is known that internet-enabled applications run side-by-side with all other desktop and system software with the privileges of the user. As a result, when a compromise occurs through the Internet, the entire system can be compromised by a single vulnerability in an Internet-enabled software such as a Web browser or an email client. By simply browsing to a Web page, a user can compromise their system, sometimes irreversibly.

In an embodiment, the system works by launching a virtual machine for each Internet-enabled or untrusted application that is started. The virtual machine provides a pristine guest operating system (OS) for the Internet-enabled or untrusted application that is launched. This operating system may be an operating system unmodified from the original version delivered by the manufacturer or another version suitably configured for the task of running intended applications. The virtual machine and its guest operating system may be temporally limited to exist only for the duration of the session of the application. When the user exits the application, the virtual machine can be destroyed. For the duration of the session, the virtual machine provides an isolated environment from the host machine from which it is launched. The virtual machine provides a level of isolation from the host machine that is the equivalent to running a physically separate machine from the host machine. Any attacks that occur on the machine via an Internet connection can compromise only the virtual machine that is started up for that session. When the session is terminated, so is the virtual machine and the compromise. With each new session, a pristine new virtual machine is started up, meaning that any malicious software that was downloaded or planted during a prior session is no longer present. The underlying host operating system does not need to maintain an Internet connection. As a result, Internet-based attacks have a very limited ability to compromise the host operating system.

Figure 14:
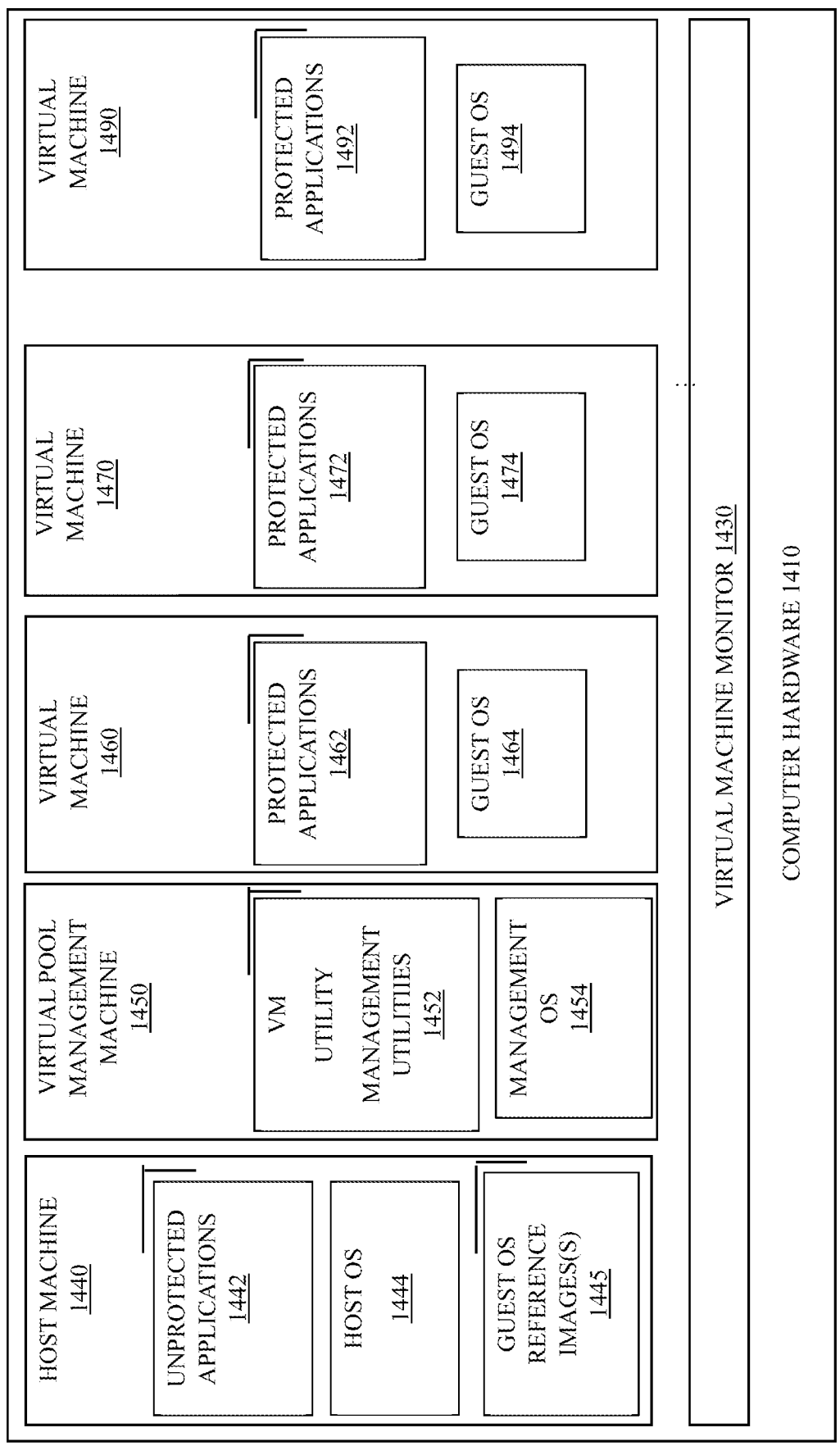
FIG. 14 is a block diagram of a virtual machine architecture of an aspect of an embodiment of the present invention to prevent malicious software attack.

According to an embodiment, an architecture shown in FIG. 14 uses the standard virtual machine architecture with the Virtual Machine Monitor (VMM) 1430 running on the computer hardware 1410, and host operating systems (1444, 1454, 1464, 1474, and 1494) running on top of the VMM 1430. A host operating system (OS) 1444 is defined as the default machine the user normally uses and is the machine whose desktop is presented to the user. Guest OSs (1464, 1474 and 1494) are created by request when a protected application (1462, 1472 and 1492) is launched, or created in advance to enable higher performance when launching protected applications (1462, 1472 and 1492) into pre-instantiated guest OSs (1464, 1474 and 1494). A Management VM 1450 may be bootstrapped along with the Host OS 1444 and a reference guest OS image 1445 that is used for clones of the guest OS reference image 1445. The Management VM 1450 is used for command, control, and lifecycle maintenance of the guest OSs (1464, 1474 and 1494) based on the instructions from the host OS 1444. The number of guest OSs instantiated may be dependent on the number of protected applications launched and the performance limits of the underlying hardware. The VMM 1430 and VM 1450 should support live capture of the full system state in a file for subsequent replay. This file is called a "snapshot" of system state.

The host operating system 1444 may be configured for higher security so that it is unable to make Internet connections itself. The guest operating systems (1464, 1474 and 1494) may be free to make direct Internet connections; however, they should be restricted from freely accessing the host operating system 1444 by the virtual machine monitor 1430 that runs in its own hardware protection domain which provides hardware-equivalent strong isolation between the virtual machine and its host operating system. The guest operating systems (1464, 1474 and 1494), which are pristine builds of the OS, should also be "root secure", which means that even if one of the guest operating systems (1464, 1474 and 1494) is compromised to a root user level or the kernel itself is compromised, the host operating system 1444 itself should not be compromised by the compromised guest operating system. Once a guest operating system is destroyed (upon closure of the protected application that started the guest OS), the compromise is now removed from the system.

As mentioned earlier, a reference guest OS image 1445 may be booted along with the host OS 1444. A snapshot of the reference guest OS image 1445 may be taken, then used to derive subsequent VM images by cloning it, i.e., creating a replica image of the reference guest OS. When a new untrusted application is to be started, a dispatch instruction is sent from the Host OS to the Virtual Pool Management Machine 1450, which then creates a VM for the application using the reference guest OS image, if the VM has not already been created. By cloning and pre-booting reference images, the response time for instantiating the application should be on par or even faster than the usual response time for starting a new application for users.

As described, FIG. 14 shows an embodiment of the present invention where virtual machines (VM) monitor 1430 runs directly on computer hardware 1410. In this embodiment, every host machine (1440, 1450, 1460, 1470 and 1490) is essentially a guest machine to the computer hardware. In this setup, the unprotected host applications 1442 run on the host machine 1440 natively and the host operating system 1444 runs these unprotected host applications 1442. In contrast, the guest virtual machines 1460, 1470 and 1490 run protected applications (1462, 1472, and 1492 respectively) that may talk to a network under guest operating systems (1464, 1474 and 1494 respectively).

The guest operating systems 1464, 1474, and 1494 are each cloned from one of the guest operating system images(s) 1445, and the images 1445 should be pristine snapshots of a running operating system. To increase speed, the snapshots may also include running applications. For example, an image 1445 of an operating system for an email virtual machine can include a copy of an email application running under the operating system.

The virtual pool management machine 1450 runs a series of virtual machine management utilities 1452 under a management operating system 1454. These utilities 1452 include functions that: create, destroy, put to sleep, and wake up virtual machines. The utilities also maintain a list that matches applications to virtual machines. In other embodiments, these same functions may be performed by pool management utilities running on a host machine.

Figure 15:
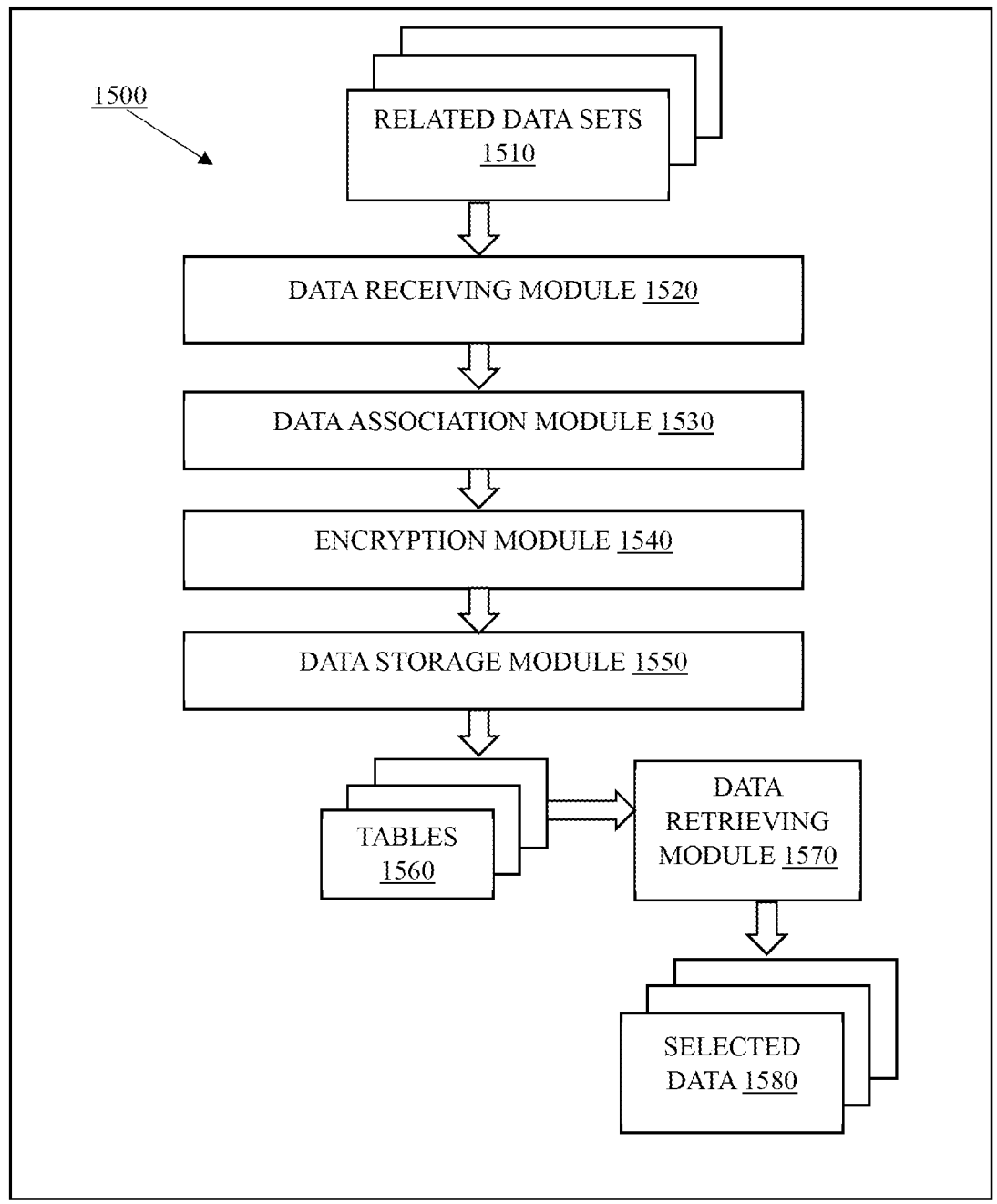
FIG. 15 is a block diagram for securing sensitive data associations for related data values of an aspect of an embodiment of the present invention.

In an embodiment, sensitive data associations for related data values are protected. FIG. 15 is a block diagram of a system 1500 for protecting sensitive data associations according to an aspect of an embodiment of the present invention. The block diagram shows a multitude of modules. As shown, the system includes a data receiving module 1520 configured to receive a set(s) of related data values 1510. The set(s) of related data values 1510 preferably include at least a first data value and a second data value. The system normally operates against rule(s) that indicate which data value associations need to be kept secret. In the absence of such a rule, a default rule may be used such as the association of the first data value and the second data value needs to be kept secret.

A data association module 1530 may be configured to associate the first data value to a first data field; and the second data value to a second data field. An encryption module 1540 may then create first encrypted data by encrypting the first data value using a first encryption key; and create second encrypted data by encrypting the second data value using a second encryption key. A data storage module 1550 is configured to store: the first data value in a first data table 1560; the second data value in a second data table 1560; the first encrypted data in the second table 1560; and the second encrypted data in the first table 1560.

A data retrieving module(s) 1570 may be used to retrieve: the first data value by decrypting the first encrypted data using a first decryption key and/or the second data value by decrypting the second encrypted data using a second decryption key. As with the method embodiments, there are many possibilities for the encryption and decryption keys. The encryption key and the decryption key may be the same symmetric key. The encryption keys may be different or the same. Similarly, the decryption keys may be the same or different. The choice of keys should be made carefully to ensure that the data relationships in the rule(s) be kept secret. In some embodiments, the rule may be received from an external source. In the absence of an external rule, an internal rule or a default rule may be used.

In an embodiment, there is a tool for storing data records in a data store that is scalable and that allows a user to define their encryption and relieves a user from the task of managing keys used for data security. In an embodiment, application data and associated encryption key(s) are stored on at least k+1 remote servers using linear hashing (LH*) addressing. At least k+1 buckets are created on separate remote servers. At least k+1 key shares are generated for each of at least one encryption key. Each encryption key has a unique key number. Each key share is stored in a different key share record. Each of the key share records is stored in a different bucket using LH* addressing. Encrypted application data is generated by encrypting the application data with the encryption key(s). The encrypted application data is stored in encrypted data record(s). Each of the encrypted data records is stored in a different bucket among the buckets using LH* addressing.

Figure 16:
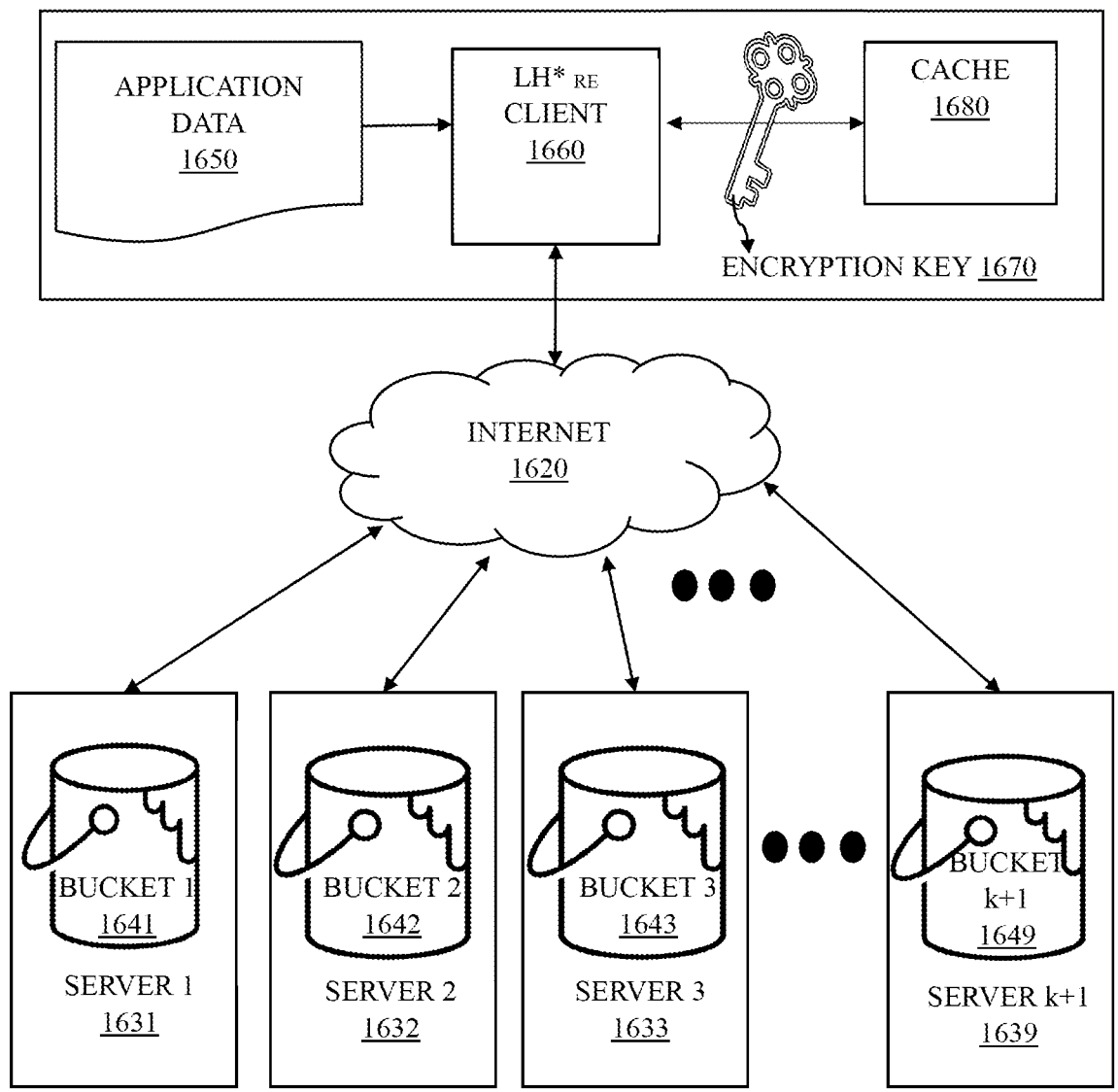
FIG. 16 is a system block diagram showing an example client interacting with k+1 servers that allows a user to define their encryption and relieves a user from the task of managing keys used for data security, as per an aspect of an embodiment of the present invention.

FIG. 16 is a system block diagram showing an example client 1610 interacting with k+1 remote servers (1631, 1632, 1633, . . . 1639) as per an aspect of an embodiment of the present invention. In these embodiments, one or more of clients (1610, 1611, . . . 1619) may have an LH*RE client 1610 configured to store a version of application data 1650 encrypted with an encryption key 1670 on remote servers (1631, 1632, 1633, . . . 1639). The remote servers (1631, 1632, 1633, . . . 1639) will likely be specialized servers configured to communicate with many client systems (1610, 1611 . . . 1619) and manage data buckets (1641, 1642, 1643, . . . 1649). The remote servers (1631, 1632, 1633, . . . 1639) may be geographically diverse. Some of the remote servers (1631, 1632, 1633, . . . 1639) may also be under the control of various organizations. In this way, the stored data may become harder for a third party to locate and retrieve all of the stored application data 1650 and key(s) 1670 from the data. Embodiments of the LH*RE client 1660 may be implemented as a computer readable storage medium containing a series of instructions that when executed by one or more processors on clients (1610, 1611, . . . 1619), causes the one or more processors to store application data 1650 on at least k+1 remote servers (1631, 1632, 1633, . . . 1639). In these embodiments, k is a freely set parameter of the system.

Figure 17:
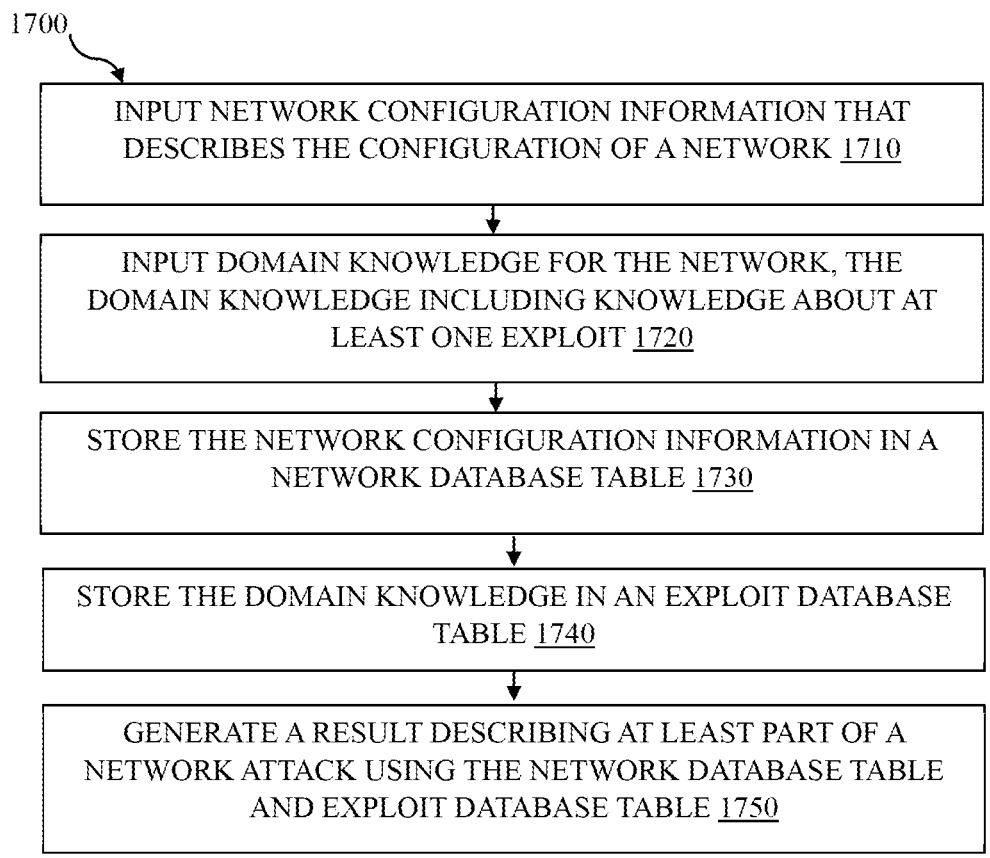
FIG. 17 is a flow diagram describing a method for determining at least part of a network attack according to an embodiment of the present invention.

Attack graphs depict ways in which an adversary exploits system vulnerabilities in a network such as a computer network. Attack graphs may be important in defending against well-orchestrated network intrusions. FIG. 17 is a flow diagram of an aspect of an embodiment where the network configuration information input module is preferably configured to input network configuration information that describes the configuration of a network in 1710. The domain knowledge input module is preferably configured to input domain knowledge for the network in 1720. Domain knowledge may include knowledge about various exploits in the network. The network configuration information storage module is preferably configured to store network configuration information in at least one network database table in 1730. Similarly, the domain knowledge storage module is preferably configured to store the domain knowledge in at least one exploit database table 1740. The result generation module is preferably configured to generate a result using the network database table and exploit database table in 1750. The result may be generated in many ways.

In an embodiment, an Intrusion Detection System (IDS) is deployed on the system. An IDS is software and/or hardware designed to detect unwanted attempts at accessing, manipulating, and/or disabling computer systems, mainly through a network, such as the Internet. An intrusion detection system is used to detect malicious behaviors that can compromise the security of networked computer systems. An IDS may include Sensor(s) that are deployed at strategic locations in the network, which monitor traffic at the sensor location and generate security events upon detection of malicious behaviors; A central engine that records events (e.g., in a database) logged by the sensors; and Console(s) to monitor events and control the sensors. In some IDS implementations, all three components are combined in a single device or appliance. In a true distributed system, numerous sensors are deployed at various points in the network, which communicate over secure channels to the central engine. Multiple consoles may then interact with the central engine. In network-based intrusion detection systems (NIDS), sensors are located at monitoring points in a network. Traditionally, sensors may be placed at network borders or in a network demilitarized zone (DMZ), with the assumption that attacks are launched from outside the network to be defended. The sensor monitors network traffic at its point of deployment and analyzes the traffic content for patterns of malicious behavior.

Embodiments of the present invention locate the placement of intrusion detection system (IDS) sensors and prioritize IDS alerts using attack graph analysis. One embodiment predicts multiple ways of penetrating a network to reach critical assets. The set of such paths through the network constitutes an attack graph, which may be aggregated according to underlying network regularities, reducing the complexity of analysis. By knowing the paths of vulnerability through our networks, one may reduce the impact of attacks. IDS sensors may be placed to cover the attack graph, using a minimal number of sensors. This should minimize the cost of sensors, including effort of deploying, configuring, and maintaining them, while maintaining complete coverage of potential attack paths. An embodiment addresses the sensor placement as an instance of the non-deterministic polynomial-time (NP) hard minimal set cover problem using an efficient greedy algorithm. Once sensors are deployed and alerts are raised, a predictive attack graph may be used to prioritize alerts based on attack graph distance to critical assets.

Figure 18:
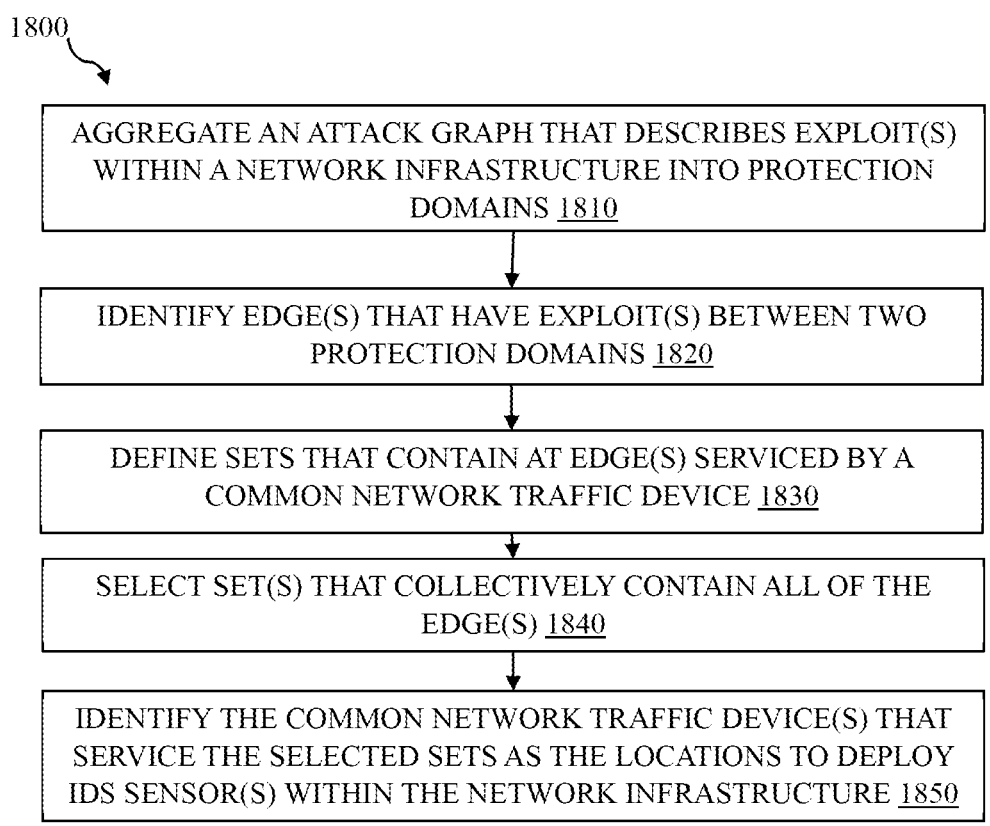
FIG. 18 depicts a flow diagram for a computer readable storage medium demonstrating instructions that cause the processor to perform a method for identifying locations to deploy intrusion detection system (IDS) Sensors within a network infrastructure, as per an aspect of an embodiment of the present invention.

An embodiment of the present invention, as exemplified in FIG. 18, is a computer readable storage medium that contains instructions that when executed by at least one processor, causes the processor(s) to perform a method 1800 for identifying locations to deploy IDS sensor(s) within a network infrastructure. The method 1800 for identifying locations to deploy IDS sensor(s) within a network may comprise aggregating an attack graph that describes exploit(s) within a network infrastructure into protection domains 1810. The attack graph may be configured to describe exploit(s) in at least a part of the network infrastructure. Further, the embodiment may include identifying edge(s) that have exploit(s) between two protection domains 1820, defining sets that contain edge(s) serviced by a common network traffic device 1830, selecting set(s) that collectively contain all of the edge(s) 1840, and identifying the common network traffic device(s) that service the selected sets as the locations to deploy IDS sensor(s) within the network infrastructure 1850.

In an embodiment of the present invention, the selecting set(s) that collectively contain all of the edge(s) 1840 may further include selecting set(s) that cover critical path(s) through the network infrastructure that lead to a critical asset. The set selection method 1840 may further include selecting set(s) that cover critical path(s) through the network infrastructure that starts at an assumed threat source. Further variations of this embodiment may allow the set selection method 1840 to include selecting a minimal number of sensors necessary to cover critical path(s) through the network infrastructure. The set selection method 1840 may also further include utilizing a greedy algorithm. The greedy algorithm favors large sets that contain edge(s) that are infrequently used. Frequency is the number of times an edge appears across all sets.

In an embodiment of the present invention, the method 1800 for identifying locations to deploy on IDS sensor(s) within a network may further include prioritizing alerts from IDS sensors deployed within the network infrastructure using at least one attack graph distance to at least one critical asset. Attack graph distance may be measured in multiple ways such as: 1) the number of edges that are traversed to reach critical assets; 2) the number of protection domains crossed; and 3) the number of network traffic devices.

INCORPORATION BY REFERENCE

All references, including granted patents and patent application publications, referred to herein are incorporated herein by reference in their entirety.

US Publication Number 20080154177A1 titled, "System and method for remote monitoring and/or management of infusion therapies."
U.S. Pat. No. 8,882,703 titled, "Drug delivery in association with medical or surgical procedures."
U.S. Pat. No. 9,649,439 titled, "Systems and methods for facilitating patient-based adjustment of drug infusion."
U.S. Pat. No. 9,067,016 titled, "Infusion monitoring device and method for monitoring the infusion dripping rate and alarming for the irregularities of the infusion."
U.S. Pat. No. 6,689,091 titled, "Medical apparatus with remote control."
U.S. Pat. No. 8,285,328 titled, "Remote-controlled drug pump devices."
U.S. Pat. No. 9,031,793 titled, "Centralized hospital monitoring system for automatically detecting upper airway instability and for preventing and aborting adverse drug reactions."
US Publication Number 20210174778A1 titled "Biometric, physiological or environmental monitoring using a closed chamber."
U.S. Pat. No. 9,814,426 titled, "Mobile wearable electromagnetic brain activity monitor." US Publication Number 20180158555A1 titled, "Medical kiosk and method of use."
U.S. Pat. No. 10,783,989 titled, "Devices, systems, and methods for automated data collection."
U.S. Pat. No. 9,203,861 titled "Methods and systems for determining hardening strategies"
U.S. Pat. No. 9,436,822 titled "Virtual browsing environment"
U.S. Pat. No. 10,956,184 titled "Malware detector"
U.S. Pat. No. 9,846,588 titled "on demand disposable virtual work system"
U.S. Pat. No. 8,082,452 titled "Protecting sensitive data associations"
U.S. Publication 20100054481 titled "Scalable distributed data structure with recoverable encryption"
U.S. Pat. No. 8,566,269 titled "Interactive analysis of attack graphs using relational queries"
U.S. Publication 20100058456 titled "IDS sensor placement using attack graphs"

What is claimed is:

1. A system, comprising:
    a timer module comprising a timer configured to set a duration for a session;
    an infusion module comprising an infusing device configured for administering a drug to a patient;
    a patient monitoring module comprising a first sensor configured for monitoring a physiological condition of the patient;
    a drug monitoring and control module comprising a second sensor configured for monitoring a drug delivery to the patient;
    an alarm generating module comprising signal generator that generates an indication signal when a value of the physiological condition is outside a predefined threshold; and
    wherein the duration for the session is automatically and dynamically adjusted in real time by the system during the session based on feedback from the first sensor and the second sensor; and
    wherein a future drug delivery is automatically and dynamically adjusted in real time by the system during the session based on feedback from the first sensor and the second sensor.

2. The system of claim 1, further comprising a remote monitoring system for remotely monitoring the system.

3. The system of claim 1, wherein the duration for the session is a predetermined value based on a health condition of the patient.

4. The system of claim 1, wherein the session comprises at least one of a psychotherapy session, a chemotherapy session, and a surgery.

5. The system of claim 1, wherein the infusing device is configured to administer a plurality of drugs each having a unique identifier and as per a dosage rule and in a specific sequence.

6. The system of claim 1, wherein administering the drug is continuous and automated.

7. The system of claim 1, wherein the patient monitoring module comprises a monitoring system to monitor at least a parameter related to the patient, wherein the parameter comprises at least one selected from a brain activity, a responsiveness, a seizure, a vomiting, a breathing rate, a heart rate, a heart activity, a body temperature, a blood pressure, a pupil color, a pupil dilation, a pupil constriction, a sound made by the patient, a lip color, a fingertip color, a first response to an outside stimuli, a second response to a loud noise, a shaking of a body part, and a skin color.

8. The system of claim 1, wherein the system further comprises artificial intelligent techniques to determine a quantity of the drug and a drug rate based on the physiological condition of the patient during the session.

9. The system of claim 1, wherein the indicating signal is a light signal and is configured to be a light cue at least in one of a room, a door, a chair, a personal wearable device, and a computer.

10. The system of claim 1, wherein the indicating signal is a light signal of a color and is configured for a specific message.

11. The system of claim 1, wherein the system further comprises an authentication module for the session.

12. The system of claim 1, wherein the system further comprises a cyber security module for securing first data set of the patient and second data set of the session.

13. The system of claim 1, wherein the predefined threshold is configured for the patient based on historic health record and current physiological condition.

14. The system of claim 1, wherein the drug delivery is adjusted to change a comfort level of the patient based on feedback from the first sensor and the second sensor; and wherein the comfort level is measured by measuring the movement of a body part of the patient.

15. A system, comprising:
   a timer module comprising a timer configured to monitor a duration for a session;
   an automated infusion module comprising a drug infusing device for administering a drug to a patient;
   a monitoring module comprising,
   a first sensor configured for monitoring of a physiological condition of the patient;
   a second sensor configured for monitoring a drug delivery to the patient, wherein the drug delivery comprises a quantity of the drug and a rate of drug delivery;
   a third sensor configured for monitoring a patient movement;
   a fourth sensor configured for monitoring an eye activity of the patient;
   a fifth sensor configured for monitoring a brain activity of the patient;
   an alarm generating module comprising a signal generator for generating an indication signal configured to generate an alarm when a value of at least one of the physiological condition, the duration of the session, and the drug delivery is outside a predefined threshold; and
   wherein the duration for the session is automatically and dynamically adjusted by the system in real time based on at least one of the physiological condition, the drug delivery, the patient movement, the eye activity, and the brain activity;
   wherein a future drug delivery is automatically and dynamically adjusted in real time based on at least one of the physiological condition, the drug delivery, the patient movement, the eye activity, and the brain activity; and
   wherein the system is configured for remote monitoring.

16. The system of claim 15, wherein the physiological condition comprises at least one of a heart rate, a respiratory rate, a blood pressure, a perspiration level, and a body temperature of the patient and the first sensor comprises at least one of an electrocardiogram electrode, a respiratory sensor, a blood pressure sensor, a sweat sensor, a temperature sensor.

17. The system of claim 15, wherein the third sensor is a pressure sensor that is integrated with a support surface on which the patient is supported.

18. The system of claim 15, wherein the fourth sensor configured for monitoring of the eye activity is configured to monitor at least one of a pupil color, a pupil dilation, a pupil constriction.

19. The system of claim 15, wherein the fifth sensor comprises an electroencephalogram configured to measure the brain activity and to identify a distinctive brain activity pattern that marks a loss of consciousness or a hallucination, wherein the electroencephalogram is configured to detect electrical activity of the brain of the patient.

20. The system of claim 1, wherein setting of the duration of the session is based on initial prediction of a dosage and a drug delivery rate.

* * * * *